US009340800B2

(12) United States Patent
Liu et al.

(10) Patent No.: US 9,340,800 B2
(45) Date of Patent: *May 17, 2016

(54) EXTENDED DNA-SENSING GRNAS

(71) Applicant: President and Fellows of Harvard College, Cambridge, MA (US)

(72) Inventors: David R. Liu, Lexington, MA (US); Johnny Hao Hu, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/326,361

(22) Filed: Jul. 8, 2014

(65) Prior Publication Data
US 2015/0071902 A1 Mar. 12, 2015

Related U.S. Application Data

(60) Provisional application No. 61/874,682, filed on Sep. 6, 2013.

(51) Int. Cl.
| C07H 21/02 | (2006.01) |
| C12N 15/00 | (2006.01) |
| C12N 5/00 | (2006.01) |
| C12N 15/11 | (2006.01) |
| C07K 14/195 | (2006.01) |
| C12N 15/90 | (2006.01) |
| C12N 15/115 | (2010.01) |
| C12N 9/22 | (2006.01) |
| C12N 15/01 | (2006.01) |
| C12N 15/113 | (2010.01) |
| A61K 48/00 | (2006.01) |

(52) U.S. Cl.
CPC ............... *C12N 15/907* (2013.01); *C12N 9/22* (2013.01); *C12N 15/01* (2013.01); *C12N 15/113* (2013.01); *C12N 15/115* (2013.01); *A61K 48/00* (2013.01); *C12N 2310/10* (2013.01); *C12N 2310/12* (2013.01); *C12N 2310/16* (2013.01); *C12N 2310/3519* (2013.01); *C12N 2310/53* (2013.01); *C12N 2320/53* (2013.01)

(58) Field of Classification Search
None
See application file for complete search history.

(56) References Cited

U.S. PATENT DOCUMENTS

| 5,580,737 | A | 12/1996 | Polisky et al. |
| 5,780,053 | A | 7/1998 | Ashley et al. |
| 6,057,153 | A | 5/2000 | George et al. |
| 7,479,573 | B2 | 1/2009 | Chu et al. |
| 7,794,931 | B2 | 9/2010 | Breaker et al. |
| 7,919,277 | B2 | 4/2011 | Russell et al. |
| 8,361,725 | B2 | 1/2013 | Russell et al. |
| 8,492,082 | B2 | 7/2013 | De Franciscis et al. |
| 8,546,553 | B2 | 10/2013 | Terns et al. |
| 8,569,256 | B2 | 10/2013 | Heyes et al. |
| 8,680,069 | B2 | 3/2014 | de Fougerolles et al. |
| 8,691,750 | B2 | 4/2014 | Constien et al. |
| 8,697,359 | B1 * | 4/2014 | Zhang .......................... 435/6.1 |
| 8,709,466 | B2 | 4/2014 | Coady et al. |
| 8,728,526 | B2 | 5/2014 | Heller |
| 8,748,667 | B2 | 6/2014 | Budzik et al. |
| 8,758,810 | B2 | 6/2014 | Okada et al. |
| 8,759,103 | B2 | 6/2014 | Kim et al. |
| 8,759,104 | B2 | 6/2014 | Unciti-Broceta et al. |
| 8,771,728 | B2 | 7/2014 | Huang et al. |
| 8,790,664 | B2 | 7/2014 | Pitard et al. |
| 8,846,578 | B2 | 9/2014 | McCray et al. |
| 8,993,233 | B2 | 3/2015 | Zhang et al. |
| 8,999,641 | B2 | 4/2015 | Zhang et al. |
| 9,068,179 | B1 | 6/2015 | Liu et al. |
| 9,163,284 | B2 | 10/2015 | Liu et al. |
| 2006/0088864 | A1 | 4/2006 | Smolke et al. |
| 2008/0124725 | A1 | 5/2008 | Barrangou et al. |
| 2008/0182254 | A1 | 7/2008 | Hall et al. |
| 2009/0130718 | A1 | 5/2009 | Short |
| 2009/0234109 | A1 | 9/2009 | Han et al. |
| 2010/0076057 | A1 | 3/2010 | Sontheimer et al. |
| 2010/0093617 | A1 | 4/2010 | Barrangou et al. |
| 2010/0104690 | A1 | 4/2010 | Barrangou et al. |
| 2010/0316643 | A1 | 12/2010 | Eckert et al. |
| 2011/0059160 | A1 | 3/2011 | Essner et al. |
| 2011/0104787 | A1 | 5/2011 | Church et al. |
| 2011/0189776 | A1 | 8/2011 | Terns et al. |

(Continued)

FOREIGN PATENT DOCUMENTS

| AU | 2012244264 | 11/2012 |
| CN | 103233028 A | 8/2013 |

(Continued)

OTHER PUBLICATIONS

International Search Report and Written Opinion for PCT/US2014/052231, mailed Dec. 4, 2014.

(Continued)

*Primary Examiner* — Richard Schnizer

(74) *Attorney, Agent, or Firm* — Wolf, Greenfield & Sacks, P.C.

(57) ABSTRACT

Some aspects of this disclosure provide compositions, methods, systems, and kits for controlling the activity and/or improving the specificity of RNA-programmable endonucleases, such as Cas9. For example, provided are guide RNAs (gRNAs) that are engineered to exist in an "on" or "off" state, which control the binding and hence cleavage activity of RNA-programmable endonucleases. Some aspects of this disclosure provide gRNAs that modulate the activity of an RNA-programmable endonuclease based on the presence or absence of an extended DNA (xDNA).

30 Claims, 12 Drawing Sheets

(56) References Cited

U.S. PATENT DOCUMENTS

| | | |
|---|---|---|
| 2011/0217739 A1 | 9/2011 | Terns et al. |
| 2012/0141523 A1 | 6/2012 | Castado et al. |
| 2012/0270273 A1 | 10/2012 | Zhang et al. |
| 2013/0117869 A1 | 5/2013 | Duchateau et al. |
| 2013/0130248 A1 | 5/2013 | Haurwitz et al. |
| 2013/0158245 A1 | 6/2013 | Russell et al. |
| 2013/0165389 A1 | 6/2013 | Schellenberger et al. |
| 2013/0344117 A1 | 12/2013 | Mirosevich et al. |
| 2014/0005269 A1 | 1/2014 | Ngwuluka et al. |
| 2014/0017214 A1 | 1/2014 | Cost |
| 2014/0018404 A1 | 1/2014 | Chen et al. |
| 2014/0044793 A1 | 2/2014 | Goll et al. |
| 2014/0065711 A1 | 3/2014 | Liu et al. |
| 2014/0068797 A1* | 3/2014 | Doudna .............. C12N 15/102 800/18 |
| 2014/0127752 A1 | 5/2014 | Zhou et al. |
| 2014/0141094 A1 | 5/2014 | Smyth et al. |
| 2014/0141487 A1 | 5/2014 | Feldman et al. |
| 2014/0186843 A1 | 7/2014 | Zhang et al. |
| 2014/0186958 A1 | 7/2014 | Zhang et al. |
| 2014/0234289 A1 | 8/2014 | Liu et al. |
| 2014/0273037 A1 | 9/2014 | Wu |
| 2014/0273226 A1 | 9/2014 | Wu |
| 2014/0273230 A1 | 9/2014 | Chen et al. |
| 2014/0295556 A1 | 10/2014 | Joung et al. |
| 2014/0295557 A1 | 10/2014 | Joung et al. |
| 2014/0342456 A1 | 11/2014 | Mali et al. |
| 2014/0342457 A1 | 11/2014 | Mali et al. |
| 2014/0342458 A1 | 11/2014 | Mali et al. |
| 2014/0349400 A1 | 11/2014 | Jakimo et al. |
| 2014/0356867 A1 | 12/2014 | Peter et al. |
| 2014/0356956 A1 | 12/2014 | Church et al. |
| 2014/0356958 A1 | 12/2014 | Mali et al. |
| 2014/0356959 A1 | 12/2014 | Church et al. |
| 2014/0357523 A1 | 12/2014 | Zeiner et al. |
| 2014/0377868 A1 | 12/2014 | Joung et al. |
| 2015/0010526 A1 | 1/2015 | Liu et al. |
| 2015/0031089 A1 | 1/2015 | Lindstrom |
| 2015/0031132 A1 | 1/2015 | Church et al. |
| 2015/0031133 A1 | 1/2015 | Church et al. |
| 2015/0044191 A1 | 2/2015 | Liu et al. |
| 2015/0044192 A1 | 2/2015 | Liu et al. |
| 2015/0044772 A1 | 2/2015 | Zhao |
| 2015/0050699 A1 | 2/2015 | Siksnys et al. |
| 2015/0056177 A1 | 2/2015 | Liu et al. |
| 2015/0056629 A1 | 2/2015 | Guthrie-Honea |
| 2015/0064138 A1 | 3/2015 | Kuan-Ta Lu et al. |
| 2015/0064789 A1 | 3/2015 | Paschon et al. |
| 2015/0071898 A1 | 3/2015 | Liu et al. |
| 2015/0071899 A1 | 3/2015 | Liu et al. |
| 2015/0071900 A1 | 3/2015 | Liu et al. |
| 2015/0071901 A1 | 3/2015 | Liu et al. |
| 2015/0071903 A1 | 3/2015 | Liu et al. |
| 2015/0071906 A1 | 3/2015 | Liu et al. |
| 2015/0079680 A1 | 3/2015 | Bradley et al. |
| 2015/0098954 A1 | 4/2015 | Hyde et al. |
| 2015/0118216 A1 | 4/2015 | Liu et al. |
| 2015/0132269 A1 | 5/2015 | Orkin et al. |
| 2015/0140664 A1 | 5/2015 | Byrne et al. |
| 2015/0159172 A1 | 6/2015 | Miller et al. |
| 2015/0165054 A1 | 6/2015 | Liu et al. |
| 2015/0166980 A1 | 6/2015 | Liu et al. |
| 2015/0166981 A1 | 6/2015 | Liu et al. |
| 2015/0166982 A1 | 6/2015 | Liu et al. |
| 2015/0166984 A1 | 6/2015 | Liu et al. |
| 2015/0166985 A1 | 6/2015 | Liu et al. |
| 2015/0191744 A1 | 7/2015 | Wolfe et al. |
| 2015/0197759 A1 | 7/2015 | Xu et al. |
| 2015/0211058 A1 | 7/2015 | Carstens et al. |
| 2015/0218573 A1 | 8/2015 | Loque et al. |
| 2015/0225773 A1 | 8/2015 | Farmer et al. |
| 2015/0252358 A1 | 9/2015 | Maeder et al. |

FOREIGN PATENT DOCUMENTS

| | | |
|---|---|---|
| CN | 103388006 A | 11/2013 |
| CN | 103614415 A | 3/2014 |
| CN | 103642836 A | 3/2014 |
| CN | 103668472 A | 3/2014 |
| CN | 103820441 A | 5/2014 |
| CN | 103820454 A | 5/2014 |
| CN | 103911376 A | 7/2014 |
| CN | 103923911 A | 7/2014 |
| CN | 104004778 A | 8/2014 |
| CN | 104109687 A | 10/2014 |
| CN | 104178461 A | 12/2014 |
| CN | 104342457 | 2/2015 |
| CN | 104404036 A | 3/2015 |
| CN | 104450774 A | 3/2015 |
| CN | 104480144 A | 4/2015 |
| CN | 104498493 A | 4/2015 |
| CN | 104504304 A | 4/2015 |
| CN | 104531704 A | 4/2015 |
| CN | 104531705 A | 4/2015 |
| CN | 104560864 A | 4/2015 |
| CN | 104593418 A | 5/2015 |
| CN | 104593422 A | 5/2015 |
| CN | 104611370 A | 5/2015 |
| CN | 104651392 A | 5/2015 |
| CN | 104651398 A | 5/2015 |
| CN | 104651399 A | 5/2015 |
| CN | 104651401 A | 5/2015 |
| CN | 104673816 A | 6/2015 |
| CN | 104726449 A | 6/2015 |
| CN | 104726494 A | 6/2015 |
| CN | 104745626 A | 7/2015 |
| CN | 104762321 A | 7/2015 |
| CN | 104805078 A | 7/2015 |
| CN | 104805099 A | 7/2015 |
| CN | 104805118 A | 7/2015 |
| CN | 104846010 A | 8/2015 |
| CN | 104894068 A | 9/2015 |
| CN | 104894075 A | 9/2015 |
| CN | 104928321 A | 9/2015 |
| CN | 103388006 B | 10/2015 |
| WO | WO 2006/002547 A1 | 1/2006 |
| WO | WO 2006/042112 A2 | 4/2006 |
| WO | WO 2007/025097 A2 | 3/2007 |
| WO | WO 2007/136815 A2 | 11/2007 |
| WO | WO 2010/054108 A2 | 5/2010 |
| WO | WO 2010/054154 A2 | 5/2010 |
| WO | WO 2010/068289 A2 | 6/2010 |
| WO | WO 2010/075424 A2 | 7/2010 |
| WO | WO 2010/102257 A2 | 9/2010 |
| WO | WO 2010/129019 A2 | 11/2010 |
| WO | WO 2010/144150 A2 | 12/2010 |
| WO | WO 2011/017293 A2 | 2/2011 |
| WO | WO 2011/053868 A1 | 5/2011 |
| WO | WO 2011/053982 A2 | 5/2011 |
| WO | WO 2011/109031 A1 | 9/2011 |
| WO | WO 2012/054726 A1 | 4/2012 |
| WO | WO 2012/065043 A2 | 5/2012 |
| WO | WO 2012/138927 A2 | 10/2012 |
| WO | WO 2012/158985 A2 | 11/2012 |
| WO | WO 2012/158986 A2 | 11/2012 |
| WO | WO 2012/164565 A1 | 12/2012 |
| WO | WO 2013/012674 A1 | 1/2013 |
| WO | WO 2013/013105 A2 | 1/2013 |
| WO | WO 2013/066438 A2 | 5/2013 |
| WO | WO 2013/098244 A1 | 7/2013 |
| WO | WO 2013/126794 A1 | 8/2013 |
| WO | WO 2013/130824 A1 | 9/2013 |
| WO | WO 2013/141680 A1 | 9/2013 |
| WO | WO 2013/142378 A9 | 9/2013 |
| WO | WO 2013/142578 A2 | 9/2013 |
| WO | WO 2013/160230 A1 | 10/2013 |
| WO | WO 2013/166315 A1 | 11/2013 |
| WO | WO 2013/169398 A2 | 11/2013 |
| WO | WO 2013/169802 A1 | 11/2013 |
| WO | WO 2013/176772 A2 | 11/2013 |
| WO | WO 2013/176915 A1 | 11/2013 |
| WO | WO 2013/176916 A1 | 11/2013 |

(56) References Cited

FOREIGN PATENT DOCUMENTS

| | | |
|---|---|---|
| WO | WO 2013/181440 A1 | 12/2013 |
| WO | WO 2013/186754 A2 | 12/2013 |
| WO | WO 2013/188037 A2 | 12/2013 |
| WO | WO 2013/188522 A2 | 12/2013 |
| WO | WO 2013/188638 A2 | 12/2013 |
| WO | WO 2013/192278 A1 | 12/2013 |
| WO | WO 2014/005042 A2 | 1/2014 |
| WO | WO 2014/011237 A1 | 1/2014 |
| WO | WO 2014/011901 A2 | 1/2014 |
| WO | WO 2014/018423 A2 | 1/2014 |
| WO | WO 2014/020608 A1 | 2/2014 |
| WO | WO 2014/022120 A1 | 2/2014 |
| WO | WO 2014/022702 A2 | 2/2014 |
| WO | WO 2014/036219 A2 | 3/2014 |
| WO | WO 2014/039513 A2 | 3/2014 |
| WO | WO 2014/039523 A1 | 3/2014 |
| WO | WO 2014/039684 A1 | 3/2014 |
| WO | WO 2014/039692 A2 | 3/2014 |
| WO | WO 2014/039702 A2 | 3/2014 |
| WO | WO 2014/039872 A1 | 3/2014 |
| WO | WO 2014/039970 A1 | 3/2014 |
| WO | WO 2014/041327 A1 | 3/2014 |
| WO | WO 2014/043143 A1 | 3/2014 |
| WO | WO 2014/047103 A2 | 3/2014 |
| WO | WO 2014/059173 A2 | 4/2014 |
| WO | WO 2014/065596 A1 | 5/2014 |
| WO | WO 2014/066505 A1 | 5/2014 |
| WO | WO 2014/068346 A2 | 5/2014 |
| WO | WO 2014/070887 A1 | 5/2014 |
| WO | WO 2014/071006 A1 | 5/2014 |
| WO | WO 2014/071219 A1 | 5/2014 |
| WO | WO 2014/071235 A1 | 5/2014 |
| WO | WO 2014/072941 A1 | 5/2014 |
| WO | WO 2014/081729 A1 | 5/2014 |
| WO | WO 2014/081730 A1 | 5/2014 |
| WO | WO 2014/081855 A1 | 5/2014 |
| WO | WO 2014/082644 A1 | 6/2014 |
| WO | WO 2014/085261 A1 | 6/2014 |
| WO | WO 2014/085593 A1 | 6/2014 |
| WO | WO 2014/085830 A2 | 6/2014 |
| WO | WO 2014/089212 A1 | 6/2014 |
| WO | WO 2014/089290 A1 | 6/2014 |
| WO | WO 2014/089348 A1 | 6/2014 |
| WO | WO 2014/089513 A1 | 6/2014 |
| WO | WO 2014/089533 A2 | 6/2014 |
| WO | WO 2014/089541 A2 | 6/2014 |
| WO | WO 2014/093479 A1 | 6/2014 |
| WO | WO 2014/093595 A1 | 6/2014 |
| WO | WO 2014/093622 A2 | 6/2014 |
| WO | WO 2014/093635 A1 | 6/2014 |
| WO | WO 2014/093655 A2 | 6/2014 |
| WO | WO 2014/093661 A2 | 6/2014 |
| WO | WO 2014/093694 A1 | 6/2014 |
| WO | WO 2014/093701 A1 | 6/2014 |
| WO | WO 2014/093709 A1 | 6/2014 |
| WO | WO 2014/093712 A1 | 6/2014 |
| WO | WO 2014/093718 A1 | 6/2014 |
| WO | WO 2014/093736 A1 | 6/2014 |
| WO | WO 2014/093768 A1 | 6/2014 |
| WO | WO 2014/093852 A1 | 6/2014 |
| WO | WO 2014/096972 A2 | 6/2014 |
| WO | WO 2014/099744 A1 | 6/2014 |
| WO | WO 2014/099750 A2 | 6/2014 |
| WO | WO 2014/113493 A1 | 7/2014 |
| WO | WO 2014/124226 A1 | 8/2014 |
| WO | WO 2014/127287 A1 | 8/2014 |
| WO | WO 2014/128324 A1 | 8/2014 |
| WO | WO 2014/128659 A1 | 8/2014 |
| WO | WO 2014/130955 A1 | 8/2014 |
| WO | WO 2014/131833 A1 | 9/2014 |
| WO | WO 2014/143381 A1 | 9/2014 |
| WO | WO 2014/144094 A1 | 9/2014 |
| WO | WO 2014/144155 A1 | 9/2014 |
| WO | WO 2014/144288 A1 | 9/2014 |
| WO | WO 2014/144592 A2 | 9/2014 |
| WO | WO 2014/144761 A2 | 9/2014 |
| WO | WO 2014/145599 A2 | 9/2014 |
| WO | WO 2014/150624 A1 | 9/2014 |
| WO | WO 2014/152432 A2 | 9/2014 |
| WO | WO 2014/153470 A2 | 9/2014 |
| WO | WO 2014/161821 A1 | 10/2014 |
| WO | WO 2014/164466 A1 | 10/2014 |
| WO | WO 2014/165177 A1 | 10/2014 |
| WO | WO 2014/165349 A1 | 10/2014 |
| WO | WO 2014/165612 A2 | 10/2014 |
| WO | WO 2014/165825 A2 | 10/2014 |
| WO | WO 2014/172458 A1 | 10/2014 |
| WO | WO 2014/172470 A | 10/2014 |
| WO | WO 2014/172489 A2 | 10/2014 |
| WO | WO 2014/182700 A1 | 11/2014 |
| WO | WO 2014/183071 A2 | 11/2014 |
| WO | WO 2014/184143 A1 | 11/2014 |
| WO | WO 2014/184741 A1 | 11/2014 |
| WO | WO 2014/184744 A1 | 11/2014 |
| WO | WO 2014/186585 A2 | 11/2014 |
| WO | WO 2014/186686 A2 | 11/2014 |
| WO | WO 2014/190181 A1 | 11/2014 |
| WO | WO 2014/191128 A1 | 12/2014 |
| WO | WO 2014/191518 A1 | 12/2014 |
| WO | WO 2014/191521 A2 | 12/2014 |
| WO | WO 2014/191525 A1 | 12/2014 |
| WO | WO 2014/191527 A1 | 12/2014 |
| WO | WO 2014/194190 A1 | 12/2014 |
| WO | WO 2014/197568 A2 | 12/2014 |
| WO | WO 2014/197748 A2 | 12/2014 |
| WO | WO 2014/199358 A1 | 12/2014 |
| WO | WO 2014/200659 A1 | 12/2014 |
| WO | WO 2014/201015 A2 | 12/2014 |
| WO | WO 2014/204578 A1 | 12/2014 |
| WO | WO 2014/204723 A1 | 12/2014 |
| WO | WO 2014/204724 A1 | 12/2014 |
| WO | WO 2014/204725 A1 | 12/2014 |
| WO | WO 2014/204726 A1 | 12/2014 |
| WO | WO 2014/204727 A1 | 12/2014 |
| WO | WO 2014/204728 A1 | 12/2014 |
| WO | WO 2014/204729 A1 | 12/2014 |
| WO | WO 2015/002780 A1 | 1/2015 |
| WO | WO 2015/004241 A2 | 1/2015 |
| WO | WO 2015/006290 A1 | 1/2015 |
| WO | WO 2015/006294 A2 | 1/2015 |
| WO | WO 2015/006498 A2 | 1/2015 |
| WO | WO 2015/006747 A2 | 1/2015 |
| WO | WO 2015/010114 A1 | 1/2015 |
| WO | WO 2015/013583 A2 | 1/2015 |
| WO | WO 2015/017866 A1 | 2/2015 |
| WO | WO 2015/018503 A1 | 2/2015 |
| WO | WO 2015/021353 A1 | 2/2015 |
| WO | WO 2015/021426 A1 | 2/2015 |
| WO | WO 2015/021990 A1 | 2/2015 |
| WO | WO 2015/024017 A2 | 2/2015 |
| WO | WO 2015/026883 A1 | 2/2015 |
| WO | WO 2015/026885 A1 | 2/2015 |
| WO | WO 2015/026886 A1 | 2/2015 |
| WO | WO 2015/026887 A1 | 2/2015 |
| WO | WO 2015/027134 A1 | 2/2015 |
| WO | WO 2015/030881 A1 | 3/2015 |
| WO | WO 2015/031619 A1 | 3/2015 |
| WO | WO 2015/031775 A1 | 3/2015 |
| WO | WO 2015/033293 A1 | 3/2015 |
| WO | WO 2015/034872 A2 | 3/2015 |
| WO | WO 2015/035136 A2 | 3/2015 |
| WO | WO 2015/035139 A1 | 3/2015 |
| WO | WO 2015/035162 A2 | 3/2015 |
| WO | WO 2015/040075 A1 | 3/2015 |
| WO | WO 2015/040402 A1 | 3/2015 |
| WO | WO 2015/048577 A2 | 4/2015 |
| WO | WO 2015/048690 A1 | 4/2015 |
| WO | WO 2015/052133 A1 | 4/2015 |
| WO | WO 2015/052231 A2 | 4/2015 |
| WO | WO 2015/053995 A1 | 4/2015 |
| WO | WO 2015/054253 A1 | 4/2015 |
| WO | WO 2015/057976 A1 | 4/2015 |
| WO | WO 2015/057980 A1 | 4/2015 |
| WO | WO 2015/059265 A1 | 4/2015 |

(56) References Cited

FOREIGN PATENT DOCUMENTS

| WO | WO 2015/065964 A1 | 5/2015 |
|---|---|---|
| WO | WO 2015/066119 A1 | 5/2015 |
| WO | WO 2015/066637 A1 | 5/2015 |
| WO | WO 2015/070083 A1 | 5/2015 |
| WO | WO 2015/070193 A1 | 5/2015 |
| WO | WO 2015/070212 A1 | 5/2015 |
| WO | WO 2015/071474 A2 | 5/2015 |
| WO | WO 2015/073683 A2 | 5/2015 |
| WO | WO 2015/073867 A1 | 5/2015 |
| WO | WO 2015/073990 A1 | 5/2015 |
| WO | WO 2015/075056 A1 | 5/2015 |
| WO | WO 2015/075154 A2 | 5/2015 |
| WO | WO 2015/075195 A1 | 5/2015 |
| WO | WO 2015/077290 A2 | 5/2015 |
| WO | WO 2015/077318 A1 | 5/2015 |
| WO | WO 2015/079056 A1 | 6/2015 |
| WO | WO 2015/079057 A2 | 6/2015 |
| WO | WO 2015/086795 A1 | 6/2015 |
| WO | WO 2015/086798 A2 | 6/2015 |
| WO | WO 2015/088643 A1 | 6/2015 |
| WO | WO 2015/089046 A1 | 6/2015 |
| WO | WO 2015/089077 A2 | 6/2015 |
| WO | WO 2015/089277 A1 | 6/2015 |
| WO | WO 2015/089351 A1 | 6/2015 |
| WO | WO 2015/089354 A1 | 6/2015 |
| WO | WO 2015/089364 A1 | 6/2015 |
| WO | WO 2015/089406 A1 | 6/2015 |
| WO | WO 2015/089419 A2 | 6/2015 |
| WO | WO 2015/089427 A1 | 6/2015 |
| WO | WO 2015/089462 A1 | 6/2015 |
| WO | WO 2015/089465 A1 | 6/2015 |
| WO | WO 2015/089473 A1 | 6/2015 |
| WO | WO 2015/089486 A2 | 6/2015 |
| WO | WO 2015/095804 A1 | 6/2015 |
| WO | WO 2015/099850 A1 | 7/2015 |
| WO | WO 2015/100929 A1 | 7/2015 |
| WO | WO 2015/103153 A1 | 7/2015 |
| WO | WO 2015/105928 A1 | 7/2015 |
| WO | WO 2015/108993 A1 | 7/2015 |
| WO | WO 2015/112790 A2 | 7/2015 |
| WO | WO 2015/112896 A2 | 7/2015 |
| WO | WO 2015/113063 A1 | 7/2015 |
| WO | WO 2015/115903 A1 | 8/2015 |
| WO | WO 2015/116686 A1 | 8/2015 |
| WO | WO 2015/117041 A1 | 8/2015 |
| WO | WO 2015/121454 A1 | 8/2015 |
| WO | WO 2015/122967 A1 | 8/2015 |
| WO | WO 2015/123339 A1 | 8/2015 |
| WO | WO 2015/126927 A2 | 8/2015 |
| WO | WO 2015/127428 A1 | 8/2015 |
| WO | WO 2015/127439 A1 | 8/2015 |
| WO | WO 2015/131101 A1 | 9/2015 |
| WO | WO 2015/134812 A1 | 9/2015 |
| WO | WO 2015/136001 A1 | 9/2015 |
| WO | WO 2015/138510 A1 | 9/2015 |
| WO | WO 2015/138739 A2 | 9/2015 |
| WO | WO 2015/138855 A1 | 9/2015 |
| WO | WO 2015/138870 A2 | 9/2015 |
| WO | WO 2015/139008 A1 | 9/2015 |
| WO | WO 2015/139139 A1 | 9/2015 |
| WO | WO 2015/143046 A2 | 9/2015 |
| WO | WO 2015/148670 A1 | 10/2015 |
| WO | WO 2015/148680 A1 | 10/2015 |
| WO | WO 2015/148761 A1 | 10/2015 |
| WO | WO 2015/148860 A1 | 10/2015 |
| WO | WO 2015/148863 A2 | 10/2015 |
| WO | WO 2015/153760 A2 | 10/2015 |
| WO | WO 2015/153780 A1 | 10/2015 |
| WO | WO 2015/153789 A1 | 10/2015 |
| WO | WO 2015/153791 A1 | 10/2015 |
| WO | WO 2015/153940 A1 | 10/2015 |
| WO | WO 2015/155341 A1 | 10/2015 |
| WO | WO 2015/155686 A2 | 10/2015 |
| WO | WO 2015/157070 A2 | 10/2015 |
| WO | WO 2015/157534 A1 | 10/2015 |
| WO | WO 2015/159068 A1 | 10/2015 |
| WO | WO 2015/159086 A1 | 10/2015 |
| WO | WO 2015/159087 A1 | 10/2015 |
| WO | WO 2015/160683 A1 | 10/2015 |
| WO | WO 2015/161276 A2 | 10/2015 |
| WO | WO 2015/163733 A1 | 10/2015 |
| WO | WO 2015/164748 A1 | 10/2015 |
| WO | WO 2015/166272 A2 | 11/2015 |
| WO | WO 2015/168125 A1 | 11/2015 |
| WO | WO 2015/168158 A1 | 11/2015 |
| WO | WO 2015/168404 A1 | 11/2015 |
| WO | WO 2015/168547 A2 | 11/2015 |

OTHER PUBLICATIONS

International Search Report and Written Opinion for PCT/US2014/050283, mailed Nov. 6, 2014.
Invitation to Pay Additional Fees for PCT/US2014/054291, mailed Dec. 18, 2014.
Genbank Submission; NIH/NCBI, Accession No. J04623. Kita et al., Apr. 26, 1993. 2 pages.
NCBI Reference Sequence: NM_002427.3. Wu et al., May 3, 2014. 5 pages.
Barrangou, RNA-mediated programmable DNA cleavage. Nat Biotechnol. Sep. 2012;30(9):836-8. doi: 10.1038/nbt.2357.
Carroll, A CRISPR approach to gene targeting. Mol Ther. Sep. 2012;20(9):1658-60. doi: 10.1038/mt.2012.171.
Fuchs et al., Polyarginine as a multifunctional fusion tag. Protein Sci. Jun. 2005;14(6):1538-44.
Liu et al., Fast Colorimetric Sensing of Adenosine and Cocaine Based on a General Sensor Design Involving Aptamers and Nanoparticles. Angew Chem. 2006;118(1):96-100.
Mussolino et al., Tale nucleases: tailored genome engineering made easy. Curr Opin Biotechnol. Oct. 2012;23(5):644-50. doi: 10.1016/j.copbio.2012.01.013. Epub Feb. 17, 2012.
O'Connell et al., Programmable RNA recognition and cleavage by CRISPR/Cas9. Nature. Sep. 28, 2014. doi: 10.1038/nature13769.
Zhang et al., CRISPR/Cas9 for genome editing: progress, implications and challenges. Hum Mol Genet. Sep. 15, 2014;23(R1):R40-6. doi: 10.1093/hmg/ddu125. Epub Mar. 20, 2014.
U.S. Appl. No. 61/716,256, filed Oct. 19, 2012, Jinek et al.
U.S. Appl. No. 61/717,324, filed Oct. 23, 2012, Cho et al.
U.S. Appl. No. 61/734,256, filed Dec. 6, 2012, Chen et al.
U.S. Appl. No. 61/758,624, filed Jan. 30, 2013, Chen et al.
U.S. Appl. No. 61/761,046, filed Feb. 5, 2013, Knight et al.
U.S. Appl. No. 61/794,422, filed Mar. 15, 2013, Knight et al.
U.S. Appl. No. 61/803,599, filed Mar. 20, 2013, Kim et al.
U.S. Appl. No. 61/837,481, filed Jun. 20, 2013, Cho et al.
U.S. Appl. No. 14/258,458, filed Apr. 22, 2014, Cong.
International Search Report and Written Opinion for PCT/US2012/047778, mailed May 30, 2013.
International Preliminary Report on Patentability for PCT/US2012/047778, mailed Feb. 6, 2014.
International Search Report for PCT/US2013/032589, mailed Jul. 26, 2013.
Genbank Submission; NIH/NCBI, Accession No. J04623. Kita et al., Aug. 26, 1993. 2 pages.
Genbank Submission; NIH/NCBI, Accession No. NC_002737.1. Ferretti et al., Jun. 27, 2013. 1 page.
Genbank Submission; NIH/NCBI, Accession No. NC_015683.1. Trost et al., Jul. 6, 2013. 1 page.
Genbank Submission; NIH/NCBI, Accession No. NC_016782.1. Trost et al., Jun. 11, 2013. 1 page.
Genbank Submission; NIH/NCBI, Accession No. NC_016786.1. Trost et al., Aug. 28, 2013. 1 page.
Genbank Submission; NIH/NCBI, Accession No. NC_017053.1. Fittipaldi et al., Jul. 6, 2013. 1 page.
Genbank Submission; NIH/NCBI, Accession No. NC_017317.1. Trost et al., Jun. 11, 2013. 1 page.
Genbank Submission; NIH/NCBI, Accession No. NC_017861.1. Heidelberg et al., Jun. 11, 2013. 1 page.
Genbank Submission; NIH/NCBI, Accession No. NC_018010.1. Lucas et al., Jun. 11, 2013. 2 pages.

(56) References Cited

OTHER PUBLICATIONS

Genbank Submission; NIH/NCBI, Accession No. NC_018721.1. Feng et al., Jun. 11, 2013. 1 pages.
Genbank Submission; NIH/NCBI, Accession No. NC_021284.1. Ku et al., Jul. 12, 2013. 1 page.
Genbank Submission; NIH/NCBI, Accession No. NC_021314.1. Zhang et al., Jul. 15, 2013. 1 page.
Genbank Submission; NIH/NCBI, Accession No. NC_021846.1. Lo et al., Jul. 22, 2013. 1 page.
Genbank Submission; NIH/NCBI, Accession No. NP_472073.1. Glaser et al., Jun. 27, 2013. 2 pages.
Genbank Submission; NIH/NCBI, Accession No. P42212. Prasher et al., Mar. 19, 2014. 7 pages.
Genbank Submission; NIH/NCBI, Accession No. YP_002342100.1. Bernardini et al., Jun. 10, 2013. 2 pages.
Genbank Submission; NIH/NCBI, Accession No. YP_002344900.1. Gundogdu et al., Mar. 19, 2014. 2 pages.
Genbank Submission; NIH/NCBI, Accession No. YP_820832.1. Makarova et al., Aug. 27, 2013. 2 pages.
Uniprot Submission; UniProt, Accession No. P04275. Last modified Jul. 9, 2014, version 107. 29 pages.
Uniprot Submission; UniProt, Accession No. P04264. Last modified Jun. 11, 2014, version 6. 15 pages.
Uniprot Submission; UniProt, Accession No. P01011. Last modified Jun. 11, 2014, version 2. 15 pages.
Aihara et al., A conformational switch controls the DNA cleavage activity of lambda integrase. Mol Cell. Jul. 2003;12(1):187-98.
Ames et al., A eubacterial riboswitch class that senses the coenzyme tetrahydrofolate. Chem Biol. Jul. 30, 2010;17(7):681-5. doi: 10.1016/j.chembiol.2010.05.020.
Barrangou et al., CRISPR provides acquired resistance against viruses in prokaryotes. Science. Mar. 23, 2007;315(5819):1709-12.
Batey et al., Structure of a natural guanine-responsive riboswitch complexed with the metabolite hypoxanthine. Nature. Nov. 18, 2004;432(7015):411-5.
Buskirk et al., Directed evolution of ligand dependence: small-molecule-activated protein splicing. Proc Natl Acad Sci USA. Jul. 20, 2004;101(29):10505-10. Epub Jul. 9, 2004.
Carroll et al., Gene targeting in *Drosophila* and Caenorhabditis elegans with zinc-finger nucleases. Methods Mol Biol. 2008;435:63-77. doi: 10.1007/978-1-59745-232-8_5.
Charpentier et al., Biotechnology: Rewriting a genome. Nature. Mar. 7, 2013;495(7439):50-1. doi: 10.1038/495050a.
Cho et al., Analysis of off-target effects of CRISPR/Cas-derived RNA-guided endonucleases and nickases. Genome Res. Jan. 2014;24(1):132-41. doi: 10.1101/gr.162339.113. Epub Nov. 19, 2013.
Chylinski et al., The tracrRNA and Cas9 families of type II CRISPR-Cas immunity systems. RNA Biol. May 2013;10(5):726-37. doi: 10.4161/rna.24321. Epub Apr. 5, 2013.
Cobb et al., Directed evolution as a powerful synthetic biology tool. Methods. Mar. 15, 2013;60(1):81-90. doi: 10.1016/j.ymeth.2012.03.009. Epub Mar. 23, 2012.
Cobb et al., Directed evolution: an evolving and enabling synthetic biology tool. Curr Opin Chem Biol. Aug. 2012;16(3-4):285-91. doi:10.1016/j.cbpa.2012.05.186. Epub Jun. 4, 2012. Review.
Cong et al., Multiplex genome engineering using CRISPR/Cas systems. Science. Feb. 15, 2013;339(6121):819-23. doi: 10.1126/science.1231143. Epub Jan. 3, 2013.
Cradick et al., CRISPR/Cas9 systems targeting 13-globin and CCR5 genes have substantial off-target activity. Nucleic Acids Res. Nov. 1, 2013;41(20):9584-92. doi: 10.1093/nar/gkt714. Epub Aug. 11, 2013.
De Souza, Primer: genome editing with engineered nucleases. Nat Methods. Jan. 2012;9(1):27.
Deltcheva et al., CRISPR RNA maturation by trans-encoded small RNA and host factor RNase III. Nature. Mar. 31, 2011;471(7340):602-7. doi: 10.1038/nature09886.
Dicarlo et al., Genome engineering in *Saccharomyces cerevisiae* using CRISPR-Cas systems. Nucleic Acids Res. Apr. 2013;41(7):4336-43. doi: 10.1093/nar/gkt135. Epub Mar. 4, 2013.
Dixon et al., Reengineering orthogonally selective riboswitches. Proc Natl Acad Sci USA. Feb. 16, 2010;107(7):2830-5. doi: 10.1073/pnas.0911209107. Epub Jan. 26, 2010.
Edwards et al., Crystal structures of the thi-box riboswitch bound to thiamine pyrophosphate analogs reveal adaptive RNA-small molecule recognition. Structure. Sep. 2006;14(9):1459-68.
Edwards et al., Structural basis for recognition of S-adenosylhomocysteine by riboswitches. RNA. Nov. 2010;16(11):2144-55. doi:10.1261/rna.2341610. Epub Sep. 23, 2010.
Ellington et al., In vitro selection of RNA molecules that bind specific ligands. Nature. Aug. 30, 1990;346(6287):818-22.
Esvelt et al., A system for the continuous directed evolution of biomolecules. Nature. Apr. 28, 2011;472(7344):499-503. doi: 10.1038/nature09929. Epub Apr. 10, 2011.
Esvelt et al., Genome-scale engineering for systems and synthetic biology. Mol Syst Biol. 2013;9:641. doi: 10.1038/msb.2012.66.
Esvelt et al., Orthogonal Cas9 proteins for RNA-guided gene regulation and editing. Nat Methods. Nov. 2013;10(11):1116-21. doi: 10.1038/nmeth.2681. Epub Sep. 29, 2013.
Fu et al., Improving CRISPR-Cas nuclease specificity using truncated guide RNAs. Nat Biotechnol. Mar. 2014;32(3):279-84. doi: 10.1038/nbt.2808. Epub Jan. 26, 2014.
Fu et al., High-frequency off-target mutagenesis induced by CRISPR-Cas nucleases in human cells. Nat Biotechnol. Sep. 2013;31(9):822-6. doi: 10.1038/nbt.2623. Epub Jun. 23, 2013.
Gaj et al., ZFN, TALEN, and CRISPR/Cas-based methods for genome engineering. Trends Biotechnol. Jul. 2013;31(7):397-405. doi: 10.1016/j.tibtech.2013.04.004. Epub May 9, 2013.
Gasiunas et al., Cas9-crRNA ribonucleoprotein complex mediates specific DNA cleavage for adaptive immunity in bacteria. Proc Natl Acad Sci USA. Sep. 25, 2012;109(39):E2579-86. Epub Sep. 4, 2012. Supplementary materials included.
Gasiunas et al., RNA-dependent DNA endonuclease Cas9 of the CRISPR system: Holy Grail of genome editing? Trends Microbiol. Nov. 2013;21(11):562-7. doi: 10.1016/j.tim.2013.09.001. Epub Oct. 1, 2013.
Gerber et al., RNA editing by base deamination: more enzymes, more targets, new mysteries. Trends Biochem Sci. Jun. 2001;26(6):376-84.
Gilbert et al., CRISPR-mediated modular RNA-guided regulation of transcription in eukaryotes. Cell. 2013 154(2):442-51.
Grundy et al., The L box regulon: lysine sensing by leader RNAs of bacterial lysine biosynthesis genes. Proc Natl Acad Sci USA. Oct. 14, 2003;100(21):12057-62. Epub Oct. 1, 2003.
Guilinger et al., Fusion of catalytically inactive Cas9 to FokI nuclease improves the specificity of genome modification. Nat Biotechnol. Jun. 2014;32(6):577-82. doi: 10.1038/nbt.2909. Epub Apr. 25, 2014.
Hale et al., RNA-guided RNA cleavage by a CRISPR RNA-Cas protein complex. Cell. Nov. 25, 2009;139(5):945-56. doi: 10.1016/j.cell.2009.07.040.
Hampel et al., Evidence for preorganization of the glmS ribozyme ligand binding pocket. Biochemistry. 2006; 45(25):7861-71.
Horvath et al., CRISPR/Cas, the immune system of bacteria and archaea. Science. Jan. 8, 2010;327(5962):167-70. doi: 10.1126/science.1179555.
Hsu et al., DNA targeting specificity of RNA-guided Cas9 nucleases. Nat Biotechnol. Sep. 2013;31(9):827-32. doi: 10.1038/nbt.2647. Epub Jul. 21, 2013.
Huang et al., Long-range pseudoknot interactions dictate the regulatory response in the tetrahydrofolate riboswitch. Proc Natl Acad Sci USA. Sep. 6, 2011;108(36):14801-6. doi: 10.1073/pnas.1111701108. Epub Aug. 22, 2011.
Humbert et al., Targeted gene therapies: tools, applications, optimization. Crit Rev Biochem Mol Biol. May-Jun. 2012;47(3):264-81. doi: 10.3109/10409238.2012.658112.
Hurt et al., Highly specific zinc finger proteins obtained by directed domain shuffling and cell-based selection. Proc Natl Acad Sci U S A. Oct. 14, 2003;100(21):12271-6. Epub Oct. 3, 2003.
Hwang et al., Efficient genome editing in zebrafish using a CRISPR-Cas system. Nat Biotechnol. Mar. 2013;31(3):227-9. doi: 10.1038/nbt.2501. Epub Jan. 29, 2013.

(56) References Cited

OTHER PUBLICATIONS

Jansen et al., Backbone and nucleobase contacts to glucosamine-6-phosphate in the glmS ribozyme. Nat Struct Mol Biol. Jun. 2006;13(6):517-23. Epub May 14, 2006.

Jenkins et al., Comparison of a preQ1 riboswitch aptamer in metabolite-bound and free states with implications for gene regulation. J Biol Chem. Jul. 15, 2011;286(28):24626-37. doi: 10.1074/jbc.M111.230375. Epub May 18, 2011.

Jiang et al., RNA-guided editing of bacterial genomes using CRISPR-Cas systems. Nat Biotechnol. Mar. 2013;31(3):233-9. doi: 10.1038/nbt.2508. Epub Jan. 29, 2013.

Jinek et al., A programmable dual-RNA-guided DNA endonuclease in adaptive bacterial immunity. Science. Aug. 17, 2012;337(6096):816-21. doi: 10.1126/science.1225829. Epub Jun. 28, 2012.

Jinek et al., RNA-programmed genome editing in human cells. Elife. Jan. 29, 2013;2:e00471. doi: 10.7554/eLife.00471.

Jinek et al., Structures of Cas9 endonucleases reveal RNA-mediated conformational activation. Science. Mar. 14, 2014;343(6176):1247997. doi: 10.1126/science.1247997. Epub Feb. 6, 2014.

Jore et al., Structural basis for CRISPR RNA-guided DNA recognition by Cascade. Nat Struct Mol Biol. May 2011;18(5):529-36. doi: 10.1038/nsmb.2019. Epub Apr. 3, 2011.

Kang et al., Structural Insights into riboswitch control of the biosynthesis of queuosine, a modified nucleotide found in the anticodon of tRNA. Mol Cell. Mar. 27, 2009;33(6):784-90. doi: 10.1016/j.molcel.2009.02.019. Epub Mar. 12, 2009.

Kim et al., Highly efficient RNA-guided genome editing in human cells via delivery of purified Cas9 ribonucleoproteins. Genome Res. Jun. 2014;24(6):1012-9. doi: 10.1101/gr.171322.113. Epub Apr. 2, 2014.

Klein et al., Cocrystal structure of a class I preQ1 riboswitch reveals a pseudoknot recognizing an essential hypermodified nucleobase. Nat Struct Mol Biol. Mar. 2009;16(3):343-4. doi: 10.1038/nsmb.1563.Epub Feb. 22, 2009.

Kwon et al., Chemical basis of glycine riboswitch cooperativity. RNA. Jan. 2008;14(1):25-34. Epub Nov. 27, 2007.

Larson et al., CRISPR interference (CRISPRi) for sequence-specific control of gene expression. Nat Protoc. Nov. 2013;8(11):2180-96. doi: 10.1038/nprot.2013.132. Epub Oct. 17, 2013.

Lee et al., An allosteric self-splicing ribozyme triggered by a bacterial second messenger. Science. Aug. 13, 2010;329(5993):845-8. doi: 10.1126/science.1190713.

Maeder et al., CRISPR RNA-guided activation of endogenous human genes. Nat Methods. Oct. 2013;10(10):977-9. doi: 10.1038/nmeth.2598. Epub Jul. 25, 2013.

Mali et al., Cas9 as a versatile tool for engineeringbiology. Nat Methods. Oct. 2013;10(10):957-63. doi: 10.1038/nmeth.2649.

Mali et al., CAS9 transcriptional activators for target specificity screening and paired nickases for cooperative genome engineering. Nat Biotechnol. Sep. 2013;31(9):833-8. doi: 10.1038/nbt.2675. Epub Aug. 1, 2013.

Mali et al., RNA-guided human genome engineering via Cas9. Science. Feb. 15, 2013;339(6121):823-6. doi: 10.1126/science.1232033. Epub Jan. 3, 2013.

Mandal et al., A glycine-dependent riboswitch that uses cooperative binding to control gene expression. Science. Oct. 8, 2004;306(5694):275-9.

Mandal et al., Adenine riboswitches and gene activation by disruption of a transcription terminator. Nat Struct Mol Biol. Jan. 2004;11(1):29-35. Epub Dec. 29, 2003.

Meyer et al., Confirmation of a second natural preQ1 aptamer class in Streptococcaceae bacteria. RNA. Apr. 2008;14(4):685-95. doi: 10.1261/rna.937308. Epub Feb. 27, 2008.

Montange et al., Structure of the S-adenosylmethionine riboswitch regulatory mRNA element. Nature. Jun. 29, 2006;441(7097):1172-5.

Mootz et al., Conditional protein splicing: a new tool to control protein structure and function in vitro and in vivo. J Am Chem Soc. Sep. 3, 2003;125(35):10561-9.

Mootz et al., Protein splicing triggered by a small molecule. J Am Chem Soc. Aug. 7, 2002;124(31):9044-5.

Nahvi et al., Coenzyme $B_{12}$ riboswitches are widespread genetic control elements in prokaryotes. Nucleic Acids Res. Jan. 2, 2004;32(1):143-50.

Narayanan et al., Clamping down on weak terminal base pairs: oligonucleotides with molecular caps as fidelity-enhancing elements at the 5'- and 3'-terminal residues. Nucleic Acids Res. May 20, 2004;32(9):2901-11. Print 2004.

Neel et al., Riboswitches: Classification, function and in silico approach, International Journal of Pharma Sciences and Research. 2010;1(9):409-420.

Ni et al., Nucleic acid aptamers: clinical applications and promising new horizons. Curr Med Chem. 2011;18(27):4206-14. Review.

Nishimasu et al., Crystal structure of Cas9 in complex with guide RNA and target DNA. Cell. Feb. 27, 2014;156(5):935-49. doi: 10.1016/j.cell.2014.02.001. Epub Feb. 13, 2014.

Pan et al., Biological and biomedical applications of engineered nucleases. Mol Biotechnol. Sep. 2013;55(1):54-62. doi: 10.1007/s12033-012-9613-9.

Pattanayak et al., High-throughput profiling of off-target DNA cleavage reveals RNA-programmed Cas9 nuclease specificity. Nat Biotechnol. Sep. 2013;31(9):839-43. doi: 10.1038/nbt.2673. Epub Aug. 11, 2013.

Peck et al., Directed evolution of a small-molecule-triggered intein with improved splicing properties in mammalian cells. Chem Biol. May 27, 2011;18(5):619-30. doi: 10.1016/j.chembiol.2011.02.014.

Pennisi et al., The CRISPR craze. Science. Aug. 23, 2013;341(6148):833-6. doi: 10.1126/science.341.6148.833.

Pennisi et al., The tale of the TALEs. Science. Dec. 14, 2012;338(6113):1408-11. doi: 10.1126/science.338.6113.1408.

Perez-Pinera et al., Advances in targeted genome editing. Curr Opin Chem Biol. Aug. 2012;16(3-4):268-77. doi: 10.1016/j.cbpa.2012.06.007. Epub Jul. 20, 2012.

Perez-Pinera et al., RNA-guided gene activation by CRISPR-Cas9-based transcription factors. Nat Methods. Oct. 2013;10(10):973-6. doi: 10.1038/nmeth.2600. Epub Jul. 25, 2013.

Porteus, Design and testing of zinc finger nucleases for use in mammalian cells. Methods Mol Biol. 2008;435:47-61. doi: 10.1007/978-1-59745-232-8_4.

Qi et al., Repurposing CRISPR as an RNA-guided platform for sequence-specific control of gene expression. Cell. Feb. 28, 2013;152(5):1173-83. doi: 10.1016/j.cell.2013.02.022.

Ran et al., Double nicking by RNA-guided CRISPR Cas9 for enhanced genome editing specificity. Cell. Sep. 12, 2013;154(6):1380-9. doi: 10.1016/j.cell.2013.08.021. Epub Aug. 29, 2013.

Roth et al., A riboswitch selective for the queuosine precursor preQ1 contains an unusually small aptamer domain. Nat Struct Mol Biol. Apr. 2007;14(4):308-17. Epub Mar. 25, 2007.

Sander et al., CRISPR-Cas systems for editing, regulating and targeting genomes. Nat Biotechnol. Apr. 2014;32(4):347-55. doi: 10.1038/nbt.2842. Epub Mar. 2, 2014.

Sapranauskas et al., The *Streptococcus thermophilus* CRISPR/Cas system provides immunity in *Escherichia coli*. Nucleic Acids Res. Nov. 2011;39(21):9275-82. doi: 10.1093/nar/gkr606. Epub Aug. 3, 2011.

Sashital et al., Mechanism of foreign DNA selection in a bacterial adaptive immune system. Mol Cell. Jun. 8, 2012;46(5):606-15. doi: 10.1016/j.molcel.2012.03.020. Epub Apr. 19, 2012.

Schwank et al., Functional repair of CFTR by CRISPR/Cas9 in intestinal stem cell organoids of cystic fibrosis patients. Cell Stem Cell. Dec. 5, 2013;13(6):653-8. doi:10.1016/j.stem.2013.11.002.

Schriefer et al., Low pressure DNA shearing: a method for random DNA sequence analysis. Nucleic Acids Res. Dec. 25, 1990;18(24):7455-6.

Semenova et al., Interference by clustered regularly interspaced short palindromic repeat (CRISPR) RNA is governed by a seed sequence. Proc Natl Acad Sci USA. Jun. 21, 2011;108(25):10098-103. doi: 10.1073/pnas.1104144108. Epub Jun. 6, 2011.

(56) References Cited

OTHER PUBLICATIONS

Serganov et al., Coenzyme recognition and gene regulation by a flavin mononucleotide riboswitch. Nature. Mar. 12, 2009;458(7235):233-7. doi: 10.1038/nature07642. Epub Jan. 25, 2009.
Serganov et al., Structural basis for discriminative regulation of gene expression by adenine-and guanine-sensing mRNAs. Chem Biol. Dec. 2004;11(12):1729-41.
Serganov et al., Structural basis for gene regulation by a thiamine pyrophosphate-sensing riboswitch. Nature. Jun. 29, 2006;441(7097):1167-71. Epub May 21, 2006.
Shalem et al., Genome-scale CRISPR-Cas9 knockout screening in human cells. Science. Jan. 3, 2014;343(6166):84-7. doi: 10.1126/science.1247005. Epub Dec. 12, 2013.
Sheridan, First CRISPR-Cas patent opens race to stake out intellectual property. Nat Biotechnol. 2014;32(7):599-601.
Sheridan, Gene therapy finds its niche. Nat Biotechnol. Feb. 2011;29(2):121-8. doi: 10.1038/nbt.1769.
Siebert et al., An improved PCR method for walking in uncloned genomic DNA. Nucleic Acids Res. Mar. 25, 1995;23(6):1087-8.
Sudarsan et al., an mRNA structure in bacteria that controls gene expression by binding lysine. Genes Dev. Nov. 1, 2003;17(21):2688-97.
Sudarsan et al., Riboswitches in eubacteria sense the second messenger cyclic di-GMP. Science. Jul. 18, 2008;321(5887):411-3. doi: 10.1126/science.1159519.
Suess et al., A theophylline responsive riboswitch based on helix slipping controls gene expression in vivo. Nucleic Acids Res. Mar. 5, 2004;32(4):1610-4.
Trausch et al., The structure of a tetrahydrofolate-sensing riboswitch reveals two ligand binding sites in a single aptamer. Structure. Oct. 12, 2011;19(10):1413-23. doi: 10.1016/j.str.2011.06.019. Epub Sep. 8, 2011.
Tsai et al., Dimeric CRISPR RNA-guided FokI nucleases for highly specific genome editing. Nat Biotechnol. Jun. 2014;32(6):569-76. doi: 10.1038/nbt.2908. Epub Apr. 25, 2014.
Vitreschak et al., Regulation of the vitamin B12 metabolism and transport in bacteria by a conserved RNA structural element. RNA. Sep. 2003;9(9):1084-97.
Wang et al., Genetic screens in human cells using the CRISPR-Cas9 system. Science. Jan. 3, 2014;343(6166):80-4. doi: 10.1126/science.1246981. Epub Dec. 12, 2013.
Wang et al., One-step generation of mice carrying mutations in multiple genes by CRISPR/Cas-mediated genome engineering. Cell. May 9, 2013;153(4):910-8. doi: 10.1016/j.cell.2013.04.025. Epub May 2, 2013.
Wang et al., Riboswitches that sense S-adenosylhomocysteine and activate genes involved in coenzyme recycling. Mol Cell. Mar. 28, 2008;29(6):691-702. doi: 10.1016/j.molcel.2008.01.012.
Weinberg et al., The aptamer core of SAM-IV riboswitches mimics the ligand-binding site of SAM-I riboswitches. RNA. May 2008;14(5):822-8. doi: 10.1261/rna.988608. Epub Mar. 27, 2008.
Wiedenheft et al., RNA-guided genetic silencing systems in bacteria and archaea. Nature. Feb. 15, 2012;482(7385):331-8. doi: 10.1038/nature10886. Review.
Winkler et al., An mRNA structure that controls gene expression by binding FMN. Proc Natl Acad Sci USA. Dec. 10, 2002;99(25):15908-13. Epub Nov. 27, 2002.
Winkler et al., An mRNA structure that controls gene expression by binding S-adenosylmethionine. Nat Struct Biol. Sep. 2003;10(9):701-7. Epub Aug. 10, 2003.
Winkler et al., Control of gene expression by a natural metabolite-responsive ribozyme. Nature. Mar. 18, 2004;428(6980):281-6.
Winkler et al., Thiamine derivatives bind messenger RNAs directly to regulate bacterial gene expression. Nature. Oct. 31, 2002;419(6910):952-6. Epub Oct. 16, 2002.
Wu et al., Correction of a genetic disease in mouse via use of CRISPR-Cas9. Cell Stem Cell. Dec. 5, 2013;13(6):659-62. doi: 10.1016/j.stem.2013.10.016.
Yin et al., Genome editing with Cas9 in adult mice corrects a disease mutation and phenotype. Nat Biotechnol. Jun. 2014;32(6):551-3. doi: 10.1038/nbt.2884. Epub Mar. 30, 2014.
Zhang et al., Conditional gene manipulation: Cre-ating a new biological era. J Zhejiang Univ Sci B. Jul. 2012;13(7):511-24. doi: 10.1631/jzus.B1200042. Review.
Zimmermann et al., Molecular interactions and metal binding in the theophylline-binding core of an RNA aptamer. RNA. May, 2000;6(5):659-67.
Partial Supplementary European Search Report for Application No. EP 12845790.0, mailed Mar. 18, 2015.
International Search Report and Written Opinion for PCT/US2014/052231, mailed Jan. 30, 2015 (Corrected Version).
International Search Report and Written Opinion for PCT/US2014/054247, mailed Mar. 27, 2015.
International Search Report and Written Opinion for PCT/US2014/054291, mailed Mar. 27, 2015.
International Search Report and Written Opinion for PCT/US2014/054252, mailed Mar. 5, 2015.
International Search Report and Written Opinion for PCT/US2014/070038, mailed Apr. 14, 2015.
Boeckle et al., Melittin analogs with high lytic activity at endosomal pH enhance transfection with purified targeted PEI polyplexes. J Control Release. May 15, 2006;112(2):240-8. Epub Mar. 20, 2006.
Branden and Tooze, Introduction to Protein Structure. 1999; 2nd edition. Garland Science Publisher: 3-12.
Caron et al., Intracellular delivery of a Tat-eGFP fusion protein into muscle cells. Mol Ther. Mar. 2001;3(3):310-8.
Chung-Il et al., Artificial control of gene expression in mammalian cells by modulating RNA interference through aptamer-small molecule interaction. RNA. May 2006;12(5):710-6. Epub Apr. 10, 2006.
Cradick et al., ZFN-site searches genomes for zinc finger nuclease target sites and off-target sites. BMC Bioinformatics. May 13, 2011;12:152. doi: 10.1186/1471-2105-12-152.
Gilleron et al., Image-based analysis of lipid nanoparticle-mediated siRNA delivery, intracellular trafficking and endosomal escape. Nat Biotechnol. Jul. 2013;31(7):638-46. doi: 10.1038/nbt.2612. Epub Jun. 23, 2013.
Guo et al., Protein tolerance to random amino acid change. J Gene Med. Mar.-Apr. 2002;4(2):195-204.
Hasadsri et al., Functional protein delivery into neurons using polymeric nanoparticles. J Biol Chem. Mar. 13, 2009;284(11):6972-81. doi: 10.1074/jbc.M805956200. Epub Jan. 7, 2009.
Hill et al., Functional analysis of conserved histidines in ADP-glucose pyrophosphorylase from *Escherichia coli*.Biochem Biophys Res Commun. Mar. 17, 1998;244(2):573-7.
Klauser et al., An engineered small RNA-mediated genetic switch based on a ribozyme expression platform. Nucleic Acids Res. May 1, 2014;41(10):5542-52. doi: 10.1093/nar/gkt253. Epub Apr. 12, 2013.
Lazar et al., Transforming growth factor alpha: mutation of aspartic acid 47 and leucine 48 results in different biological activities. Mol Cell Biol. Mar. 1988;8(3):1247-52.
Lewis et al., A serum-resistant cytofectin for cellular delivery of antisense oligodeoxynucleotides and plasmid DNA. Proc Natl Acad Sci U S A. Apr. 16, 1996;93(8):3176-81.
Lundberg et al., Delivery of short interfering RNA using endosomolytic cell-penetrating peptides. Faseb J. Sep. 2007;21(11):2664-71. Epub Apr. 26, 2007.
Nomura et al., Synthetic mammalian riboswitches based on guanine aptazyme. Chem Commun.(Camb). Jul. 21, 2012;48(57):7215-7. doi: 10.1039/c2cc33140c. Epub Jun. 13, 2012.
Pattanayak et al., Determining the specificities of TALENs, Cas9, and other genome-editing.enzymes. Methods Enzymol. 2014;546:47-78. doi: 10.1016/B978-0-12-801185-0.00003-9.
Qi et al., Engineering naturally occuring trans-acting non-coding RNAs to sense molecular signals. Nucleic Acids Res. Jul. 2012;40(12):5775-86. doi: 10.1093/nar/gks168. Epub Mar. 1, 2012.
Ramakrishna et al., Gene disruption by cell-penetrating peptide-mediated delivery of Cas9 protein and guide RNA. Genome Res. Jun. 2014;24(6):1020-7. doi: 10.1101/gr.171264.113. Epub Apr. 2, 2014.
Samal et al., Cationic polymers and their therapeutic potential. Chem Soc Rev. Nov. 7, 2012;41(21):7147-94. doi: 10.1039/c2cs35094g. Epub Aug. 10, 2012.

(56) References Cited

OTHER PUBLICATIONS

Sang, Prospects for transgenesis in the chick. Mech Dev. Sep. 2004;121(9):1179-86.

Schwarze et al., In vivo protein transduction: delivery of a biologically active protein into the mouse. Science. Sep. 3, 1999;285(5433):1569-72.

Sells et al., Delivery of protein into cells using polycationic liposomes. Biotechniques. Jul. 1995;19(1):72-6, 78.

Thorpe et al., Functional correction of episomal mutations with short DNA fragments and RNA-DNA oligonucleotides. J Gene Med. Mar.-Apr. 2002;4(2):195-204.

Wacey et al., Disentangling the perturbational effects of amino acid substitutions in the DNA-binding domain of p53. Hum Genet. Jan. 1999;104(1):15-22.

Wadia et al., Modulation of cellular function by TAT mediated transduction of full length proteins. Curr Protein Pept Sci. Apr. 2003;4(2):97-104.

Wadia et al., Transducible TAT-HA fusogenic peptide enhances escape of TAT-fusion proteins after lipid raft macropinocytosis. Nat Med. Mar. 2004;10(3):310-5. Epub Feb. 8, 2004.

Supplementary European Search Report for Application No. EP 12845790.0, mailed Oct. 12, 2015.

Uniprot Submission; UniProt, Accession No. P01011. Last modified Sep. 18, 2013, version 2. 15 pages.

No Author Listed, EMBL Accession No. Q99ZW2. Nov. 2012. 2 pages.

No Author Listed, Thermo Fisher Scientific—How Cationic Lipid Mediated Transfection Works, retrieved from the internet Aug. 27, 2015. 2 pages.

No Author Listed, Invitrogen Lipofectamine™ 2000 product sheets, 2002. 2 pages.

No Author Listed, Invitrogen Lipofectamine™ 2000 product sheets, 2005. 3 pages.

No Author Listed, Invitrogen Lipofectamine™ LTX product sheets, 2011. 4 pages.

Alexandrov et al., Signatures of mutational processes in human cancer. Nature. Aug. 22, 2013;500(7463):415-21. doi: 10.1038/nature12477. Epub Aug. 14, 2013.

Cameron, Recent advances in transgenic technology. Mol Biotechnol. Jun. 1997;7(3):253-65.

Houdebine, The methods to generate transgenic animals and to control transgene expression. J Biotechnol. Sep. 25, 2002;98(2-3):145-60.

Kappel et al., Regulating gene expression in transgenic animals. Curr Opin Biotechnol. Oct. 1992;3(5):548-53.

Mullins et al., Transgenesis in nonmurine species. Hypertension. Oct. 1993;22(4):630-3.

Phillips, The challenge of gene therapy and DNA delivery. J Pharm Pharmacol. Sep. 2001;53(9):1169-74.

\* cited by examiner gRNA 5' xDNA sensing, Off State

```
5'- ─── GGCAGAGATGTAGTGTTTCCACAGGG ─── ─── 3'
3'- ─── CCGTCTCTACATCACAAAGGTGTCCC ─── ─── 5'
```

FIG. 3A

EXTENDED DNA-SENSING GRNAS

RELATED APPLICATIONS

This application claims priority under 35 U.S.C. §119(e) to U.S. provisional application, U.S. Ser. No. 61/874,682, filed Sep. 6, 2013, which is incorporated herein by reference.

BACKGROUND OF THE INVENTION

Site-specific endonucleases theoretically allow for the targeted manipulation of a single site within a genome and are useful in the context of gene targeting as well as for therapeutic applications. In a variety of organisms, including mammals, site-specific endonucleases have been used for genome engineering by stimulating either non-homologous end joining or homologous recombination. In addition to providing powerful research tools, site-specific nucleases also have potential as gene therapy agents, and two site-specific endonucleases have recently entered clinical trials: one, CCR5-2246, targeting a human CCR-5 allele as part of an anti-HIV therapeutic approach (NCT00842634, NCT01044654, NCT01252641), and the other one, VF24684, targeting the human VEGF-A promoter as part of an anti-cancer therapeutic approach (NCT01082926).

Specific cleavage of the intended nuclease target site without or with only minimal off-target activity is a prerequisite for clinical applications of site-specific endonuclease, and also for high-efficiency genomic manipulations in basic research applications. For example, imperfect specificity of engineered site-specific binding domains has been linked to cellular toxicity and undesired alterations of genomic loci other than the intended target. Most nucleases available today, however, exhibit significant off-target activity, and thus may not be suitable for clinical applications. An emerging nuclease platform for use in clinical and research settings are the RNA-guided nucleases, such as Cas9. While these nucleases are able to bind guide RNAs (gRNAs) that direct cleavage of specific target sites, off-target activity is still observed for certain Cas9:gRNA complexes (Pattanayak et al., "High-throughput profiling of off-target DNA cleavage reveals RNA-programmed Cas9 nuclease specificity." *Nat Biotechnol.* 2013; doi: 10.1038/nbt.2673). Technology for engineering nucleases with improved specificity is therefore needed.

SUMMARY OF THE INVENTION

Some aspects of this disclosure are based on the recognition that the reported toxicity of some engineered site-specific endonucleases is based on off-target DNA cleavage. Further, the activity of existing RNA-guided nucleases generally cannot be controlled at the molecular level, for example, to switch a nuclease from an "off" to an "on" state. Controlling the activity of nucleases could decrease the likelihood of incurring off-target effects. Some aspects of this disclosure provide strategies, compositions, systems, and methods to control the binding and/or cleavage activity RNA-programmable endonucleases, such as Cas9 endonuclease.

Accordingly, one embodiment of the disclosure provides RNA-guided nuclease complexes comprising a "switchable" guide RNA (gRNA). For example, in some embodiments, the invention provides a complex comprising: (i) a gRNA comprising an aptamer, wherein the gRNA does not hybridize to a target nucleic acid in the absence of a specific ligand bound to the aptamer; and (ii) a Cas9 protein. In some embodiments, the aptamer is bound by a ligand. In some aspects, the ligand is any molecule. In some aspects, the ligand is a small molecule, a metabolite, a carbohydrate, a peptide, a protein, or a nucleic acid. In some embodiments, the gRNA:ligand:Cas9 complex binds to and mediates cleavage of a target nucleic acid. See, e.g., FIG. 1.

According to another embodiment, gRNAs comprising an aptamer are provided. In some embodiments, the gRNA does not hybridize to a target nucleic acid in the absence of a ligand bound to the aptamer. Such gRNAs may be referred to as "switchable gRNAs." For example, in some aspects, the gRNA does not bind Cas9 in the absence of a ligand bound to the aptamer. See, e.g., FIGS. 1A-B. In some embodiments, the gRNA binds Cas9 when the aptamer is bound by a ligand specific to the aptamer. In some embodiments, the gRNA binds Cas9 in the absence or presence of a ligand bound to the aptamer but binds to a target nucleic acid only in the presence of a ligand bound to the aptamer. In some aspects, the ligand is any molecule. In some aspects, the ligand is a small molecule, a metabolite, a carbohydrate, a peptide, a protein, or a nucleic acid. In some embodiments, the aptamer is an RNA aptamer, for example, an RNA aptamer derived from a riboswitch. In some embodiments, the riboswitch from which the aptamer is derived is selected from a theophylline riboswitch, a thiamine pyrophosphate (TPP) riboswitch, an adenosine cobalamin (AdoCbl) riboswitch, an S-adenosyl methionine (SAM) riboswitch, an SAH riboswitch, a flavin mononucleotide (FMN) riboswitch, a tetrahydrofolate riboswitch, a lysine riboswitch, a glycine riboswitch, a purine riboswitch, a GlmS riboswitch, or a pre-queosine$_1$ (PreQ1) riboswitch. In some embodiments, the aptamer is derived from a theophylline riboswitch and comprises SEQ ID NO:3. In other embodiments, the aptamer is non-naturally occurring, and in some aspects, is engineered to bind a specific ligand using a systematic evolution of ligands by exponential enrichment (SELEX) platform. In some embodiments, the non-aptamer portion of the gRNA comprises at least 50, at least 60, at least 70, at least 80, at least 90, at least 100, at least 110, at least 120, at least 130, at least 140, or at least 150 nucleotides, and the aptamer comprises at least 20, at least 30, at least 40, at least 50, at least 60, at least 70, at least 80, at least 90, at least 100, at least 110, at least 120, at least 130, at least 140, at least 150, at least 175, at least 200, at least 250, or at least 300 nucleotides.

According to another embodiment, methods for site-specific DNA cleavage using the inventive Cas9 variants are provided. For example, in some aspects, the methods comprise contacting a DNA with a complex comprising (i) a gRNA comprising an aptamer, wherein the gRNA comprises a sequence that binds to a portion of the DNA, (ii) a specific ligand bound to the aptamer of the gRNA, and (iii) a Cas9 protein, under conditions in which the Cas9 protein cleaves the DNA.

According to another embodiment, methods for inducing site-specific DNA cleavage in a cell are provided. For example, in some embodiments, the methods comprise: (a) contacting a cell or expressing within a cell a gRNA comprising an aptamer, wherein the gRNA comprises a sequence capable of binding to a DNA target sequence; (b) contacting a cell or expressing within a cell a Cas9 protein; and (c) contacting the cell with a ligand that binds the aptamer of the gRNA, resulting in the formation of a gRNA:ligand:Cas9 complex that cleaves the DNA target. In some embodiments, the cell produces the ligand intracellularly, for example as a part of physiological or pathophysiological process. In some embodiments, the method comprises (a) contacting the cell with a complex comprising a Cas9 protein and a gRNA comprising an aptamer, wherein the gRNA comprises a sequence capable of binding to a DNA target sequence; and (b) contacting the cell with a ligand that binds the aptamer of the gRNA, resulting in the formation of a gRNA:ligand:Cas9 complex that cleaves the DNA target. In some aspects, steps (a) and (b) are performed simultaneously or sequentially in any order. In some embodiments, the method is performed in vitro, whereas in other embodiments the method is performed in vivo.

According to another embodiment, RNA-guided nuclease complexes comprising an mRNA-sensing gRNA are provided. For example, in some embodiments, the complex comprises a Cas9 protein and a gRNA, wherein the gRNA comprises: (i) a region that hybridizes a region of a target nucleic acid; (ii) another region that partially or completely hybridizes to the sequence of region (i); and (iii) a region that hybridizes to a region of a transcript (mRNA).

According to another embodiment, mRNA-sensing gRNAs are provided, for example, that comprise: (i) a region that hybridizes a region of a target nucleic acid; (ii) another region that partially or completely hybridizes to the sequence of region (i); and (iii) a region that hybridizes to a region of a transcript (mRNA). See, e.g., FIG. 2. In some embodiments, each of the sequences of regions (i), (ii), and (iii) comprise at least 5, at least 10, at least 15, at least 20, or at least 25 nucleotides. In some aspects, the gRNA forms a stem-loop structure in which the stem comprises the sequence of region (i) hybridized to part or all of the sequence of region (ii), and the loop is formed by part or all of the sequence of region (iii). In some embodiments, regions (ii) and (iii) are both either 5' or 3' to region (i). See, e.g., FIG. 2A vs. FIG. 2C. In some embodiments, the stem-loop structure forms in the absence of the transcript that hybridizes to the sequence of region (iii). In this example, the gRNA is said to be in the "off" state. See, e.g., FIG. 2A, 2C. In some embodiments, the binding of the transcript to the sequence of region (iii) results in the unfolding of the stem-loop structure, or prevents the formation of the stem-loop structure, such that the sequence of region (ii) does not hybridize to the sequence of region (i). In this example, the gRNA is said to be in the "on" state. See, e.g., FIG. 2B, 2D. In some embodiments, the gRNA binds a Cas9 protein, and the sequence of region (i) hybridizes to the target nucleic acid when the sequence of region (iii) binds (e.g., "senses") the transcript.

According to another embodiment, methods for site specific DNA cleavage are provided, for example, that comprise contacting a DNA with the complex comprising a Cas9 protein associated with an mRNA-sensing gRNA, wherein the mRNA-sensing gRNA is bound by an mRNA thereby allowing the complex to bind and cleave the DNA.

According to another embodiment, extended DNA recognition (xDNA-sensing) gRNAs are provided. See, e.g., FIG. 3. In some embodiments, xDNA-sensing gRNAs comprise: (i) a region that hybridizes a region of a target nucleic acid; (ii) another region that partially or completely hybridizes to the sequence of region (i); and (iii) a region that hybridizes to another region of the target nucleic acid. In some embodiments, each of the sequences of regions (i) and (ii) comprise at least 5, at least 10, at least 15, at least 20, or at least 25 nucleotides; and the sequence of region (iii) comprise at least 5, at least 10, at least 15, at least 20, at least 25, at least 30, at least 40, at least 50, at least 75, or at least 100 nucleotides. In some embodiments, the gRNA forms a stem-loop structure in which the stem comprises the sequence of region (i) hybridized to part or all of the sequence of region (ii), and the loop is formed by part or all of the sequence of region (iii). In some embodiments, regions (ii) and (iii) are both either 5' or 3' to region (i). See e.g., FIG. 3A vs. FIG. 3C. In some embodiments, the stem-loop structure forms in the absence of the region of the target nucleic acid that complements and binds the sequence in region (iii). See, e.g., FIG. 3A, C. In some embodiments, the hybridization of the region of the target nucleic acid to the sequence of region (iii) results in the unfolding of the stem-loop structure, or prevents the formation of the stem-loop structure, such that the sequence of region (ii) does not hybridize to the sequence of region (i). See, e.g., FIG. 3B, D. In some embodiments, the gRNA binds a Cas9 protein, and the sequence in (i) binds the target nucleic acid when the sequence in region (iii) binds the target nucleic acid.

According to another embodiment, complexes comprising an xDNA-sensing gRNA and a Cas9 protein are provided, optionally wherein the complex comprises a target nucleic acid. In some embodiments, the formation of the complex results in the cleavage of the target nucleic acid.

According to another embodiment, methods for site-specific DNA cleavage are provided comprising contacting a DNA with the complex comprising an xDNA-sensing gRNA and a Cas9 protein.

Any of the methods provided herein can be performed on DNA in a cell, for example, a cell in vitro or in vivo. In some embodiments, any of the methods provided herein are performed on DNA in a eukaryotic cell. In some embodiments, the eukaryotic cell is in an individual, for example, a human.

According to another embodiment, polynucleotides are provided, for example, that encode any of the gRNAs, complexes, or proteins (e.g., Cas9 proteins) described herein. In some embodiments, vectors that comprise a polynucleotide described herein are provided. In some embodiments, vectors for recombinant expression of any of the gRNAs, complexes, or proteins (e.g., Cas9 proteins) described herein are provided. In some embodiments, cells comprising genetic constructs for expressing any of the gRNAs, complexes, or proteins (e.g., Cas9 proteins) described herein are provided.

In some embodiments, kits are provided. For example, kits comprising any of the gRNAs, complexes, or proteins (e.g., Cas9 proteins) described herein are provided. In some embodiments, kits comprising any of the polynucleotides described herein are provided. In some embodiments, kits comprising a vector for recombinant expression, wherein the vectors comprise a polynucleotide encoding any of the gRNAs, complexes, or proteins (e.g., Cas9 proteins) described herein, are provided. In some embodiments, kits comprising a cell comprising genetic constructs for expressing any of the gRNAs, complexes, or proteins (e.g., Cas9 proteins) described herein are provided.

Other advantages, features, and uses of the invention will be apparent from the Detailed Description of Certain Embodiments of the Invention; the Drawings, which are schematic and not intended to be drawn to scale; and the Claims.

DEFINITIONS

Figure 1A:
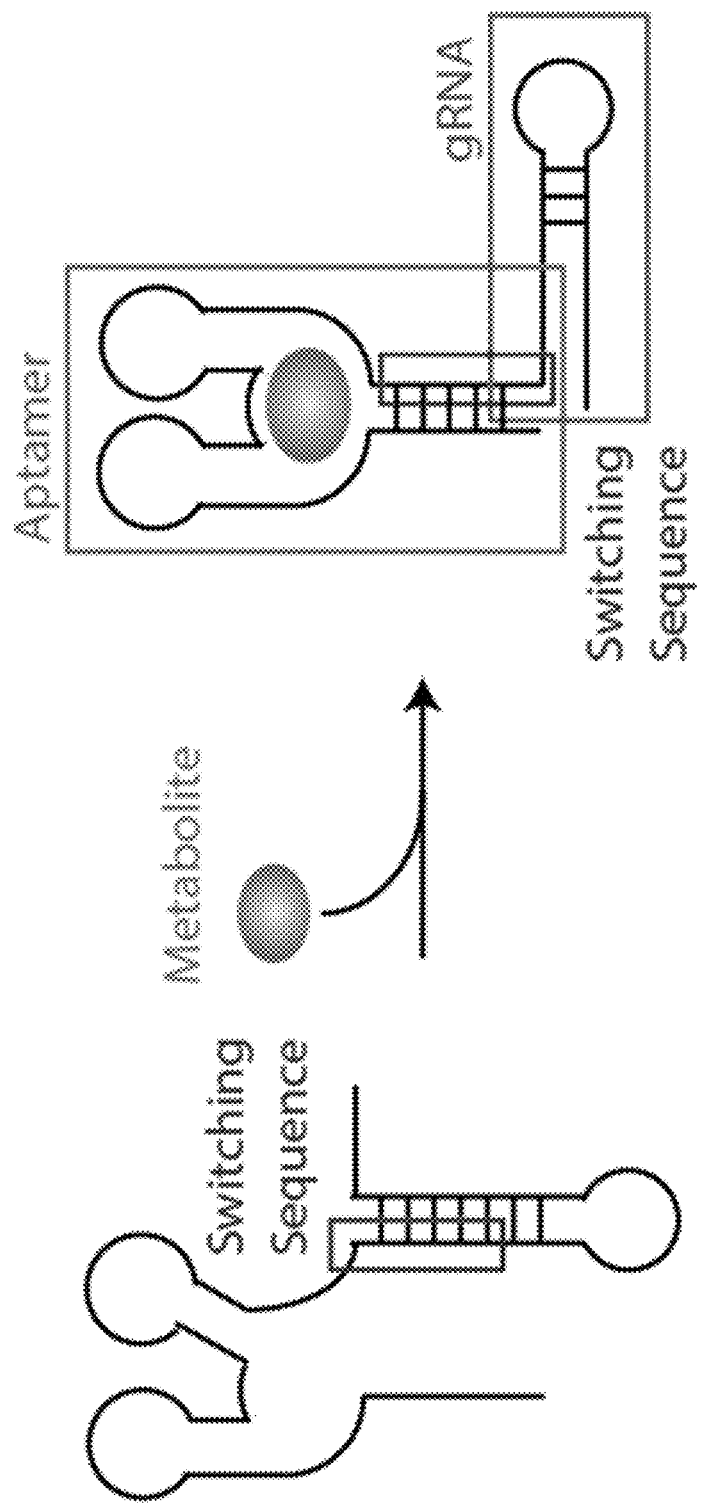
FIG. 1 shows certain embodiments of the invention relating to gRNAs linked to aptamers. (A) In this figure, a switchable gRNA comprising an aptamer is schematically depicted. In the absence of a specific ligand (here, a metabolite) that binds the aptamer, the sequence responsible for binding the target nucleic acid is hybridized to aspects of the aptamer (see far left, area depicted as "switching sequence"). Upon binding of the metabolite, the aptamer undergoes conformational changes, such that the sequence responsible for binding the target nucleic acid no longer hybridizes to the aptamer sequence, allowing it to hybridize to the target. (B) Upon switching to an "on" state, the gRNA, when bound to Cas9, directs the nuclease to the target site where it hybridizes to the target site, allowing Cas9 to cleave each strand of the target nucleic acid. (C-D) In this figure, the aptamer linked to a gRNA is derived from the theophylline riboswitch. In the absence of theophylline (C), aspects of the aptamer (depicted as "Theophylline Riboswitch") bind aspects of the sequence (depicted as "Guide to Cut the Target") responsible for binding the target nucleic acid (depicted by the double-stranded sequence at the top of the panel), thereby precluding the gRNA from hybridizing to the target nucleic acid. When aptamer is bound by theophylline (depicted as solid small molecule binding the aptamer sequence) (D), it undergoes conformational changes resulting in the "Guide" sequence being free to hybridize to the target nucleic acid. Sequence Identifiers: The target sequence at the top of FIGS. 1C and 1D from 5' to 3' is SEQ ID NO:4, and from 3' to 5' is SEQ ID NO:5. The gRNA shown in FIGS. 1C and 1D corresponds to SEQ ID NO:6.
Figure 1B:
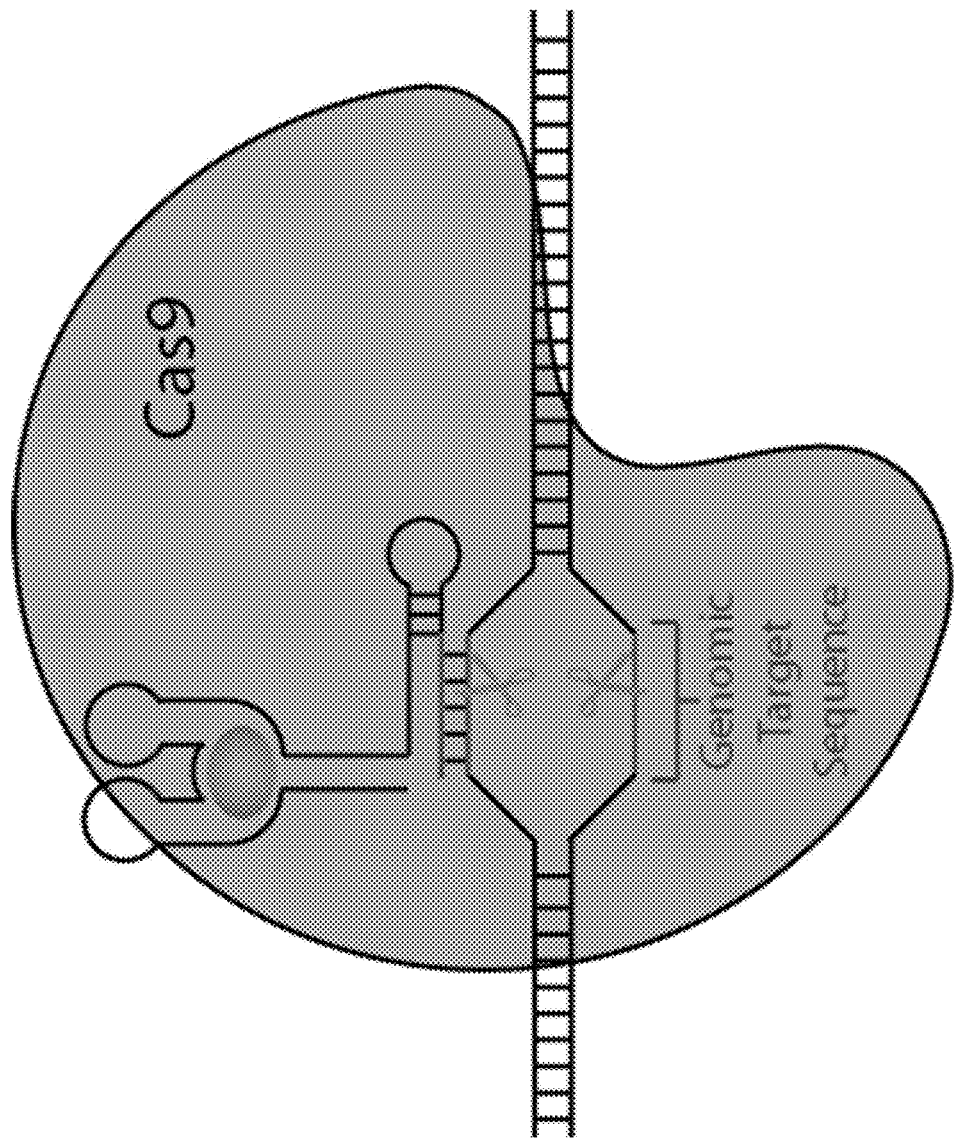

As used herein and in the claims, the singular forms "a," "an," and "the" include the singular and the plural reference unless the context clearly indicates otherwise. Thus, for example, a reference to "an agent" includes a single agent and a plurality of such agents.

The term "aptamer" refers to nucleic acid or peptide molecules that bind to a specific target molecule, e.g., a specific ligand. In some embodiments, binding of the ligand to the aptamer induces conformational changes in the aptamer, and e.g., other molecules conjugated or linked to the aptamer. In some embodiments, nucleic acid (e.g., DNA or RNA) aptamers are engineered through repeated rounds of in vitro selection or equivalently, SELEX (systematic evolution of ligands by exponential enrichment) to bind to various molecular targets, for example, small molecules, macromolecules, metabolites, proteins, proteins, carbohydrates, metals, nucleic acids, cells, tissues and organisms. Methods for engineering aptamers to bind small molecules are known in the art and include those described in U.S. Pat. Nos. 5,580,737 and 8,492,082; Ellington and Szostak, "In vitro selection of RNA molecules that bind specific ligands." *Nature.* 1990; 346:818-822; Tuerk and Gold, "Systematic evolution of ligands by exponential enrichment: RNA ligands to bacteriophage T4 DNA polymerase." *Science.* 1990; 249:505-510; Burke and Gold, "RNA aptamers to the adenosine moiety of S-adenosyl methionine: structural inferences from variations on a theme and the reproducibility of SELEX." *Nucleic Acids Res.* 1997; 25(10):2020-4; Ulrich et al., "DNA and RNA aptamers: from tools for basic research towards therapeutic applications." *Comb Chem High Throughput Screen.* 2006; 9(8):619-32; Svobodová et al., "Comparison of different methods for generation of single-stranded DNA for SELEX processes. *Anal Bioanal Chem.* 2012; 404:835-842; the entire contents of each are hereby incorporated by reference. Nucleic acid aptamers are also found in nature, for example, those that form part of a riboswitch. A "riboswitch" is a regulatory segment of a mRNA molecule that binds a small molecule, for example, a metabolite, resulting in a change in production of the protein(s) encoded by the mRNA (e.g., proteins involved in the production of the metabolite binding the riboswitch). Riboswitches are often conceptually divided into two parts: an aptamer and an expression platform (e.g., mRNA). The aptamer directly binds the small molecule (e.g., metabolite), and the mRNA undergoes structural changes in response to the changes in the aptamer. Typically, the structural changes in the mRNA result in a decrease or inhibition of protein expression. Aptamers can be cloned from (e.g., separated from) riboswitches and used to control the activity of other molecules (e.g., RNA, DNA) linked thereto using routine methods in the art. Additionally, aptamers found in nature can be re-engineered to bind to synthetic, non-natural small molecule ligands to control the activities of other molecules linked thereto using known methods. See, e.g., Dixon et al., "Reengineering orthogonally selective riboswitches." *PNAS* 2010; 107 (7): 2830-2835, the entire contents of which is hereby incorporated by reference. The following is a non-limiting list of riboswitches that include aptamers:

Cobalamin riboswitch (also $B_{12}$-element), which binds adenosylcobalamin (the coenzyme form of vitamin $B_{12}$) to regulate cobalamin biosynthesis and transport of cobalamin and similar metabolites, and other genes. See, e.g., Nahvi et al., "Coenzyme B12 riboswitches are widespread genetic control elements in prokaryotes." *Nucleic Acids Res.* 2004; 32: 143-150; Vitreschak et al., "Regulation of the vitamin B12 metabolism and transport in bacteria by a conserved RNA structural element." RNA. 2003; 9:1084-1097; the entire contents of each are hereby incorporated by reference.

cyclic di-GMP riboswitches bind the signaling molecule cyclic di-GMP in order to regulate a variety of genes controlled by this second messenger. At least two classes of cyclic di-GMP riboswitches are known: cyclic di-GMP-I riboswitches and cyclic di-GMP-II riboswitches. See, e.g., Sudarsan et al., "Riboswitches in eubacteria sense the second messenger cyclic di-GMP." *Science.* 2008; 321 (5887): 411-3; Lee et al., "An allosteric self-splicing ribozyme triggered by a bacterial second messenger." *Science.* 2010; 329 (5993): 845-8; the entire contents of each are hereby incorporated by reference.

FMN riboswitch (also RFN-element) binds flavin mononucleotide (FMN) to regulate riboflavin biosynthesis and transport. See, e.g., Winkler et al., "An mRNA structure that controls gene expression by binding FMN." *Proc Natl Acad Sci USA.* 2002; 99 (25): 15908-15913; Serganov et al., "Coenzyme recognition and gene regulation by a flavin mononucleotide riboswitch." *Nature.* 2009; 458 (7235): 233-7; the entire contents of each are hereby incorporated by reference.

GlmS riboswitch is a ribozyme that cleaves itself when bound by glucosamine-6-phosphate. See, e.g., Winkler et al., "Control of gene expression by a natural metabolite-responsive ribozyme." *Nature.* 2004; 428: 281-286; Jansen et al., "Backbone and nucleobase contacts to glucosamine-6-phosphate in the glmS ribozyme." *Nat Struct Mol Biol.* 2006; 13: 517-523; Hampel and Tinsley, "Evidence for preorganization of the glmS ribozyme ligand binding pocket." *Biochemistry.* 2006; 45: 7861-7871; the entire contents of each are hereby incorporated by reference.

Glycine riboswitch binds glycine to regulate glycine metabolism genes, including the use of glycine as an energy source. See, e.g., Mandal et al., "A glycine-dependent riboswitch that uses cooperative binding to control gene expression." *Science.* 2004; 306 (5694): 275-279; Kwon and Strobel, "Chemical basis of glycine riboswitch cooperativity." *RNA.* 2008; 14 (1): 25-34; the entire contents of each are hereby incorporated by reference.

Lysine riboswitch (also L-box) binds lysine to regulate lysine biosynthesis, catabolism and transport. See, e.g., Sudarsan et al., "An mRNA structure in bacteria that controls gene expression by binding lysine." *Genes Dev.* 2003; 17:2688-2697; Grundy et al., "The L box regulon: Lysine sensing by leader RNAs of bacterial lysine biosynthesis genes." *Proc. Natl. Acad. Sci. USA.* 2003; 100:12057-12062; the entire contents of each are hereby incorporated by reference.

PreQ1 riboswitches bind pre-queuosine$_1$, to regulate genes involved in the synthesis or transport of this precursor to queuosine. At least two distinct classes of PreQ1 riboswitches are known: PreQ1-I riboswitches and PreQ1-II riboswitches. See, e.g., Roth et al., "A riboswitch selective for the queuosine precursor preQ1 contains an unusually small aptamer domain," *Nat Struct Mol Biol.* 2007; 14 (4): 308-317; Klein et al., "Cocrystal structure of a class I preQ1 riboswitch reveals a pseudoknot recognizing an essential hypermodified nucleobase," *Nat. Struct. Mol. Biol.* 2009; 16 (3): 343-344; Kang et al., "Structural Insights into riboswitch control of the biosynthesis of queuosine, a modified nucleotide found in the anticodon of tRNA." *Mol. Cell* 33 2009; (6): 784-90; Meyer et al., "Confirmation of a second natural preQ1 aptamer class in Streptococcaceae bacteria." RNA 2008; 14 (4): 685; the entire contents of each are hereby incorporated by reference.

Purine riboswitches binds purines to regulate purine metabolism and transport. Different forms of the purine riboswitch bind guanine (a form originally known as the G-box) or adenine. The specificity for either guanine or adenine depends completely upon Watson-Crick interactions with a single pyrimidine in the riboswitch at a particular position, e.g., Y74. In the guanine riboswitch this residue is typically a cytosine (e.g., C74), in the adenine roboswitch it is typically a uracil (e.g., U74). Homologous types of purine riboswitches bind deoxyguanosine but have more significant differences than a single nucleotide mutation. See e.g., Serganov et al., "Structural basis for discriminative regulation of gene expression by adenine- and guanine-sensing mRNAs." *Chem Biol.* 2004; 11 (12): 1729-41; Batey et al., "Structure of a natural guanine-responsive riboswitch complexed with the metabolite hypoxanthine." *Nature.* 2004; 432 (7015): 411-415; Mandal and Breaker, "Adenine riboswitches and gene activation by disruption of a transcription terminator." *Nat Struct Mol Biol.* 2004; 11 (1): 29-35; the entire contents of each are hereby incorporated by reference.

SAH riboswitches bind S-adenosylhomocysteine to regulate genes involved in recycling this metabolite that is produced when S-adenosylmethionine is used in methylation reactions. See, e.g., Wang et al., "Riboswitches that Sense S-adenosylhomocysteine and Activate Genes Involved in Coenzyme Recycling." *Mol. Cell* 2008; 29 (6): 691-702; Edwards et al., "Structural basis for recognition of S-adenosylhomocysteine by riboswitches." *RNA* 2010; 16 (11): 2144-2155; the entire contents of each are hereby incorporated by reference.

SAM riboswitches bind S-adenosyl methionine (SAM) to regulate methionine and SAM biosynthesis and transport. At least four SAM riboswitches are known: SAM-I (originally called S-box), SAM-II, the $S_{MK}$ box riboswitch and Sam-IV. SAM-I is widespread in bacteria, but SAM-II is found only in alpha-, beta- and a few gamma-proteobacteria. The $S_{MK}$ box riboswitch is believed to be found only in the order Lactobacillales. SAM-IV riboswitches have a similar ligand-binding core to that of SAM-I riboswitches, but in the context of a distinct scaffold. See, e.g., Montange et al., "Structure of the S-adenosyl methionine riboswitch regulatory mRNA element." *Nature.* 2006; 441:1172-1175; Winkler et al., "An mRNA structure that controls gene expression by binding Sadenosylmethionine." *Nat Struct Biol.* 2003; 10: 701-707; Zasha et al., "The aptamer core of SAM-IV riboswitches mimics the ligand-binding site of SAM-I riboswitches." RNA. 2008; 14(5): 822-828; the entire contents of each are hereby incorporated by reference.

Tetrahydrofolate riboswitches bind tetrahydrofolate to regulate synthesis and transport genes. See, e.g., Ames et al., "A eubacterial riboswitch class that senses the coenzyme tetrahydrofolate." *Chem. Biol.* 2010; 17 (7): 681-5; Huang et al., "Long-range pseudoknot interactions dictate the regulatory response in the tetrahydrofolate riboswitch." *Proc. Natl. Acad. Sci. U.S.A.* 2011; 108 (36): 14801-6; Trausch et al., "The structure of a tetrahydrofolate-sensing riboswitch reveals two ligand binding sites in a single aptamer." *Structure.* 2011; 19 (10): 1413-23; the entire contents of each are hereby incorporated by reference.

Theophylline riboswitch was identified by SELEX and selectively binds the small molecule theophylline. The aptamer comprises a 15-nucleotide core motif that is required for theophylline binding. See, e.g., Jenison et al., "High-resolution molecular discrimination by RNA." *Science*. 1994; 263:1425-1429; Zimmerman et al., "Molecular interactions and metal binding in the theophylline-binding core of an RNA aptamer." *RNA*. 2000; 6(5):659-67; Suess et al., "A theophylline responsive riboswitch based on helix slipping controls gene expression in vivo." *Nucleic Acids Res.* 2004; 32(4): 1610-1614; the entire contents of each are hereby incorporated by reference. See also, e.g., FIG. 1C-D.

TPP riboswitches (also THI-box) bind thiamin pyrophosphate (TPP) to regulate thiamin biosynthesis and transport, as well as transport of similar metabolites. It is believed to be the only riboswitch found so far in eukaryotes. See, e.g., Edwards et al., "Crystal structures of the thi-box riboswitch bound to thiamine pyrophosphate analogs reveal adaptive RNA-small molecule recognition." *Structure* 2006; 14 (9): 1459-68; Winkler et al., "Thiamine derivatives bind messenger RNAs directly to regulate bacterial gene expression." *Nature*. 2002; 419 (6910): 952-956; Serganov et al., "Structural basis for gene regulation by a thiamine pyrophosphate-sensing riboswitch." *Nature*. 2006; 441 (7097): 1167-1171; the entire contents of each are hereby incorporated by reference.

The term "Cas9" or "Cas9 nuclease" refers to an RNA-guided nuclease comprising a Cas9 protein, or a fragment thereof. A Cas9 nuclease is also referred to sometimes as a casn1 nuclease or a CRISPR (clustered regularly interspaced short palindromic repeat)-associated nuclease. CRISPR is an adaptive immune system that provides protection against mobile genetic elements (e.g., viruses, transposable elements and conjugative plasmids). CRISPR clusters contain spacers, sequences complementary to antecedent mobile elements, and target invading nucleic acids. CRISPR clusters are transcribed and processed into CRISPR RNA (crRNA). In type II CRISPR systems correct processing of pre-crRNA requires a trans-encoded small RNA (tracrRNA), endogenous ribonuclease 3 (rnc) and a Cas9 protein. The tracrRNA serves as a guide for ribonuclease 3-aided processing of pre-crRNA. Subsequently, Cas9/crRNA/tracrRNA endonucleolytically cleaves linear or circular dsDNA target complementary to the spacer. The target strand not complementary to crRNA is first cut endonucleolytically, then trimmed 3'-5' exonucleolytically. In nature, DNA-binding and cleavage typically requires protein and both RNA species. However, single guide RNAs ("sgRNA", or simply "gNRA") can be engineered so as to incorporate aspects of both the crRNA and tracrRNA into a single RNA molecule. See, e.g., Jinek M., Chylinski K., Fonfara I., Hauer M., Doudna J. A., Charpentier E. *Science* 337: 816-821(2012), the entire contents of which is hereby incorporated by reference. Cas9 recognizes a short motif in the CRISPR repeat sequences (the PAM or protospacer adjacent motif) to help distinguish self versus non-self. Cas9 nuclease sequences and structures are well known to those of skill in the art (see, e.g., "Complete genome sequence of an M1 strain of *Streptococcus pyogenes*." Ferretti J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L. expand/collapse author list McLaughlin R. E., Proc. Natl. Acad. Sci. U.S.A. 98:4658-4663(2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., Nature 471:602-607(2011); and "A programmable dual-RNA-guided DNA endonuclease in adaptive bacterial immunity." Jinek M., Chylinski K., Fonfara I., Hauer M., Doudna J. A., Charpentier E. *Science* 337:816-821(2012), the entire contents of each of which are incorporated herein by reference). Cas9 orthologs have been described in various species, including, but not limited to, *S. pyogenes* and *S. thermophilus*. Additional suitable Cas9 nucleases and sequences will be apparent to those of skill in the art based on this disclosure, and such Cas9 nucleases and sequences include Cas9 sequences from the organisms and loci disclosed in Chylinski, Rhun, and Charpentier, "The tracrRNA and Cas9 families of type II CRISPR-Cas immunity systems" (2013) RNA Biology 10:5, 726-737; the entire contents of which are incorporated herein by reference. In some embodiments, proteins comprising Cas9 or fragments thereof proteins are referred to as "Cas9 variants." A Cas9 variant shares homology to Cas9, or a fragment thereof. For example a Cas9 variant is at least about 70% identical, at least about 80% identical, at least about 90% identical, at least about 95% identical, at least about 98% identical, at least about 99% identical, at least about 99.5% identical, or at least about 99.9% to wild type Cas9. In some embodiments, the Cas9 variant comprises a fragment of Cas9 (e.g., a gRNA binding domain or a DNA-cleavage domain), such that the fragment is at least about 70% identical, at least about 80% identical, at least about 90% identical, at least about 95% identical, at least about 98% identical, at least about 99% identical, at least about 99.5% identical, or at least about 99.9% to the corresponding fragment of wild type Cas9. In some embodiments, wild type Cas9 corresponds to Cas9 from *Streptococcus pyogenes* (NCBI Reference Sequence: NC_017053.1, SEQ ID NO:1 (nucleotide); SEQ ID NO:2 (amino acid)).

```
                                              (SEQ ID NO: 1)
ATGGATAAGAAATACTCAATAGGCTTAGATATCGGCACAAATAGCGTCGG
ATGGGCGGTGATCACTGATGATTATAAGGTTCCGTCTAAAAAGTTCAAGG
TTCTGGGAAATACAGACCGCCACAGTATCAAAAAAAATCTTATAGGGGCT
CTTTTATTTGGCAGTGGAGAGACAGCGGAAGCGACTCGTCTCAAACGGAC
AGCTCGTAGAAGGTATACACGTCGGAAGAATCGTATTTGTTATCTACAGG
AGATTTTTTCAAATGAGATGGCGAAAGTAGATGATAGTTTCTTTCATCGA
CTTGAAGAGTCTTTTTTGGTGGAAGAAGACAAGAAGCATGAACGTCATCC
TATTTTTGGAAATATAGTAGATGAAGTTGCTTATCATGAGAAATATCCAA
CTATCTATCATCTGCGAAAAAAATTGGCAGATTCTACTGATAAAGCGGAT
TTGCGCTTAATCTATTTGGCCTTAGCGCATATGATTAAGTTTCGTGGTCA
TTTTTTGATTGAGGGAGATTTAAATCCTGATAATAGTGATGTGGACAAAC
TATTTATCCAGTTGGTACAAATCTACAATCAATTATTTGAAGAAAACCCT
ATTAACGCAAGTAGAGTAGATGCTAAAGCGATTCTTTCTGCACGATTGAG
TAAATCAAGACGATTAGAAAATCTCATTGCTCAGCTCCCCGGTGAGAAGA
GAAATGGCTTGTTTGGGAATCTCATTGCTTTGTCATTGGGATTGACCCCT
AATTTTAAATCAAATTTTGATTTGGCAGAAGATGCTAAATTACAGCTTTC
AAAAGATACTTACGATGATGATTTAGATAATTTATTGGCGCAAATTGGAG
ATCAATATGCTGATTTGTTTTTGGCAGCTAAGAATTTATCAGATGCTATT
TTACTTTCAGATATCCTAAGAGTAAATAGTGAAATAACTAAGGCTCCCCT
ATCAGCTTCAATGATTAAGCGCTACGATGAACATCATCAAGACTTGACTC
TTTTAAAAGCTTTAGTTCGACAACAACTTCCAGAAAAGTATAAAGAAATC
TTTTTTGATCAATCAAAAAACGGATATGCAGGTTATATTGATGGGGGAGC
TAGCCAAGAAGAATTTTATAAATTTATCAAACCAATTTTAGAAAAAATGG
ATGGTACTGAGGAATTATTGGTGAAACTAAATCGTGAAGATTTGCTGCGC
AAGCAACGGACCTTTGACAACGGCTCTATTCCCCATCAAATTCACTTGGG
TGAGCTGCATGCTATTTTGAGAAGACAAGAAGACTTTTATCCATTTTTAA
AAGACAATCGTGAGAAGATTGAAAAAATCTTGACTTTTCGAATTCCTTAT
TATGTTGGTCCATTGGCGCGTGGCAATAGTCGTTTTGCATGGATGACTCG
GAAGTCTGAAGAAACAATTACCCCATGGAATTTTGAAGAAGTTGTCGATA
AAGGTGCTTCAGCTCAATCATTTATTGAACGCATGACAAACTTTGATAAA
AATCTTCCAAATGAAAAAGTACTACCAAAACATAGTTTGCTTTATGAGTA
TTTTACGGTTTATAACGAATTGACAAAGGTCAAATATGTTACTGAGGGAA
TGCGAAAACCAGCATTTCTTTCAGGTGAACAGAAGAAAGCCATTGTTGAT
TTACTCTTCAAAACAAATCGAAAAGTAACCGTTAAGCAATTAAAAGAAGA
TTATTTCAAAAAAATAGAATGTTTTGATAGTGTTGAAATTTCAGGAGTTG
AAGATAGATTTAATGCTTCATTAGGCGCCTACCATGATTTGCTAAAAATT
ATTAAAGATAAAGATTTTTTGGATAATGAAGAAAATGAAGATATCTTAGA
GGATATTGTTTTAACATTGACCTTATTTGAAGATAGGGGGATGATTGAGG
AAAGACTTAAAACATATGCTCACCTCTTTGATGATAAGGTGATGAAACAG
CTTAAACGTCGCCGTTATACTGGTTGGGGACGTTTGTCTCGAAAATTGAT
TAATGGTATTAGGGATAAGCAATCTGGCAAAACAATATTAGATTTTTTGA
AATCAGATGGTTTTGCCAATCGCAATTTTATGCAGCTGATCCATGATGAT
```

```
-continued
AGTTTGACATTTAAAGAAGATATTCAAAAAGCACAGGTGTCTGGACAAGG
CCATAGTTTACATGAACAGATTGCTAACTTAGCTGGCAGTCCTGCTATTA
AAAAAGGTATTTTACAGACTGTAAAAATTGTTGATGAACTGGTCAAAGTA
ATGGGGCATAAGCCAGAAAATATCGTTATTGAAATGGCACGTGAAAATCA
GACAACTCAAAAGGGCCAGAAAAATTCGCGAGAGCGTATGAAACGAATCG
AAGAAGGTATCAAAGAATTAGGAAGTCAGATTCTTAAAGAGCATCCTGTT
GAAAATACTCAATTGCAAATGAAAAGCTCTATCTCTATTATCTACAAAA
TGGAAGAGACATGTATGTGGACCAAGAATTAGATATTAATCGTTTAAGTG
ATTATGATGTCGATCACATTGTTCCACAAAGTTTCATTAAAGACGATTCA
ATAGACAATAAGGTACTAACGCGTTCTGATAAAAATCGTGGTAAATCGGA
TAACGTTCCAAGTGAAGAAGTAGTCAAAAAGATGAAAAACTATTGGAGAC
AACTTCTAAACGCCAAGTTAATCACTCAACGTAAGTTTGATAATTTAACG
AAAGCTGAACGTGGAGGTTTGAGTGAACTTGATAAAGCTGGTTTTATCAA
ACGCCAATTGGTTGAAACTCGCCAAATCACTAAGCATGTGGCACAAATTT
TGGATAGTCGCATGAATACTAAATACGATGAAAATGATAAACTTATTCGA
GAGGTTAAAGTGATTACCTTAAAATCTAAATTAGTTTCTGACTTCCGAAA
AGATTTCCAATTCTATAAAGTACGTGAGATTAACAATTACCATCATGCCC
ATGATGCGTATCTAAATGCCGTCGTTGGAACTGCTTTGATTAAGAAATAT
CCAAAACTTGAATCGGAGTTTGTCTATGGTGATTATAAAGTTTATGATGT
TCGTAAAATGATTGCTAAGTCTGAGCAAGAAATAGGCAAAGCAACCGCAA
AATATTTCTTTTACTCTAATATCATGAACTTCTTCAAAACAGAAATTACA
CTTGCAAATGGAGAGATTCGCAAACGCCCTCTAATCGAAACTAATGGGGA
AACTGGAGAAATTGTCTGGGATAAAGGGCGAGATTTTGCCACAGTGCGCA
AAGTATTGTCCATGCCCCAAGTCAATATTGTCAAGAAAACAGAAGTACAG
ACAGGCGGATTCTCCAAGGAGTCAATTTTACCAAAAAGAAATTCGGACAA
GCTTATTGCTCGTAAAAAAGACTGGGATCCAAAAAATATGGTGGTTTTG
ATAGTCCAACGGTAGCTTATTCAGTCCTAGTGGTTGCTAAGGTGGAAAAA
GGGAAATCGAAGAAGTTAAAATCCGTTAAAGAGTTACTAGGGATCACAAT
TATGGAAAGAAGTTCCTTTGAAAAAAATCCGATTGACTTTTTAGAAGCTA
AAGGATATAAGGAAGTTAAAAAAGACTTAATCATTAAACTACCTAAATAT
AGTCTTTTTGAGTTAGAAAACGGTCGTAAACGGATGCTGGCTAGTGCCGG
AGAATTACAAAAGGAAATGAGCTGGCTCTGCCAAGCAAATATGTGAATT
TTTTATATTTAGCTAGTCATTATGAAAAGTTGAAGGGTAGTCCAGAAGAT
AACGAACAAAAACAATTGTTTGTGGAGCAGCATAAGCATTATTTAGATGA
GATTATTGAGCAAATCAGTGAATTTCTAAGCGTGTTATTTTAGCAGATG
CCAATTTAGATAAAGTTCTTAGTGCATATAACAAACATAGAGACAAACCA
ATACGTGAACAAGCAGAAAATATTATTCATTTATTTACGTTGACGAATCT
TGGAGCTCCCGCTGCTTTTAAATATTTTGATACAACAATTGATCGTAAAC
GATATACGTCTACAAAGAAGTTTTAGATGCCACTCTTATCCATCAATCC
ATCACTGGTCTTTATGAAACACGCATTGATTTGAGTCAGCTAGGAGGTGA
CTGA
                                                (SEQ ID NO: 2)
MDKKYSIGLDIGTNSVGWAVITDDYKVPSKKFKVLGNTDRHSIKKNLIGA
LLFGSGETAEATRLKRTARRRYTRRKNRICYLQEIFSNEMAKVDDSFFHR
LEESFLVEEDKKHERHPIFGNIVDEVAYHEKYPTIYHLRKKLADSTDKAD
LRLIYLALAHMIKFRGHFLIEGDLNPDNSDVDKLFIQLVQIYNQLFEENP
INASRVDAKAILSARLSKSRRLENLIAQLPGEKRNGLFGNLIALSLGLTP
NFKSNFDLAEDAKLQLSKDTYDDDLDNLLAQIGDQYADLFLAAKNLSDAI
LLSDILRVNSEITKAPLSASMIKRYDEHHQDLTLLKALVRQQLPEKYKEI
FFDQSKNGYAGYIDGGASQEEFYKFIKPILEKMDGTEELLVKLNREDLLR
KQRTFDNGSIPHQIHLGELHAILRRQEDFYPFLKDNREKIEKILTFRIPY
YVGPLARGNSRFAWMTRKSEETITPWNFEEVVDKGASAQSFIERMTNFDK
NLPNEKVLPKHSLLYEYFTVYNELTKVKYVTEGMRKPAFLSGEQKKAIVD
LLFKTNRKVTVKQLKEDYFKKIECFDSVEISGVEDRFNASLGAYHDLLKI
IKDKDFLDNEENEDILEDIVLTLTLFEDRGMIEERLKTYAHLFDDKVMKQ
LKRRRYTGWGRLSRKLINGIRDKQSGKTILDFLKSDGFANRNFMQLIHDD
SLTFKEDIQKAQVSGQGHSLHEQIANLAGSPAIKKGILQTVKIVDELVKV
MGHKPENIVIEMARENQTTQKGQKNSRERMKRIEEGIKELGSQILKEHPV
ENTQLQNEKLYLYYLQNGRDMYVDQELDINRLSDYDVDHIVPQSFIKDDS
IDNKVLTRSDKNRGKSDNVPSEEVVKKMKNYWRQLLNAKLITQRKFDNLT
KAERGGLSELDKAGFIKRQLVETRQITKHVAQILDSRMNTKYDENDKLIR
EVKVITLKSKLVSDFRKDFQFYKVREINNYHHAHDAYLNAVVGTALIKKY
PKLESEFVYGDYKVYDVRKMIAKSEQEIGKATAKYFFYSNIMNFFKTEIT
LANGEIRKRPLIETNGETGEIVWDKGRDFATVRKVLSMPQVNIVKKTEVQ
TGGFSKESILPKRNSDKLIARKKDWDPKKYGGFDSPTVAYSVLVVAKVEK
GKSKKLKSVKELLGITIMERSSFEKNPIDFLEAKGYKEVKKDLIIKLPKY
SLFELENGRKRMLASAGELQKGNELALPSKYVNFLYLASHYEKLKGSPED
NEQKQLFVEQHKHYLDEIIEQISEFSKRVILADANLDKVLSAYNKHRDKP
IREQAENIIHLFTLTNLGAPAAFKYFDTTIDRKRYTSTKEVLDATLIHQS
ITGLYETRIDLSQLGGD
```

The terms "conjugating," "conjugated," and "conjugation" refer to an association of two entities, for example, of two molecules such as two proteins, two domains (e.g., a binding domain and a cleavage domain), or a protein and an agent, e.g., a protein binding domain and a small molecule. In some aspects, the association is between a protein (e.g., RNA-programmable nuclease) and a nucleic acid (e.g., a guide RNA). The association can be, for example, via a direct or indirect (e.g., via a linker) covalent linkage. In some embodiments, the association is covalent. In some embodiments, two molecules are conjugated via a linker connecting both molecules. For example, in some embodiments where two portions of RNA are conjugated to each other, e.g., an aptamer (or nucleic acid sensing domain) and a gRNA, the two RNAs may be conjugated via a polynucleotide linker, e.g., a nucleotide sequence connecting the 3' end of one RNA to the 5' end of the other RNA. In some embodiments, the linker comprises at least 1, at least 2, at least 3, at least 4, at least 5, at least 6, at least 7, at least 8, at least 9, at least 10, at least 15, at least 20, at least 25, or at least 30 nucleotides.

The term "consensus sequence," as used herein in the context of nucleic acid sequences, refers to a calculated sequence representing the most frequent nucleotide residues found at each position in a plurality of similar sequences. Typically, a consensus sequence is determined by sequence alignment in which similar sequences are compared to each other and similar sequence motifs are calculated.

The term "effective amount," as used herein, refers to an amount of a biologically active agent that is sufficient to elicit a desired biological response. For example, in some embodiments, an effective amount of a nuclease may refer to the amount of the nuclease that is sufficient to induce cleavage of a desired target site specifically bound and cleaved by the nuclease, preferably with minimal or no off-target cleavage. As will be appreciated by the skilled artisan, the effective amount of an agent, e.g., a nuclease, a hybrid protein, a fusion protein, a protein dimer, a complex of a protein (or protein dimer) and a polynucleotide, or a polynucleotide, may vary depending on various factors as, for example, on the desired biological response, the specific allele, genome, target site, cell, or tissue being targeted, and the agent being used.

The term "engineered," as used herein refers to a nucleic acid molecule, a protein molecule, complex, substance, or entity that has been designed, produced, prepared, synthesized, and/or manufactured by a human. Accordingly, an engineered product is a product that does not occur in nature.

The term "linker," as used herein, refers to a chemical group or a molecule linking two adjacent molecules or moieties, e.g., an aptamer (or nucleic acid sensing domain) and a gRNA. Typically, the linker is positioned between, or flanked by, two groups, molecules, or other moieties and connected to each one via a covalent bond, thus connecting the two. In some embodiments, the linker is a nucleotide linker. In some embodiments, the nucleotide linker comprises at least 1, at least 2, at least 3, at least 4, at least 5, at least 6, at least 7, at least 8, at least 9, at least 10, at least 15, at least 20, at least 25, or at least 30 nucleotides. In some embodiments, the linker is an amino acid or a plurality of amino acids (e.g., a peptide or protein). In some embodiments, the linker is an organic molecule, group, polymer, or chemical moiety.

The term "mutation," as used herein, refers to a substitution of a residue within a sequence, e.g., a nucleic acid or amino acid sequence, with another residue, or a deletion or insertion of one or more residues within a sequence. Mutations are typically described herein by identifying the original residue followed by the position of the residue within the sequence and by the identity of the newly substituted residue. Methods for making the amino acid substitutions (mutations) provided herein are known in the art and are provided by, for example, Green and Sambrook, *Molecular Cloning: A Laboratory Manual* (4th ed., Cold Spring Harbor Laboratory Press, Cold Spring Harbor, N.Y. (2012)).

The term "nuclease," as used herein, refers to an agent, for example, a protein or a small molecule, capable of cleaving a phosphodiester bond connecting nucleotide residues in a nucleic acid molecule. In some embodiments, a nuclease is a protein, e.g., an enzyme that can bind a nucleic acid molecule and cleave a phosphodiester bond connecting nucleotide residues within the nucleic acid molecule. A nuclease may be an endonuclease, cleaving a phosphodiester bonds within a polynucleotide chain, or an exonuclease, cleaving a phosphodiester bond at the end of the polynucleotide chain. In some embodiments, a nuclease is a site-specific nuclease, binding and/or cleaving a specific phosphodiester bond within a specific nucleotide sequence, which is also referred to herein as the "recognition sequence," the "nuclease target site," or the "target site." In some embodiments, a nuclease is a RNA-guided (i.e., RNA-programmable) nuclease, which complexes with (e.g., binds with) an RNA (e.g., a guide RNA, "gRNA") having a sequence that complements a target site, thereby providing the sequence specificity of the nuclease. In some embodiments, a nuclease recognizes a single stranded target site. In other embodiments, a nuclease recognizes a double-stranded target site, for example, a double-stranded DNA target site. The target sites of many naturally occurring nucleases, for example, many naturally occurring DNA restriction nucleases, are well known to those of skill in the art. In many cases, a DNA nuclease, such as EcoRI, HindIII, or BamHI, recognize a palindromic, double-stranded DNA target site of 4 to 10 base pairs in length, and cut each of the two DNA strands at a specific position within the target site. Some endonucleases cut a double-stranded nucleic acid target site symmetrically, i.e., cutting both strands at the same position so that the ends comprise base-paired nucleotides, also referred to herein as blunt ends. Other endonucleases cut a double-stranded nucleic acid target sites asymmetrically, i.e., cutting each strand at a different position so that the ends comprise unpaired nucleotides. Unpaired nucleotides at the end of a double-stranded DNA molecule are also referred to as "overhangs," e.g., as "5'-overhang" or as "3'-overhang," depending on whether the unpaired nucleotide(s) form(s) the 5' or the 5' end of the respective DNA strand. Double-stranded DNA molecule ends ending with unpaired nucleotide(s) are also referred to as sticky ends, as they can "stick to" other double-stranded DNA molecule ends comprising complementary unpaired nucleotide(s). A nuclease protein typically comprises a "binding domain" that mediates the interaction of the protein with the nucleic acid substrate, and also, in some cases, specifically binds to a target site, and a "cleavage domain" that catalyzes the cleavage of the phosphodiester bond within the nucleic acid backbone. In some embodiments a nuclease protein can bind and cleave a nucleic acid molecule in a monomeric form, while, in other embodiments, a nuclease protein has to dimerize or multimerize in order to cleave a target nucleic acid molecule. Binding domains and cleavage domains of naturally occurring nucleases, as well as modular binding domains and cleavage domains that can be fused to create nucleases binding specific target sites, are well known to those of skill in the art. For example, the binding domain of RNA-programmable nucleases (e.g., Cas9), or a Cas9 protein having an inactive DNA cleavage domain, can be used as a binding domain (e.g., that binds a gRNA to direct binding to a target site) to specifically bind a desired target site, and fused or conjugated to a cleavage domain, for example, the cleavage domain of FokI, to create an engineered nuclease cleaving the target site.

The terms "nucleic acid" and "nucleic acid molecule," as used herein, refer to a compound comprising a nucleobase and an acidic moiety, e.g., a nucleoside, a nucleotide, or a polymer of nucleotides. Typically, polymeric nucleic acids, e.g., nucleic acid molecules comprising three or more nucleotides are linear molecules, in which adjacent nucleotides are linked to each other via a phosphodiester linkage. In some embodiments, "nucleic acid" refers to individual nucleic acid residues (e.g. nucleotides and/or nucleosides). In some embodiments, "nucleic acid" refers to an oligonucleotide chain comprising three or more individual nucleotide residues. As used herein, the terms "oligonucleotide" and "polynucleotide" can be used interchangeably to refer to a polymer of nucleotides (e.g., a string of at least three nucleotides). In some embodiments, "nucleic acid" encompasses RNA as well as single and/or double-stranded DNA. Nucleic acids may be naturally occurring, for example, in the context of a genome, a transcript, an mRNA, tRNA, rRNA, siRNA, snRNA, a plasmid, cosmid, chromosome, chromatid, or other naturally occurring nucleic acid molecule. On the other hand, a nucleic acid molecule may be a non-naturally occurring molecule, e.g., a recombinant DNA or RNA, an artificial chromosome, an engineered genome, or fragment thereof, or a synthetic DNA, RNA, DNA/RNA hybrid, or including non-naturally occurring nucleotides or nucleosides. Furthermore, the terms "nucleic acid," "DNA," "RNA," and/or similar terms include nucleic acid analogs, i.e. analogs having other than a phosphodiester backbone. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, and backbone modifications. A nucleic acid sequence is presented in the 5' to 3' direction unless otherwise indicated. In some embodiments, a nucleic acid is or comprises natural nucleosides (e.g. adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadeno sine, 7-deazaadenosine, 7-deazaguanosine, 8-oxoadenosine, 8-oxoguanosine, 0(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

The term "pharmaceutical composition," as used herein, refers to a composition that can be administrated to a subject in the context of treatment of a disease or disorder. In some embodiments, a pharmaceutical composition comprises an active ingredient, e.g., a nuclease or a nucleic acid encoding a nuclease, and a pharmaceutically acceptable excipient.

The term "proliferative disease," as used herein, refers to any disease in which cell or tissue homeostasis is disturbed in that a cell or cell population exhibits an abnormally elevated proliferation rate. Proliferative diseases include hyperproliferative diseases, such as pre-neoplastic hyperplastic conditions and neoplastic diseases. Neoplastic diseases are characterized by an abnormal proliferation of cells and include both benign and malignant neoplasias. Malignant neoplasia is also referred to as cancer.

The terms "protein," "peptide," and "polypeptide" are used interchangeably herein and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof. The term "fusion protein" as used herein refers to a hybrid polypeptide which comprises protein domains from at least two different proteins. One protein may be located at the amino-terminal (N-terminal) portion of the fusion protein or at the carboxy-terminal (C-terminal) protein thus forming an "amino-terminal fusion protein" or a "carboxy-terminal fusion protein," respectively. A protein may comprise different domains, for example, a nucleic acid binding domain (e.g., the gRNA binding domain of Cas9 that directs the binding of the protein to a target site) and a nucleic acid cleavage domain. In some embodiments, a protein comprises a proteinaceous part, e.g., an amino acid sequence constituting a nucleic acid binding domain, and an organic compound, e.g., a compound that can act as a nucleic acid cleavage agent. In some embodiments, a protein is in a complex with, or is in association with, a nucleic acid, e.g., RNA. Any of the proteins provided herein may be produced by any method known in the art. For example, the proteins provided herein may be produced via recombinant protein expression and purification, which is especially suited for fusion proteins comprising a peptide linker. Methods for recombinant protein expression and purification are well known, and include those described by Green and Sambrook, *Molecular Cloning: A Laboratory Manual* (4th ed., Cold Spring Harbor Laboratory Press, Cold Spring Harbor, N.Y. (2012)), the entire contents of which are incorporated herein by reference.

Figure 1C:
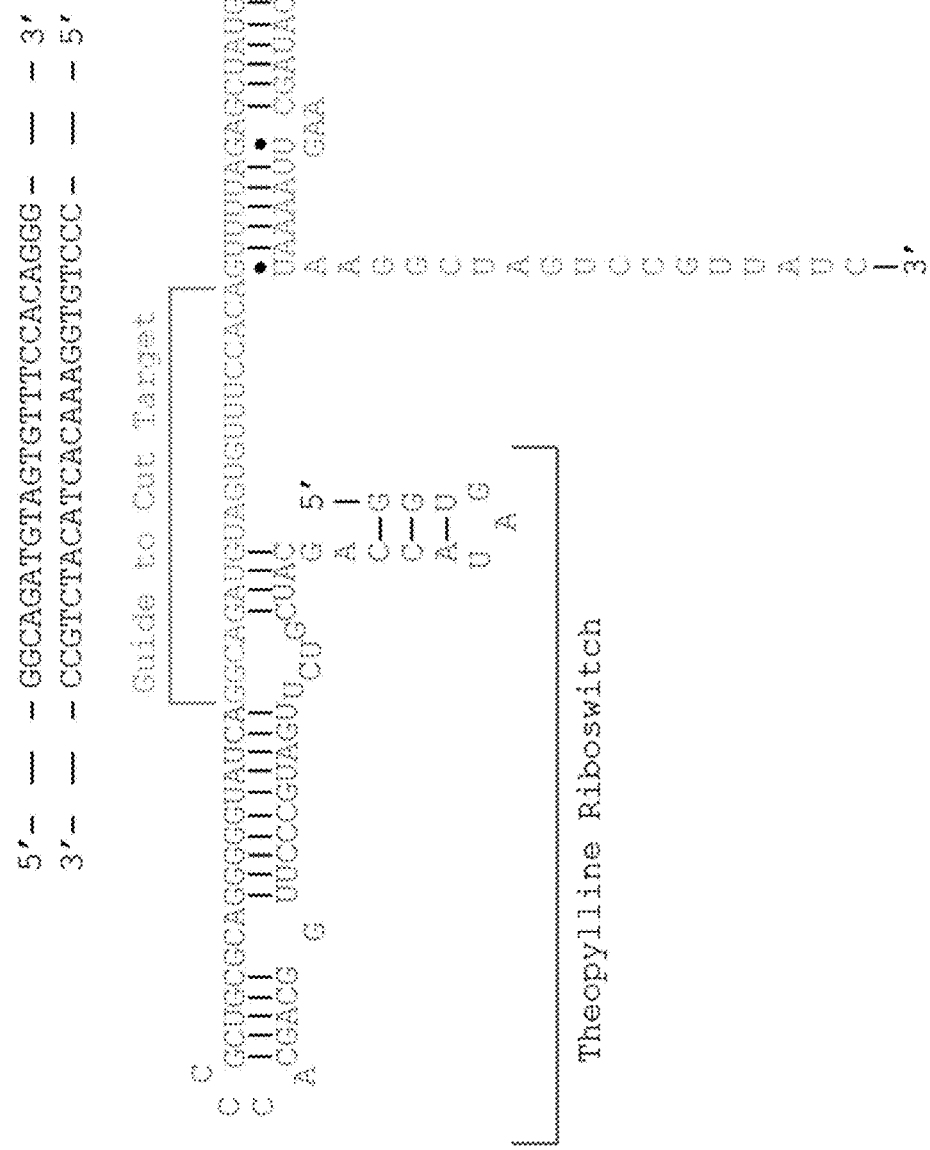
Figure 1D:
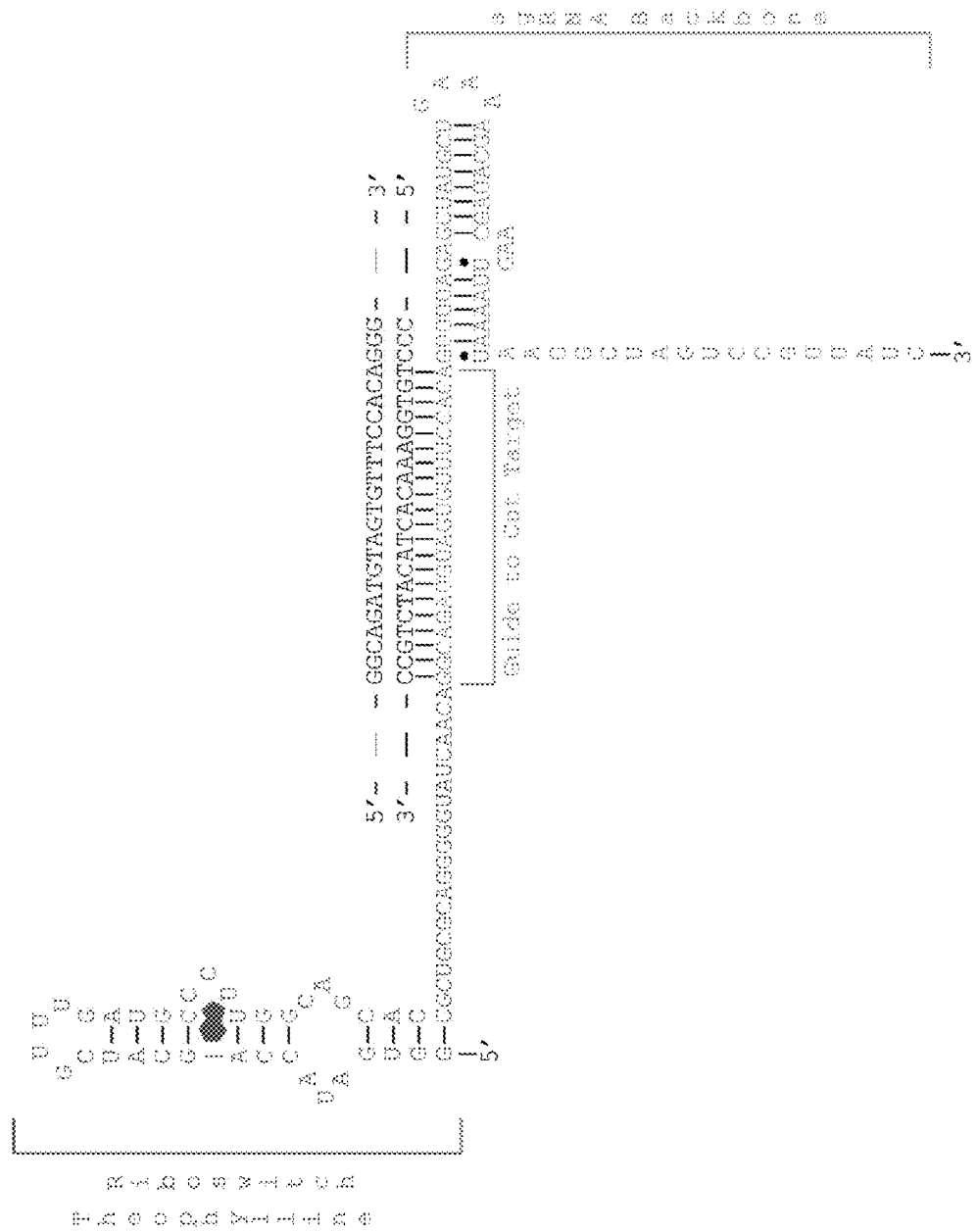
Figure 2A:
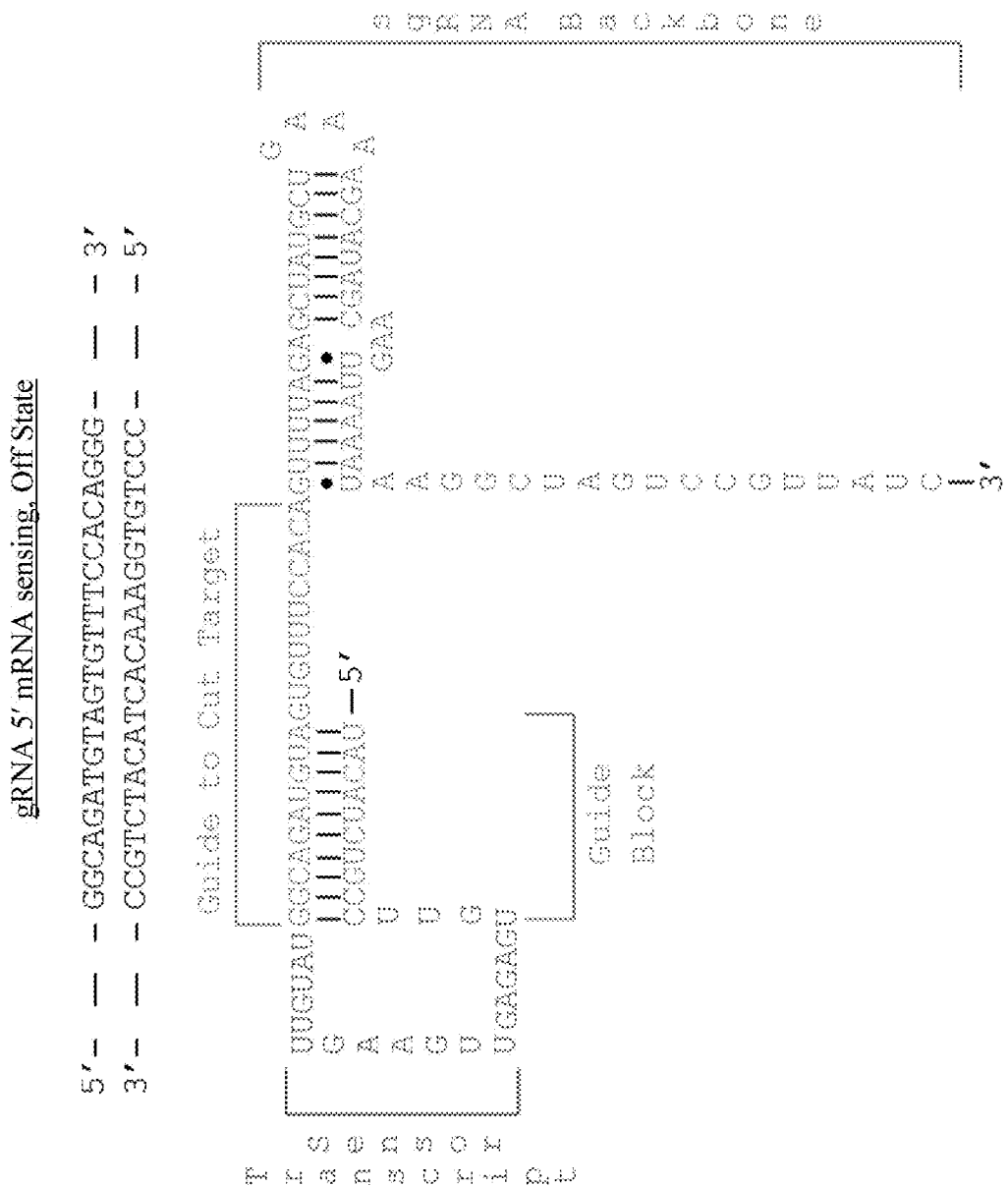
FIG. 2 shows certain embodiments of the invention relating to mRNA-sensing gRNAs. (A-B) In this figure, a gRNA comprising a 5' transcript sensor/guide block motif is depicted. In the absence of a certain mRNA (A), aspects of the transcript sensor remain unbound, resulting in the formation of a stem-loop structure that blocks certain aspects of the sequence (depicted as "Guide to Cut the Target") responsible for binding the target nucleic acid (depicted by the double-stranded sequence at the top of the panel), thereby preventing the gRNA from hybridizing to the target nucleic acid. In the presence of the mRNA to which the transcript sensor hybridizes (B), the gRNA undergoes conformational changes resulting in the "Guide" sequence being free to hybridize to the target nucleic acid. (C-D) Similarly, the strategy may be applied to gRNAs comprising a 3' transcript sensor/guide block, such that in the absence of the mRNA (C), the gRNA is in the "off" state, and in the presence of the mRNA (D), the gRNA is in the "on" state. Sequence Identifiers: The target sequence at the top of FIGS. 2A-D from 5' to 3' is SEQ ID NO:4, and from 3' to 5' is SEQ ID NO:5. The gRNA shown in FIGS. 2A and 2B corresponds to SEQ ID NO:7. The gRNA shown in FIGS. 2C and 2D corresponds to SEQ ID NO:8.
Figure 2B:
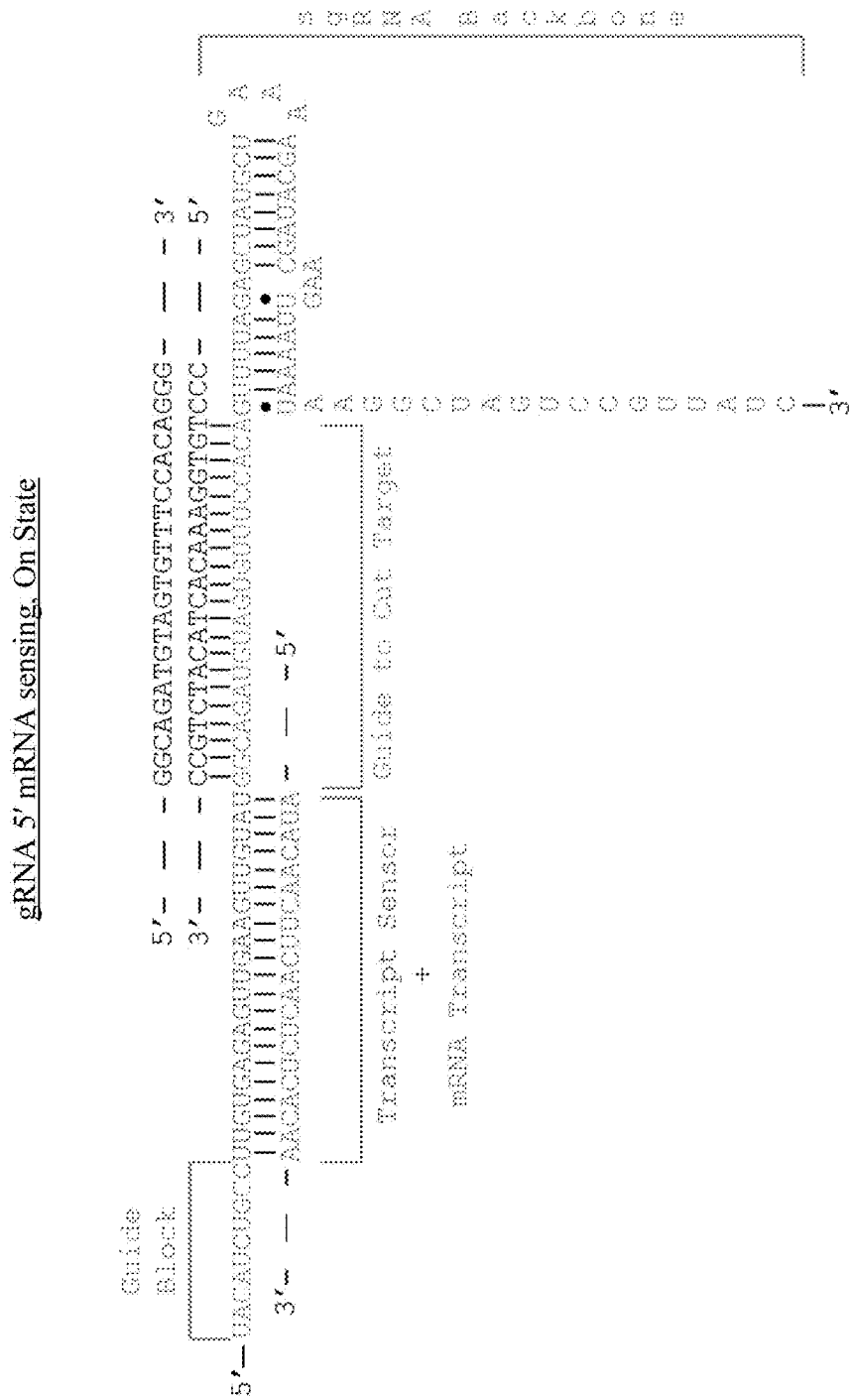
Figure 2C:
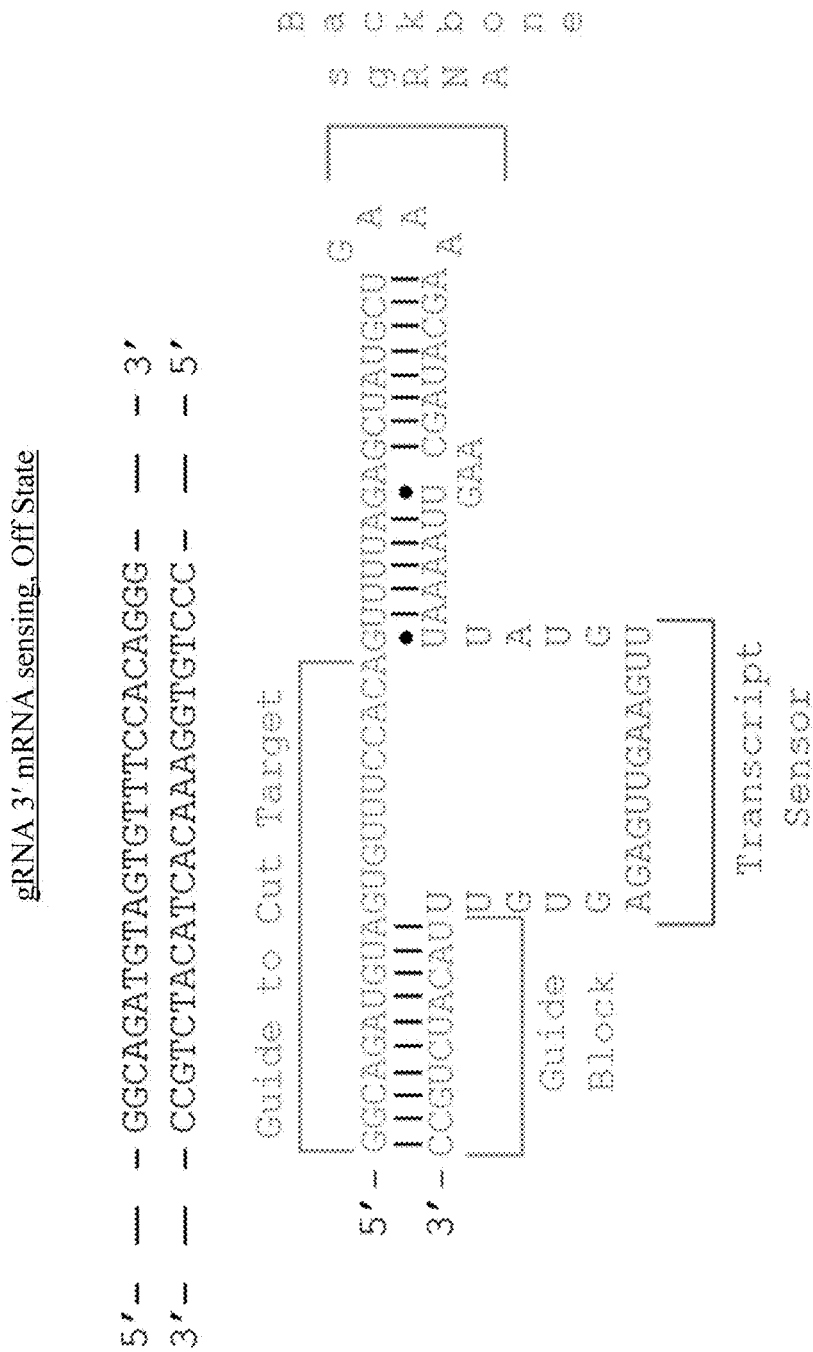
Figure 2D:
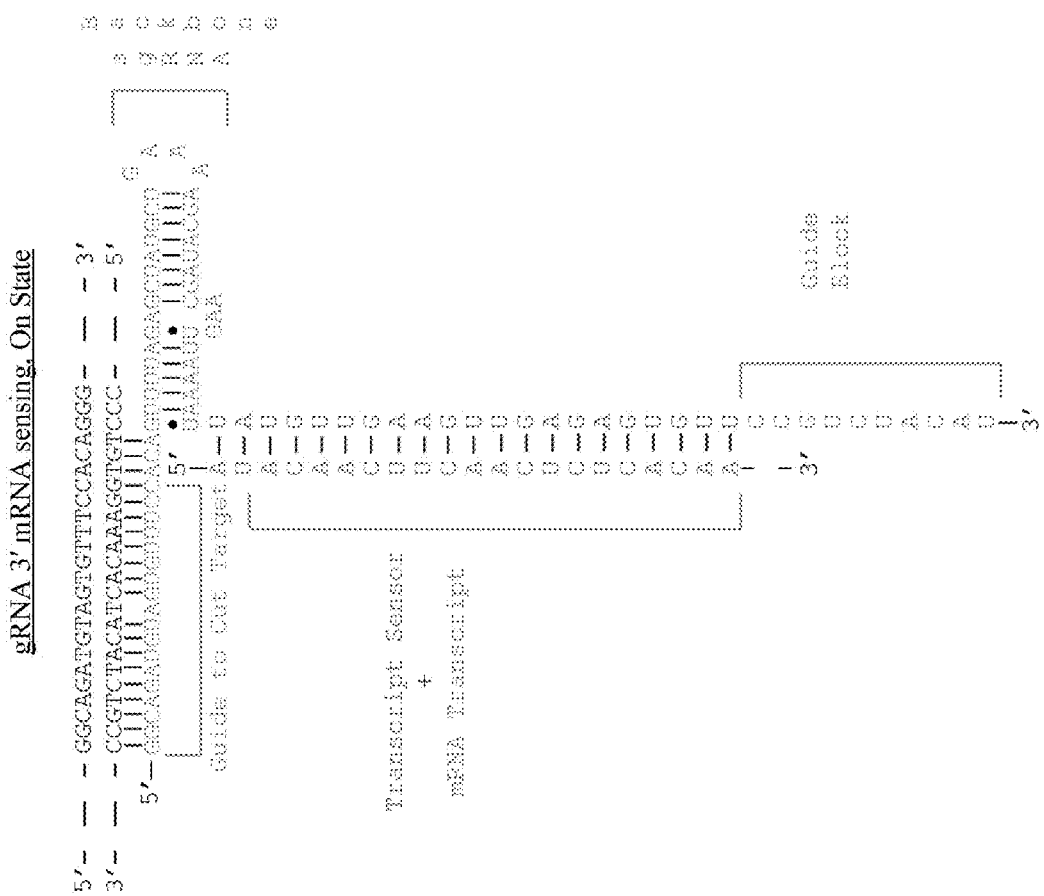
Figure 3A:
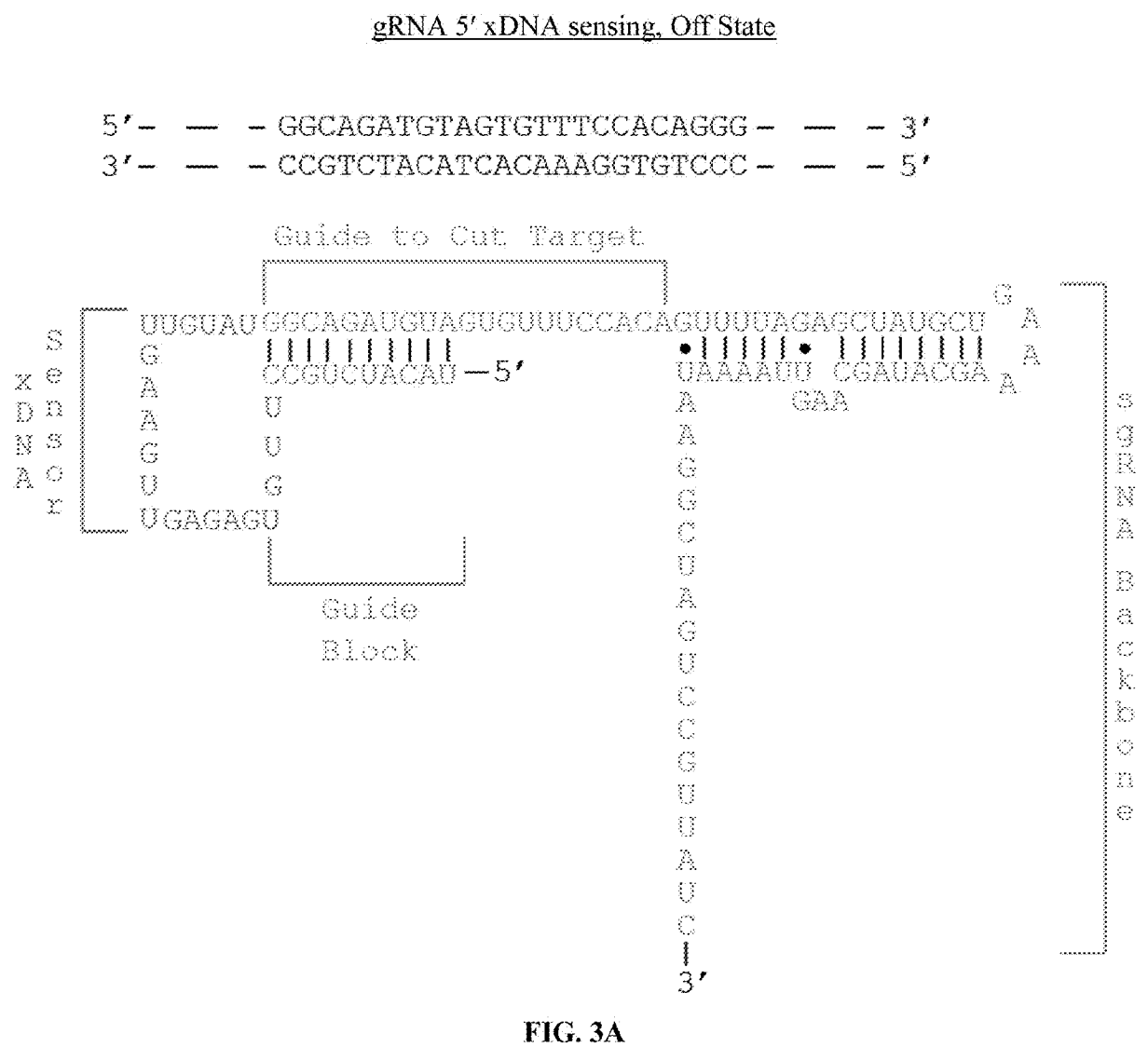
Figure 3B:
FIG. 3 shows certain embodiments of the invention relating to extended DNA (xDNA) recognition strategies. (A-B) In this embodiment, a gRNA comprising a 5' xDNA sensor/guide block motif is depicted. The xDNA sensor motif complements and hybridizes to other aspects of the target nucleic acid (e.g., in addition to the "Guide to Cut Target" sequence). (A) In the absence of the correct target sequence (e.g., comprising both the target of the "guide" sequence as well as the target of the xDNA sensor sequence), aspects of the xDNA sensor remain unbound, resulting in the formation of a stem-loop structure that blocks certain aspects of the sequence (depicted as "Guide to Cut the Target") responsible for binding the target nucleic acid (depicted by the double-stranded sequence at the top of the panel), thereby preventing the gRNA from hybridizing to the target nucleic acid. In the presence of the correct target nucleic acid to which portion(s) of the xDNA sensor hybridize(s) (B), the gRNA undergoes conformational changes resulting in the "Guide" sequence being free to hybridize to the target nucleic acid. Thus, only in the presence of the correct target nucleic acid does binding of the gRNA (and associated Cas9 protein) occur. This effectively increases (i.e., extends) the number of target nucleotides recognized by a e.g., a Cas9:gRNA complex, which increase specificity. (C-D) Similarly, the strategy may be applied to gRNAs comprising a 3' xDNA sensor/guide block, such that in the absence of the target nucleic acid (C), the gRNA is in the "off" state, and in the presence of the target nucleic acid (D), the gRNA is in the "on" state. Sequence Identifiers: The target sequence at the top of FIGS. 3A-D from 5' to 3' is SEQ ID NO:4, and from 3' to 5' is SEQ ID NO:5. The gRNA shown in FIGS. 3A and 3B corresponds to SEQ ID NO:9. The gRNA shown in FIGS. 3C and 3D corresponds to SEQ ID NO:10.
Figure 3C:
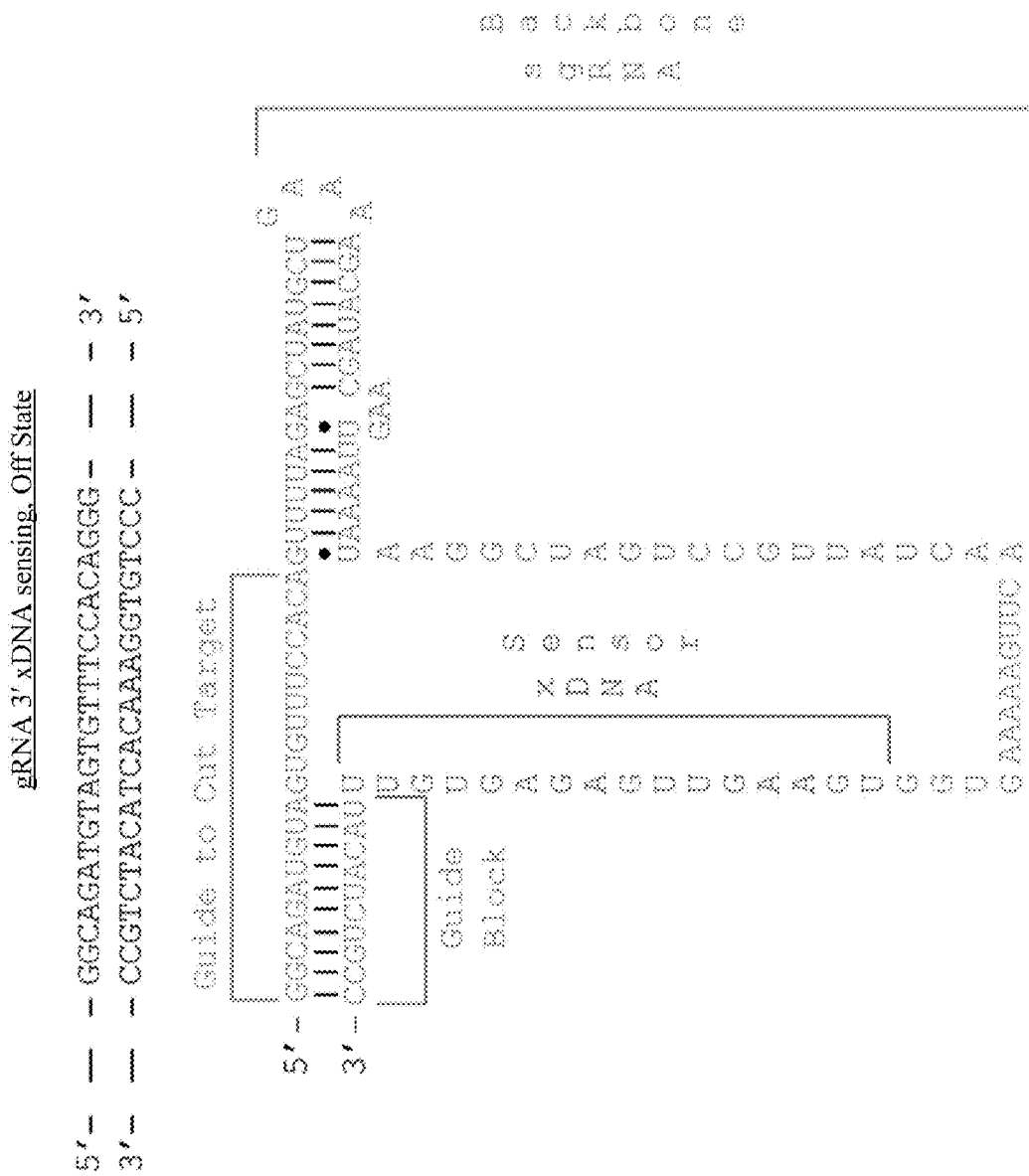
Figure 3D:
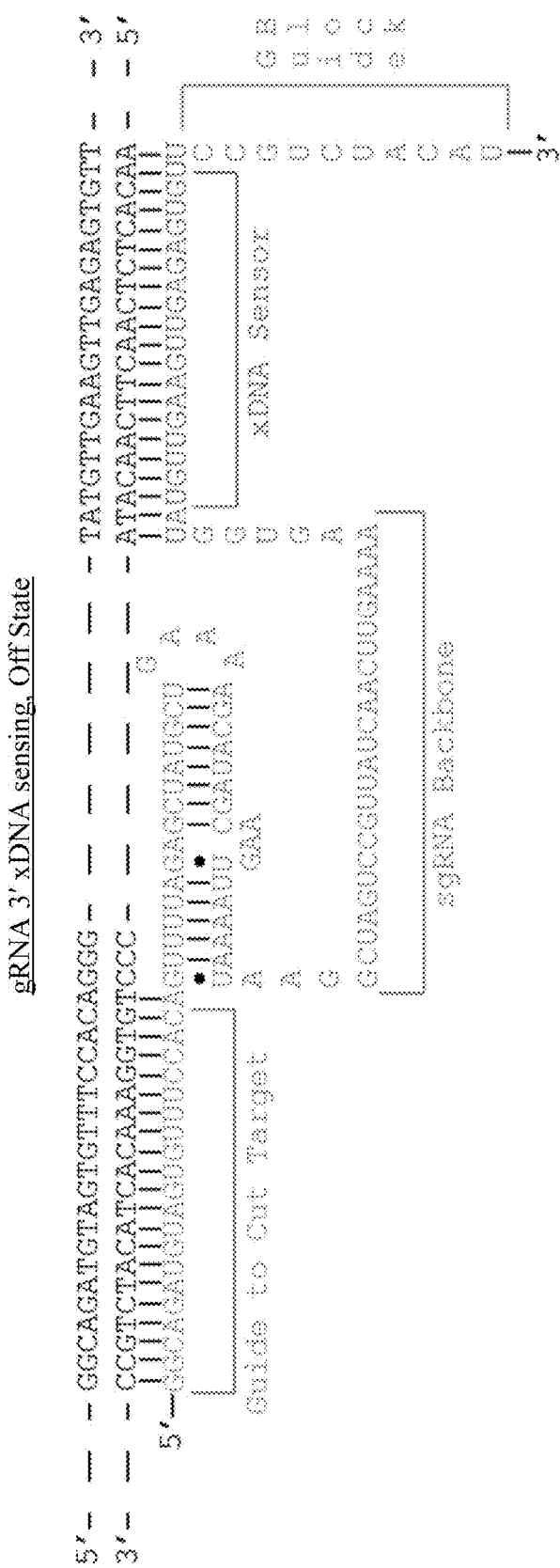

The term "RNA-programmable nuclease," and "RNA-guided nuclease" are used interchangeably herein and refer to a nuclease that forms a complex with (e.g., binds or associates with) one or more RNA that is not a target for cleavage. In some embodiments, an RNA-programmable nuclease, when in a complex with an RNA, may be referred to as a nuclease: RNA complex. Typically, the bound RNA(s) is referred to as a guide RNA (gRNA). gRNAs can exist as a complex of two or more RNAs, or as a single RNA molecule. gRNAs that exist as a single RNA molecule may be referred to as single-guide RNAs (sgRNAs), though "gRNA" is used interchangeabley to refer to guide RNAs that exist as either single molecules or as a complex of two or more molecules. Typically, gRNAs that exist as single RNA species comprise at least two domains: (1) a domain that shares homology to a target nucleic acid (e.g., and directs binding of a Cas9 complex to the target); and (2) a domain that binds a Cas9 protein. In some embodiments, domain (2) is the "sgRNA Backbone as depicted in any of the FIGS. 1-4. In some embodiments, domain (2) corresponds to a sequence known as a tracrRNA, and comprises a stem-loop structure. For example, in some embodiments, domain (2) is homologous to a tracrRNA as depicted in FIG. 1E of Jinek et al., *Science* 337:816-821 (2012), the entire contents of which is incorporated herein by reference. In some embodiments, domain 2 is at least 90%, at least 95%, at least 98%, or at least 99% identical to the "sgRNA backbone" of any one of FIGS. 1-4 or the tracrRNA as described by Jinek et al., *Science* 337:816-821(2012). In some embodiments, a gRNA comprises two or more of domains (1) and (2), and may be referred to as an "extended gRNA." For example, an extended gRNA will bind two or more Cas9 proteins and bind a target nucleic acid at two or more distinct regions. The gRNA comprises a nucleotide sequence that complements a target site, which mediates binding of the nuclease/RNA complex to said target site and providing the sequence specificity of the nuclease:RNA complex. The sequence of a gRNA that binds a target nucleic acid can comprise any sequence that complements a region of the target and is suitable for a nuclease:RNA complex to bind. In some embodiments, the RNA-programmable nuclease is the (CRISPR-associated system) Cas9 endonuclease, for example, Cas9 (Csn1) from *Streptococcus pyogenes* (see, e.g., "Complete genome sequence of an M1 strain of *Streptococcus pyogenes*." Ferretti J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L. expand/collapse author list McLaughlin R. E., Proc. Natl. Acad. Sci. U.S.A. 98:4658-4663(2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., Nature 471:602-607 (2011); and "A programmable dual-RNA-guided DNA endonuclease in adaptive bacterial immunity." Jinek M., Chylinski K., Fonfara I., Hauer M., Doudna J. A., Charpentier E. Science 337:816-821(2012), the entire contents of each of which are incorporated herein by reference.

Because RNA-programmable nucleases (e.g., Cas9) use RNA:DNA hybridization to determine target DNA cleavage sites, these proteins are able to cleave, in principle, any sequence specified by the guide RNA. Methods of using RNA-programmable nucleases, such as Cas9, for site-specific cleavage (e.g., to modify a genome) are known in the art (see e.g., Cong, L. et al. Multiplex genome engineering using CRISPR/Cas systems. *Science* 339, 819-823 (2013); Mali, P. et al. RNA-guided human genome engineering via Cas9. *Science* 339, 823-826 (2013); Hwang, W. Y. et al. Efficient genome editing in zebrafish using a CRISPR-Cas system. *Nature biotechnology* 31, 227-229 (2013); Jinek, M. et al. RNA-programmed genome editing in human cells. eLife 2, e00471 (2013); Dicarlo, J. E. et al. Genome engineering in *Saccharomyces cerevisiae* using CRISPR-Cas systems. Nucleic acids research (2013); Jiang, W. et al. RNA-guided editing of bacterial genomes using CRISPR-Cas systems. *Nature biotechnology* 31, 233-239 (2013); the entire contents of each of which are incorporated herein by reference).

The terms "small molecule" and "organic compound" are used interchangeably herein and refer to molecules, whether naturally-occurring or artificially created (e.g., via chemical synthesis) that have a relatively low molecular weight. Typically, an organic compound contains carbon. An organic compound may contain multiple carbon-carbon bonds, stereocenters, and other functional groups (e.g., amines, hydroxyl, carbonyls, or heterocyclic rings). In some embodiments, organic compounds are monomeric and have a molecular weight of less than about 1500 g/mol. In certain embodiments, the molecular weight of the small molecule is less than about 1000 g/mol or less than about 500 g/mol. In certain embodiments, the small molecule is a drug, for example, a drug that has already been deemed safe and effective for use in humans or animals by the appropriate governmental agency or regulatory body. In certain embodiments, the small molecule is known to bind an aptamer. In some embodiments, the organic compound is an antibiotic drug, for example, an anticancer antibiotic such as dynemicin, neocarzinostatin, calicheamicin, esperamicin, bleomycin, or a derivative thereof.

The term "subject," as used herein, refers to an individual organism, for example, an individual mammal. In some embodiments, the subject is a human. In some embodiments, the subject is a non-human mammal. In some embodiments, the subject is a non-human primate. In some embodiments, the subject is a rodent. In some embodiments, the subject is a sheep, a goat, a cattle, a cat, or a dog. In some embodiments, the subject is a vertebrate, an amphibian, a reptile, a fish, an insect, a fly, or a nematode. In some embodiments, the subject is a research animal. In some embodiments, the subject is genetically engineered, e.g., a genetically engineered non-human subject. The subject may be of either sex and at any stage of development.

The terms "target nucleic acid," and "target genome," as used herein in the context of nucleases, refer to a nucleic acid molecule or a genome, respectively, that comprises at least one target site of a given nuclease.

The term "target site," used herein interchangeably with the term "nuclease target site," refers to a sequence within a nucleic acid molecule that is bound and cleaved by a nuclease. A target site may be single-stranded or double-stranded. In the context of RNA-guided (e.g., RNA-programmable) nucleases (e.g., a protein dimer comprising a Cas9 gRNA binding domain and an active Cas9 DNA cleavage domain), a target site typically comprises a nucleotide sequence that is complementary to a gRNA of the RNA-programmable nuclease, and a protospacer adjacent motif (PAM) at the 3' end adjacent to the gRNA-complementary sequence. For the RNA-guided nuclease Cas9, the target site may be, in some embodiments, 20 base pairs plus a 3 base pair PAM (e.g., NNN, wherein N represents any nucleotide). Typically, the first nucleotide of a PAM can be any nucleotide, while the two downstream nucleotides are specified depending on the specific RNA-guided nuclease. Exemplary target sites for RNA-guided nucleases, such as Cas9, are known to those of skill in the art and include, without limitation, NNG, NGN, NAG, and NGG, wherein N represents any nucleotide. In addition, Cas9 nucleases from different species (e.g., *S. thermophilus* instead of *S. pyogenes*) recognize a PAM that comprises the sequence: NGGNG. Additional PAM sequences are known, including, but not limited to, NNAGAAW and NAAR (see, e.g., Esvelt and Wang, *Molecular Systems Biology*, 9:641 (2013), the entire contents of which are incorporated herein by reference). For example, the target site of an RNA-guided nuclease, such as, e.g., Cas9, may comprise the structure [$N_z$]-[PAM], where each N is, independently, any nucleotide, and $z$ is an integer between 1 and 50. In some embodiments, $z$ is at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, or at least 50. In some embodiments, $z$ is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In some embodiments, Z is 20. In some embodiments, "target site" may also refer to a sequence within a nucleic acid molecule that is bound but not cleaved by a nuclease.

The terms "treatment," "treat," and "treating," refer to a clinical intervention aimed to reverse, alleviate, delay the onset of, or inhibit the progress of a disease or disorder, or one or more symptoms thereof, as described herein. As used herein, the terms "treatment," "treat," and "treating" refer to a clinical intervention aimed to reverse, alleviate, delay the onset of, or inhibit the progress of a disease or disorder, or one or more symptoms thereof, as described herein. In some embodiments, treatment may be administered after one or more symptoms have developed and/or after a disease has been diagnosed. In other embodiments, treatment may be administered in the absence of symptoms, e.g., to prevent or delay onset of a symptom or inhibit onset or progression of a disease. For example, treatment may be administered to a susceptible individual prior to the onset of symptoms (e.g., in light of a history of symptoms and/or in light of genetic or other susceptibility factors). Treatment may also be continued after symptoms have resolved, for example, to prevent or delay their recurrence.

The term "vector" refers to a polynucleotide comprising one or more recombinant polynucleotides of the present invention, e.g., those encoding a gRNA provided herein and/or a Cas9 protein. Vectors include, but are not limited to, plasmids, viral vectors, cosmids, artificial chromosomes, and phagemids. The vector is one which is able to replicate in a host cell, and which is further characterized by one or more endonuclease restriction sites at which the vector may be cut and into which a desired nucleic acid sequence may be inserted. Vectors may contain one or more marker sequences suitable for use in the identification and/or selection of cells which have or have not been transformed or genomically modified with the vector. Markers include, for example, genes encoding proteins which increase or decrease either resistance or sensitivity to antibiotics (e.g., kanamycin, ampicillin) or other compounds, genes which encode enzymes whose activities are detectable by standard assays known in the art (e.g., β-galactosidase, alkaline phosphatase or luciferase), and genes which visibly affect the phenotype of transformed or transfected cells, hosts, colonies, or plaques. Any vector suitable for the transformation of a host cell, (e.g., *E. coli*, mammalian cells such as CHO cell, insect cells, etc.) as embraced by the present invention, for example vectors belonging to the pUC series, pGEM series, pET series, pBAD series, pTET series, or pGEX series. In some embodiments, the vector is suitable for transforming a host cell for recombinant protein production. Methods for selecting and engineering vectors and host cells for expressing gRNAs and/or proteins (e.g., those provided herein), transforming cells, and expressing/purifying recombinant proteins are well known in the art, and are provided by, for example, Green and Sambrook, *Molecular Cloning: A Laboratory Manual* (4$^{th}$ ed., Cold Spring Harbor Laboratory Press, Cold Spring Harbor, N.Y. (2012)).

DETAILED DESCRIPTION OF CERTAIN EMBODIMENTS OF THE INVENTION

Site-Specific Nucleases are Powerful Tools for Targeted Genome Modification in vitro and in vivo. Some site-specific nucleases can theoretically achieve a level of specificity for a target cleavage site that would allow one to target a single unique site in a genome for cleavage without affecting any other genomic site. It has been reported that nuclease cleavage in living cells triggers a DNA repair mechanism that frequently results in a modification of the cleaved and repaired genomic sequence, for example, via homologous recombination or non-homologous end-joining. Accordingly, the targeted cleavage of a specific unique sequence within a genome opens up new avenues for gene targeting and gene modification in living cells, including cells that are hard to manipulate with conventional gene targeting methods, such as many human somatic or embryonic stem cells. Nuclease-mediated modification of disease-related sequences, e.g., the CCR-5 allele in HIV/AIDS patients, or of genes necessary for tumor neovascularization, can be used in the clinical context, and two site specific nucleases are currently in clinical trials (Perez, E. E. et al., "Establishment of HIV-1 resistance in CD4+T cells by genome editing using zinc-finger nucleases." *Nature Biotechnology.* 26, 808-816 (2008); ClinicalTrials.gov identifiers: NCT00842634, NCT01044654, NCT01252641, NCT01082926). Other diseases that can be treated using site-specific nucleases include, for example, diseases associated with triplet expansion (e.g., Huntington's disease, myotonic dystrophy, spinocerebellar atatxias, etc.) cystic fibrosis (by targeting the CFTR gene), cancer, autoimmune diseases, and viral infections.

One important problem with site-specific nuclease-mediated modification is off-target nuclease effects, e.g., the cleavage of genomic sequences that differ from the intended target sequence by one or more nucleotides. Undesired side effects of off-target cleavage range from insertion into unwanted loci during a gene targeting event to severe complications in a clinical scenario. Off-target cleavage of sequences encoding essential gene functions or tumor suppressor genes by an endonuclease administered to a subject may result in disease or even death of the subject. Accordingly, it is desirable to employ new strategies in designing nucleases having the greatest chance of minimizing off-target effects.

The methods and compositions of the present disclosure represent, in some aspects, an improvement over previous methods and compositions by providing means to control the temporal activity and/or increase the specificity of RNA-guided nucleases. For example, RNA-guided nucleases known in the art, both naturally occurring and those engineered, typically bind to and cleave DNA upon forming a complex with an RNA (e.g., a gRNA) that complements the target. Aspects of the present invention relate to the recognition that having temporal control over the timing of the binding of an RNA-guided nuclease:RNA complex to its target will decrease the likelihood of off-target effects by minimizing or controlling the amount of time a complex is able to bind to and cleave the target. Additionally, engineering gRNAs that only bind the target site to be cleaved, for example, using gRNAs with extended target recognition domains that block binding in the absence of the target, improves the specificity of RNA-guided nucleases and decreases the chances of off-target effects.

The strategies, methods, compositions, kits, and systems provided herein can be used to control the activity and/or improve the specificity of any RNA-guided nuclease (e.g., Cas9). Suitable nucleases for use with modified gRNA as described herein will be apparent to those of skill in the art based on this disclosure.

In certain embodiments, the strategies, methods, compositions, kits, and systems provided herein are utilized to control the timing of RNA-guided (e.g., RNA-programmable) nuclease activity. Whereas typical RNA-guided nucleases recognize and cleave a target sequence upon forming a nuclease:RNA complex, the modified gRNAs provided herein allow for control over target binding and cleavage. Other aspects provide gRNAs engineered to bind a target site only when the intended target site is present, thereby improving the specificity of a RNA-guided nuclease. While Cas9: gRNA complexes have been successfully used to modify both cells (Cong, L. et al. Multiplex genome engineering using CRISPR/Cas systems. *Science.* 339, 819-823 (2013); Mali, P. et al. RNA-guided human genome engineering via Cas9. *Science.* 339, 823-826 (2013); Jinek, M. et al. RNA-programmed genome editing in human cells. *eLife* 2, e00471 (2013)) and organisms (Hwang, W. Y. et al. Efficient genome editing in zebrafish using a CRISPR-Cas system. *Nature Biotechnology.* 31, 227-229 (2013)), a study using Cas9:guide RNA complexes to modify zebrafish embryos observed toxicity (e.g., off-target effects) at a rate similar to that of ZFNs and TALENs (Hwang, W. Y. et al. *Nature Biotechnology.* 31, 227-229 (2013)). Accordingly, aspects of the present disclosure aim to reduce the chances for Cas9 off-target effects using novel gRNA platforms that control for the timing of target binding and cleavage and/or improve the specificity of RNA-guided nucleases.

While of particular relevance to DNA and DNA-cleaving nucleases such as Cas9, the inventive concepts, methods, compositions, strategies, kits, and systems provided herein are not limited in this respect, but can be applied to any nucleic acid:nuclease system utilizing nucleic acid templates such as RNA to direct binding to a target nucleic acid.

Modified Guide RNAs (gRNAs)

Some aspects of this disclosure provide gRNAs engineered to have both an "on" and "off" state. In some aspects then, the gRNAs may collectively be referred to as "switchable gRNAs." For example, a switchable gRNA is said to be in an "off" state when the gRNA is in a structural state that prevents binding of the gRNA to a target nucleic acid. In some aspects, a gRNA in an "off" state can bind to its cognate RNA-guided nuclease (e.g., Cas9), however, the nuclease:gRNA complex (when the gRNA is in an "off" state) is unable to bind the target nucleic acid to mediate cleavage. In other aspects, a gRNA that is in an "off" state is unable to bind its target sequence or an RNA-guided nuclease, such as Cas9. Conversely, a switchable gRNA is said to be in an "on" state when the gRNA is in a structural state that allows binding of the gRNA to a target nucleic acid (e.g., as a complex with an RNA-guided nuclease such as Cas9). Some embodiments of this disclosure provide complexes comprising an inventive gRNA associated with an RNA-guided nuclease, such as Cas9, and methods of their use. Some embodiments of this disclosure provide nucleic acids encoding such gRNAs and/or RNA-guided nucleases (e.g., Cas9). Some embodiments of this disclosure provide expression constructs comprising such encoding nucleic acids.

Aptamer Based gRNAs

In one embodiment, gRNAs are provided that comprise an aptamer. See, e.g., FIG. 1. For example, in some embodiments, a gRNA is linked to an aptamer via a nucleotide linker, as described herein. Aptamers are typically RNA or peptide based molecules that bind a specific ligand with affinities, for example, that rival antibody:antigen interactions. In some embodiments, an aptamer binds its ligand with a $K_d$ between about 1 nM-10 µM, between about 1 nM-1 µM, between about 1 nM-500 nM, or between about 1 nM-100 nM. With RNA-based aptamers, for example, those found in riboswitches of mRNAs, binding of the ligand to the aptamer domain results in conformational changes that control expression (e.g., translation) of the mRNA. RNA aptamers have been successfully cloned and adapted to other molecules, for example, to control gene expression, or have been engineered/selected for particular ligands using SELEX (See, e.g., Dixon et al., "Reengineering orthogonally selective riboswitches." *PNAS* 2010; 107 (7): 2830-2835; Suess et al., "A theophylline responsive riboswitch based on helix slipping controls gene expression in vivo." *Nucleic Acids Res.* 2004; 32(4): 1610-1614; Ellington and Szostak, "In vitro selection of RNA molecules that bind specific ligands." *Nature.* 1990; 346:818-822; Tuerk and Gold, "Systematic evolution of ligands by exponential enrichment: RNA ligands to bacteriophage T4 DNA polymerase." *Science.* 1990; 249: 505-510; Burke and Gold, "RNA aptamers to the adenosine moiety of S-adenosyl methionine: structural inferences from variations on a theme and the reproducibility of SELEX." *Nucleic Acids Res.* 1997; 25(10):2020-4; Ulrich et al., "DNA and RNA aptamers: from tools for basic research towards therapeutic applications." *Comb Chem High Throughput Screen.* 2006; 9(8):619-32; Svobodová et al., "Comparison of different methods for generation of single-stranded DNA for SELEX processes. *Anal Bioanal Chem.* 2012; 404:835-842; the entire contents of each are hereby incorporated by reference). Ligands that bind aptamers include, but are not limited to, small molecules, metabolites, carbohydrates, proteins, peptides, or nucleic acids. As shown in FIG. 1, gRNAs linked to aptamers exist in an "off" state in the absence of the specific ligand that binds the aptamer. Typically, the "off" state is mediated by a structural feature that prevents all or a part of the sequence of the gRNA that hybridizes to the target nucleic acid from being free to hybridize with the target nucleic acid. For example, in some aspects, the gRNA comprising an aptamer is designed such that part of the aptamer sequence hybridizes to part or all of the gRNA sequence that hybridizes to the target. The sequence of the gRNA that binds a target (e.g., depicted as "Guide to Cut Target" in FIG. 1C, D, referred to herein as the "guide" sequence) can be engineered using methods known in the art to include any sequence that targets any desired nucleic acid target, and is therefore not limited to the sequence(s) depicted in the Figures, which are exemplary. Similarly, any suitable aptamer can be linked 5' or 3' to the gRNA sequences, and be modified to include nucleotides that will hybridize to a particular guide sequence in a gRNA using methods routine in the art. In some embodiments, the aptamers linked to any gRNA provided herein are RNA aptamers, as described herein. In some embodiments, the RNA aptamer is derived from (e.g., cloned from) a riboswitch. Any riboswitch may be used in the RNA aptamer. Exemplary riboswitches include, but are not limited to, theophylline riboswitches, thiamine pyrophosphate (TPP) riboswitches, adenosine cobalamin (AdoCbl) riboswitches, S-adenosyl methionine (SAM) riboswitches, SAH riboswitches, flavin mononucleotide (FMN) riboswitches, tetrahydrofolate riboswitches, lysine riboswitches, glycine riboswitches, purine riboswitches, GlmS riboswitches, and pre-queosine$_1$ (PreQ1) riboswitches. In some embodiments, the RNA aptamer is derived from a theophylline riboswitch. In some embodiments, the aptamer derived from the theophylline riboswitch comprises SEQ ID NO:3. In some embodiments, the underlined, bold portion of SEQ ID NO:3 can be modified such that any nucleotide therein is replaced with any other nucleotide, and/or can be modified by adding or deleting 1 or more nucleotides. For example, the underlined, bold portion can be modified so as to include a sequence that hybridizes to part or all of the sequence of the gRNA that hybridizes to the target nucleic acid. See, e.g., FIG. 1C. In some embodiments, the RNA aptamer is at least 80%, at least 85%, at least 90%, at least 95%, at least 98%, or at least 99% identical to SEQ ID NO:3.

```
                                              (SEQ ID NO: 3)
5'-GGUGAUACCAGCAUCGUCUUGAUGCCCUUGGCAGCACC-3'.
```

In some embodiments, the aptamer is non-naturally occurring (e.g., is not found in nature). For example, in some embodiments, the aptamer is engineered or selected from a library using SELEX. In some embodiments, the aptamer comprises at least 20, at least 30, at least 40, at least 50, at least 60, at least 70, at least 80, at least 90, at least 100, at least 110, at least 120, at least 130, at least 140, at least 150, at least 175, at least 200, at least 250, or at least 300 nucleotides. In some embodiments, the aptamer comprises 20-200, 20-150, 20-100, or 20-80 nucleotides. In some embodiments, the gRNA portion of provided RNAs (e.g., RNAs comprising a gRNA linked to an aptamer) comprises at least 50, at least 60, at least 70, at least 80, at least 90, at least 100, at least 110, at least 120, at least 130, at least 140, at least 150, at least 175, or at least 200 nucleotides. In some embodiments, the gRNA portion comprises 60-150, 60-100, or 60-80 nucleotides.

mRNA-Sensing gRNAs

According to another embodiment, gRNAs are provided that bind a target nucleic acid under certain conditions (e.g., in the presence of a metabolite, small molecule, nucleic acid, etc.). In some embodiments, the gRNAs are structurally precluded (e.g., are in an "off" state) from binding (e.g., hybridizing to) a target unless another molecule binds to (e.g., hybridizes to) the gRNA, resulting in a structural rearrangement corresponding to an "on" state. In some embodiments, the binding of a particular transcript (e.g., mRNA) to the gRNA turns the gRNA from an "off" state to an "on" state. See, e.g., FIG. 2. Such gRNAs are referred to as "mRNA-sensing" gRNAs. For example, in some aspects, gRNAs are provided that comprise: (i) a region that hybridizes a region of a target nucleic acid (e.g., the "guide" sequence); (ii) another region that partially or completely hybridizes to the sequence of region (i) (e.g., the "guide block" sequence); and (iii) a region that hybridizes to a region of a transcript (mRNA) (e.g., the "transcript sensor"). In some embodiments, each region (e.g., i-iii) comprises at least 5, at least 10, at least 15, at least 20, or at least 25 nucleotides. In some embodiments, the gRNA forms a stem-loop structure. In some embodiments the stem comprises the sequence of region (i) hybridized to part or all of the sequence of region (ii), and the loop is formed by part or all of the sequence of region (iii). In some embodiments, regions (ii) and (iii) are both either 5' or 3' to region (i). See, e.g., FIG. 2A vs. FIG. 2C. The sequence of the gRNA that binds a target (e.g., the "guide" sequence) can be engineered using methods known in the art to include any sequence that targets any desired nucleic acid target, and is therefore not limited to the sequence(s) depicted in the Figures, which are exemplary. Similarly, region (iii) (e.g., the transcript sensor) can be engineered to comprise any sequence that hybridizes an mRNA of interest using methods routine in the art. Likewise, region (ii) can be engineered to comprise a sequence that hybridizes to part or all of the "guide" sequence using methods routine in the art. For example, in some aspects, the mRNA is one that when expressed in a cell, the genomic modification of a target nucleic acid (e.g., gene) is desired. Thus, in the absence of the mRNA, the gRNA, when delivered to (or expressed in) a cell, remains in the "off" state. When the mRNA is present (e.g., expressed), it binds the transcript sensor of the gRNA, resulting in unfolding of the stem-loop structure that prevented hybridization of the "guide" sequence to the target nucleic acid, thereby turning the gRNA "on". See, e.g., FIGS. 2B and 2D. Provided gRNAs in an "on" state are able to associate with and guide RNA-guided nucleases (e.g., Cas9 proteins) to bind a target nucleic acid.

Extended-DNA-Sensing (xDNA-Sensing) gRNAs

According to another embodiment, modified gRNAs are provided that remain in an "off" state unless the gRNA hybridizes to a target nucleic acid at least two distinct regions. See, e.g., FIG. 3. Such gRNAs provide improved specificity to an RNA-guided nuclease (e.g., Cas9) because they effectively extend the recognition sequence of a particular gRNA/target interaction. Such gRNAs are referred to as "xDNA-sensing" gRNAs ("x" being short for "extended" DNA recognition). For example, gRNAs are provided that comprise: (i) a region that hybridizes a region of a target nucleic acid (e.g., the "guide" sequence); (ii) another region that partially or completely hybridizes to the sequence of region (i) (e.g., the "guide block"); and (iii) a region that hybridizes to another region of the target nucleic acid (e.g., the "xDNA sensor"). In some embodiments, the xDNA sensor must first bind the target nucleic acid before the guide sequence is able to bind the target. In some embodiments, the xDNA sensor binds the same strand of the target that the guide sequence binds. In some embodiments, the xDNA sensor and guide sequence bind different strands of the target nucleic acid. In some embodiments, the sequences of regions (i) and (ii) comprise at least 5, at least 10, at least 15, at least 20, or at least 25 nucleotides. In some embodiments, the sequence of region (iii) comprise at least 5, at least 10, at least 15, at least 20, at least 25, at least 30, at least 40, at least 50, at least 75, or at least 100 nucleotides. In some embodiments, the gRNA forms a stem-loop structure. For example, in some embodiments, the stem comprises the sequence of region (i) hybridized to part or all of the sequence of region (ii), and the loop is formed by part or all of the sequence of region (iii). In some embodiments, regions (i) and (iii) comprise sequences that are adjacent in the gRNA. In some embodiments, regions (ii) and (iii) are both either 5' or 3' to region (i). See, e.g., FIG. 3A vs. FIG. 3C. In some embodiments, region (ii) is located between regions (i) and (iii). The sequence of the gRNA that binds a target (e.g., the "guide" sequence) can be engineered using methods known in the art to include any sequence that targets any desired nucleic acid target, and is therefore not limited to the sequence(s) depicted in the Figures, which are exemplary. Similarly, region (iii) (e.g., the xDNA sensor) can be engineered to comprise any sequence that hybridizes another region (e.g., a different region than that targeted by the "guide" sequence) of the target nucleic acid using methods routine in the art. Likewise, region (ii) can be engineered to include a sequence that hybridizes to part or all of the "guide" sequence using methods routine in the art. Thus, in the absence of the correct target nucleic acid (e.g., a target comprising both regions to which the gRNA was designed to hybridize), the gRNA, when delivered to (or expressed in) a cell, remains in the "off" state. Without wishing to be bound by any particular theory, it is expected that when the gRNA (e.g., when associated with Cas9) comes into contact with the target nucleic acid, the xDNA sensor hybridizes to the target, which in turn unravels the stem-loop structure that blocks the "guide" sequence, turning the gRNA "on". If it is the correct target nucleic acid, the guide sequence will then hybridize to the target, and optionally the complex will cleave the target nucleic acid. See, e.g., FIGS. 3B and 3D.

Complexes

In some embodiments, complexes comprising any of the RNAs/gRNAs described herein (e.g., RNAs comprising a gRNA linked to an aptamer, gRNAs that sense mRNAs, or gRNAs comprising xDNA sensors) are provided. In some aspects, a complex comprising a provided RNA/gRNA associated with an RNA-guided nuclease is provided. In some embodiments, the RNA-guided nuclease is Cas9, a variant of Cas9, or a fragment of Cas9, for example as described herein. In some embodiments, the RNA-guided nuclease is any form of the Cas9 protein as provided in U.S. Provisional patent application, U.S. Ser. No. 61/874,609, filed Sep. 6, 2013, entitled "Cas9 Variants And Uses Thereof," and U.S. Provisional patent application, U.S. Ser. No. 61/874,746, filed Sep. 6, 2013, entitled "Delivery System For Functional Nucleases," the entire contents of each are hereby incorporated by reference in their entirety.

In some embodiments, the complex further comprises a ligand, e.g., a ligand that binds the aptamer of the RNA associated with the RNA-guided nuclease, as described herein. In some embodiments, the complex (e.g., comprising a provided RNA (gRNA):ligand:Cas9 protein) binds to and optionally cleaves a target nucleic acid. In some aspects, a complex comprising a "sensing" gRNA (e.g., mRNA or xDNA) and Cas9 binds to and optionally cleaves a target nucleic acid.

Pharmaceutical Compositions

In some embodiments, any of the gRNAs described herein are provided as part of a pharmaceutical composition. In some embodiments, the pharmaceutical composition further comprises an RNA-guided nuclease (e.g., Cas9) that forms a complex with an inventive gRNA. For example, some embodiments provide pharmaceutical compositions comprising a gRNA and an RNA-guided nuclease as provided herein, or a nucleic acid encoding such gRNAs and/or nuclease, and a pharmaceutically acceptable excipient. Pharmaceutical compositions may optionally comprise one or more additional therapeutically active substances.

In some embodiments, compositions provided herein are administered to a subject, for example, to a human subject, in order to effect a targeted genomic modification within the subject. In some embodiments, cells are obtained from the subject and contacted with a provided gRNA associated with an RNA-guided nuclease or nucleic acid(s) encoding such ex vivo. In some embodiments, cells removed from a subject and contacted ex vivo with an inventive gRNA:nuclease complex are re-introduced into the subject, optionally after the desired genomic modification has been effected or detected in the cells. Methods of delivering pharmaceutical compositions comprising nucleases are known, and are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties. Although the descriptions of pharmaceutical compositions provided herein are principally directed to pharmaceutical compositions which are suitable for administration to humans, it will be understood by the skilled artisan that such compositions are generally suitable for administration to animals or organisms of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, domesticated animals, pets, and commercially relevant mammals such as cattle, pigs, horses, sheep, cats, dogs, mice, and/or rats; and/or birds, including commercially relevant birds such as chickens, ducks, geese, and/or turkeys.

Formulations of the pharmaceutical compositions described herein may be prepared by any method known or hereafter developed in the art of pharmacology. In general, such preparatory methods include the step of bringing the active ingredient(s) into association with an excipient and/or one or more other accessory ingredients, and then, if necessary and/or desirable, shaping and/or packaging the product into a desired single- or multi-dose unit.

Pharmaceutical formulations may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's *The Science and Practice of Pharmacy*, 21$^{st}$ Edition, A. R. Gennaro (Lippincott, Williams & Wilkins, Baltimore, Md., 2006; incorporated in its entirety herein by reference) discloses various excipients used in formulating pharmaceutical compositions and known techniques for the preparation thereof. See also PCT application PCT/US2010/055131 (Publication number WO2011053982 A8, filed Nov. 2, 2010), incorporated in its entirety herein by reference, for additional suitable methods, reagents, excipients and solvents for producing pharmaceutical compositions comprising a nuclease. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this disclosure.

In some embodiments, compositions in accordance with the present invention may be used for treatment of any of a variety of diseases, disorders, and/or conditions, including but not limited to one or more of the following: autoimmune disorders (e.g. diabetes, lupus, multiple sclerosis, psoriasis, rheumatoid arthritis); inflammatory disorders (e.g. arthritis, pelvic inflammatory disease); infectious diseases (e.g. viral infections (e.g., HIV, HCV, RSV), bacterial infections, fungal infections, sepsis); neurological disorders (e.g. Alzheimer's disease, Huntington's disease; autism; Duchenne muscular dystrophy); cardiovascular disorders (e.g. atherosclerosis, hypercholesterolemia, thrombosis, clotting disorders, angiogenic disorders such as macular degeneration); proliferative disorders (e.g. cancer, benign neoplasms); respiratory disorders (e.g. chronic obstructive pulmonary disease); digestive disorders (e.g. inflammatory bowel disease, ulcers); musculoskeletal disorders (e.g. fibromyalgia, arthritis); endocrine, metabolic, and nutritional disorders (e.g. diabetes, osteoporosis); urological disorders (e.g. renal disease); psychological disorders (e.g. depression, schizophrenia); skin disorders (e.g. wounds, eczema); blood and lymphatic disorders (e.g. anemia, hemophilia); etc.

Methods for Site-Specific Nucleic Acid Cleavage

In another embodiment of this disclosure, methods for site-specific nucleic acid (e.g., DNA) cleavage are provided. In some embodiments, the methods comprise contacting a DNA with any of the Cas9:RNA complexes described herein. For example, in some embodiments, the method comprises contacting a DNA with a complex comprising: (i) gRNA linked to an aptamer as described herein, wherein the gRNA comprises a sequence that binds to a portion of the DNA; (ii) a ligand bound to the aptamer of the gRNA; and (iii) an RNA-guided nuclease (e.g., a Cas9 protein), under suitable conditions for the Cas9 nuclease to cleave DNA.

In some embodiments, methods for inducing site-specific DNA cleavage in a cell are provided. In some embodiments, the method comprises: (a) contacting a cell or expressing within a cell a gRNA comprising an aptamer as described herein, wherein the gRNA comprises a sequence capable of binding to a DNA target sequence; (b) contacting a cell or expressing within a cell an RNA-guided nuclease (e.g., a Cas9 protein); and (c) contacting the cell with a specific ligand that binds the aptamer of the gRNA, resulting in the formation of a gRNA:ligand:Cas9 complex that cleaves the DNA target. In some embodiments, the method comprises: (a) contacting the cell with a complex comprising a Cas9 protein and a gRNA comprising an aptamer as described herein, wherein the gRNA comprises a sequence capable of binding to a DNA target sequence; and (b) contacting the cell with a specific ligand that binds the aptamer of the gRNA, resulting in the formation of a gRNA:ligand:Cas9 complex that cleaves the DNA target. In some embodiments, steps (a) and (b) are performed simultaneously. In some embodiments, steps (a) and (b) are performed sequentially. Thus in some embodiments, wherein the cell is contacted with the ligand subsequent to the cell being contacted with the complex, control of cleavage is achieved because cleavage only occurs once the ligand has been delivered to the cell. In some embodiments of these methods, the ligand is not delivered to the cell, but is produced internally by the cell, for example as part of a physiological or pathophysiological process.

In some embodiments, methods for site-specific DNA cleavage are provided that utilize mRNA-sensing gRNAs as described herein. For example, in some embodiments, the method comprises contacting a DNA with a complex comprising an RNA-guided nuclease (e.g., a Cas9 protein) and an mRNA-sensing gRNA, wherein the gRNA comprises: (i) a region that hybridizes a region of a target nucleic acid; (ii) another region that partially or completely hybridizes to the sequence of region (i); and (iii) a region that hybridizes to a region of a transcript (mRNA). In some embodiments, cleavage occurs after the sequence in region (iii) hybridizes to the mRNA.

In other embodiments, methods for site-specific DNA cleavage are provided that utilize xDNA-sensing gRNAs as described herein. For example, in some embodiments, the method comprises contacting a DNA with a complex comprising an RNA-guided nuclease (e.g., a Cas9 protein) and an xDNA-sensing gRNA, wherein the gRNA comprises: (i) a region that hybridizes a region of a target nucleic acid; (ii) another region that partially or completely hybridizes to the sequence of region (i); and (iii) a region that hybridizes to another region of the target nucleic acid. In some embodiments, cleavage occurs after the sequence in region (iii) hybridizes to the region of the target nucleic acid that is not targeted by the "guide" sequence.

In some embodiments, any of the methods provided herein can be performed on DNA in a cell. For example, in some embodiments the DNA contacted by any RNA/gRNA-comprising complex provided herein is in a eukaryotic cell. In some embodiments, the eukaryotic cell is in an individual. In some embodiments, the individual is a human. In some embodiments, any of the methods provided herein are performed in vitro. In some embodiments, any of the methods provided herein are performed in vivo.

Polynucleotides, Vectors, Cells, Kits

In another embodiment of this disclosure, polynucleotides are provided that encode any of the gRNAs (and optionally any Cas9 protein) described herein. For example, polynucleotides encoding any of the gRNAs and/or Cas9 proteins described herein are provided, e.g., for recombinant expression and purification of inventive gRNAs, or complexes comprising such, e.g., complexes comprising inventive gRNAs and an RNA-guided nuclease (e.g., a Cas9 protein). In some embodiments, provided polynucleotides comprises one or more sequences encoding a gRNA, alone or in combination with a sequence encoding any of the Cas9 proteins described herein.

In some embodiments, vectors encoding any of the gRNAs (and optionally any Cas9 protein) described herein are provided, e.g., for recombinant expression and purification of inventive gRNAs, or complexes comprising inventive gRNAs and an RNA-guided nuclease (e.g., a Cas9 protein). In some embodiments, the vector comprises or is engineered to include a polynucleotide, e.g., those described herein. In some embodiments, the vector comprises one or more sequences encoding a gRNA and/or any Cas9 protein (e.g., as described herein). Typically, the vector comprises a sequence encoding an inventive gRNA operably linked to a promoter, such that the gRNA is expressed in a host cell.

In some embodiments, cells are provided for recombinant expression and purification of any of the gRNAs (and optionally any Cas9 protein) described herein. The cells include any cell suitable for recombinant RNA expression and optionally protein expression, for example, cells comprising a genetic construct expressing or capable of expressing an inventive gRNA (e.g., cells that have been transformed with one or more vectors described herein, or cells having genomic modifications that express an inventive gRNA and optionally any Cas9 protein provided herein from an allele that has been incorporated in the cell's genome). Methods for transforming cells, genetically modifying cells, and expressing genes and proteins in such cells are well known in the art, and include those provided by, for example, Green and Sambrook, *Molecular Cloning: A Laboratory Manual* ($4^{th}$ ed., Cold Spring Harbor Laboratory Press, Cold Spring Harbor, N.Y. (2012)) and Friedman and Rossi, *Gene Transfer: Delivery and Expression of DNA and RNA, A Laboratory Manual* ($1^{st}$ ed., Cold Spring Harbor Laboratory Press, Cold Spring Harbor, N.Y. (2006)).

Some aspects of this disclosure provide kits comprising any of the inventive gRNAs or complexes provided herein and optionally any Cas9 protein described herein. In some embodiments, the kit comprises any of the polynucleotides encoding a provided gRNA, and optionally any Cas9 protein. In some embodiments, the kit comprises a vector for recombinant expression of any inventive gRNA and optionally any Cas9 protein. In some embodiments, the kit comprises a cell that comprises a genetic construct for expressing any of the inventive gRNAs, complexes, and optionally any Cas9 protein provided herein. In some embodiments, the kit comprises an excipient and instructions for contacting any of the inventive compositions with the excipient to generate a composition suitable for contacting a nucleic acid with e.g., a complex of an inventive gRNA and a RNA-guided nuclease, such as Cas9. In some embodiments, the composition is suitable for contacting a nucleic acid within a genome. In some embodiments, the composition is suitable for delivering an inventive composition (e.g., a gRNA, complexes thereof with Cas9) to a cell. In some embodiments, the composition is suitable for delivering an inventive composition (e.g., a gRNA, complexes thereof with Cas9) to a subject. In some embodiments, the excipient is a pharmaceutically acceptable excipient.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

All publications, patents and sequence database entries mentioned herein, including those items listed above, are hereby incorporated by reference in their entirety as if each individual publication or patent was specifically and individually indicated to be incorporated by reference. In case of conflict, the present application, including any definitions herein, will control.

What is claimed is:

1. An extended DNA (xDNA)-sensing single-guide RNA (sgRNA) comprising:
   (1) a domain that binds a Cas9 protein, comprising a sgRNA backbone sequence forming a first stem-loop structure; and
   (2) a DNA-targeting domain, comprising
      (i) a guide region comprising a sequence of at least 10 contiguous nucleotides that is 100% complementary to a first region of a target DNA sequence;
      (ii) a guide block region comprising a sequence of at least 10 contiguous nucleotides that is 100% complementary to a nucleotide sequence of the guide region (i); and
      (iii) an xDNA sensor region that hybridizes to a second region of the target DNA,
      wherein the domain that binds a Cas9 protein (1) and the DNA-targeting domain (2) do not overlap, and wherein the guide region (i) and the guide block region (ii) do not overlap.

2. The xDNA-sensing sgRNA of claim 1, wherein region (i) comprises a sequence of at least 15 contiguous nucleotides that is 100% complementary to the first region of the target DNA sequence, region (ii) comprises a sequence of at least 15 contiguous nucleotides that is 100% complementary to the nucleotide sequence of the guide region (i), and wherein the xDNA sensor region comprises at least 10 nucleotides.

3. The xDNA-sensing sgRNA of claim 1, wherein the DNA-targeting domain (2) forms a second stem-loop structure in which the stem comprises a sequence of the guide block region (ii) hybridized to part or all of the guide region (i), and the loop is formed by part or all of the sequence of the xDNA sensor region (iii).

4. The xDNA-sensing sgRNA of claim 3, wherein the guide block region (ii) and the xDNA sensor region (iii) are both either 5' or 3' to the guide region (i).

5. The xDNA-sensing sgRNA of claim 3, wherein the second stem-loop structure forms in the absence of the target DNA that hybridizes to the xDNA sensor region (iii).

6. The xDNA-sensing sgRNA of claim 3, wherein binding of the target DNA to the xDNA sensor region (iii) results in the unfolding of the second stem-loop structure, or prevents the formation of the second stem-loop structure, such that the guide block region (ii) does not hybridize to the guide region (i).

7. The xDNA-sensing sgRNA of claim 1, wherein the sgRNA binds a Cas9 protein, and wherein the guide region (i) binds the target DNA when the xDNA sensor region (iii) binds the target DNA.

8. A complex comprising the xDNA-sensing sgRNA of claim 1 and a Cas9 protein.

9. The complex of claim 8 further comprising a target DNA.

10. An isolated polynucleotide encoding the xDNA-sensing sgRNA of claim 1.

11. A vector comprising the polynucleotide of claim 10.

12. A vector for recombinant expression comprising a polynucleotide encoding a xDNA-sensing gRNA of claim 1 and optionally a polynucleotide encoding a Cas9 protein.

13. An isolated cell comprising a genetic construct for expressing the xDNA-sensing sgRNA of claim 1.

14. A method for site specific DNA cleavage comprising contacting a DNA with a complex comprising Cas9 and the xDNA-sensing sgRNA of claim 1, wherein the binding of the complex to the DNA results in DNA cleavage.

15. The method of claim 14, wherein the DNA is in a cell.

16. The method of claim 15, wherein the cell is in vitro.

17. The method of claim 15, wherein the cell is a eukaryotic cell in an individual.

18. The method of claim 17, wherein the individual is a human.

19. The xDNA-sensing sgRNA of claim 1, wherein the stem loop structure of the sgRNA backbone comprises
   (a) a sequence that is homologous to a tracrRNA sequence; and
   (b) a sequence that is homologous to a crRNA sequence, wherein the sequences of (a) and (b) hybridize to form the stem of the stem-loop structure, and wherein the 5'-end of the tracrRNA is connected to the 3'-end of the crRNA sequence via a polynucleotide linker that forms the loop of the stem-loop structure.

20. The xDNA-sensing sgRNA of claim 1, wherein the sgRNA backbone sequence comprises a nucleotide sequence that is at least 90% identical the entire length of to the nucleotide sequence 5'-GUUUUAGAGCUAUGCUGAAAAG-CAUAGCAAGUUAAAAUAAGGCUAGUCCGUUAUC-3' (nucleotides 53-107 of SEQ ID NO: 9) and/or at least 90% identical the entire length of to the nucleotide sequence 5'-GUUUUAGAGCUAUGCUGAAAAGCAUAG-CAAGUUAAAAU-3' (nucleotides 22-59 of SEQ ID NO: 8).

21. The xDNA-sensing sgRNA of claim 1, wherein the stem loop of the sgRNA backbone is formed by the sequence 5'-GUUUUAGAGCUAUGCUGAAAAGCAUAG-CAAGUUAAAAU-3' (residues 53-90 of SEQ ID NO: 9).

22. The xDNA-sensing sgRNA of claim 1, wherein the guide block region (ii) is positioned 5' of the guide region (i).

23. The xDNA-sensing sgRNA of claim 1, wherein the xDNA sensor region (iii) is positioned 5' of the guide region (i).

24. The xDNA-sensing sgRNA of claim 1, wherein the guide block region (ii) and the xDNA sensor region (iii) are positioned 5' of the guide region (i).

25. The xDNA-sensing sgRNA of claim 1, wherein the first region and the second region of the target DNA do not overlap.

26. The xDNA-sensing sgRNA of claim 1, wherein the guide region (i) comprises at least 15 contiguous nucleotides that are 100% complementary to a nucleic acid sequence of the first region of the target DNA sequence.

27. The xDNA-sensing sgRNA of claim 1, wherein the guide region (i) comprises at least 20 contiguous nucleotides that are 100% complementary to a nucleic acid sequence of the first region of the target DNA sequence.

28. The xDNA-sensing sgRNA of claim 1, wherein the guide region (i) comprises at least 25 contiguous nucleotides that are 100% complementary to a nucleic acid sequence of the first region of the target DNA sequence.

29. The xDNA-sensing sgRNA of claim 1, wherein the target DNA sequence is a genomic DNA sequence.

30. The xDNA-sensing sgRNA of claim 1, wherein the guide region (i), the guide block region (ii) and the xDNA sensor region (iii) do not overlap.

* * * * *

SEQUENCE LISTING

<160> NUMBER OF SEQ ID NOS: 16

<210> SEQ ID NO 1
<211> LENGTH: 4104
<212> TYPE: DNA
<213> ORGANISM: Streptococcus pyogenes

<400> SEQUENCE: 1

| | | | | | | |
|---|---|---|---|---|---|---|
| atggataaga | aatactcaat | aggcttagat | atcggcacaa | atagcgtcgg | atgggcggtg | 60 |
| atcactgatg | attataaggt | tccgtctaaa | aagttcaagg | ttctgggaaa | tacagaccgc | 120 |
| cacagtatca | aaaaaaatct | tataggggct | cttttatttg | gcagtggaga | gacagcggaa | 180 |
| gcgactcgtc | tcaaacggac | agctcgtaga | aggtatacac | gtcggaagaa | tcgtatttgt | 240 |
| tatctacagg | agattttttc | aaatgagatg | gcgaaagtag | atgatagttt | ctttcatcga | 300 |
| cttgaagagt | cttttttggt | ggaagaagac | aagaagcatg | aacgtcatcc | tattttttgga | 360 |
| aatatagtag | atgaagttgc | ttatcatgag | aaatatccaa | ctatctatca | tctgcgaaaa | 420 |
| aaattggcag | attctactga | taaagcggat | ttgcgcttaa | tctatttggc | cttagcgcat | 480 |
| atgattaagt | ttcgtggtca | ttttttgatt | gagggagatt | taaatcctga | taatagtgat | 540 |
| gtggacaaac | tatttatcca | gttggtacaa | atctacaatc | aattatttga | agaaaaccct | 600 |
| attaacgcaa | gtagagtaga | tgctaaagcg | attctttctg | cacgattgag | taaatcaaga | 660 |
| cgattagaaa | atctcattgc | tcagctcccc | ggtgagaaga | gaaatggctt | gtttgggaat | 720 |
| ctcattgctt | tgtcattggg | attgaccccct | aattttaaat | caattttttga | tttggcagaa | 780 |
| gatgctaaat | tacagctttc | aaaagatact | tacgatgatg | atttagataa | tttattggcg | 840 |
| caaattggag | atcaatatgc | tgatttgttt | ttggcagcta | agaatttatc | agatgctatt | 900 |
| ttactttcag | atatcctaag | agtaaatagt | gaaataacta | aggctcccct | atcagcttca | 960 |
| atgattaagc | gctacgatga | acatcatcaa | gacttgactc | ttttaaaagc | tttagttcga | 1020 |
| caacaacttc | cagaaaagta | taaagaaatc | ttttttgatc | aatcaaaaaa | cggatatgca | 1080 |
| ggttatattg | atgggggagc | tagccaagaa | gaatttttata | aatttatcaa | accaatttta | 1140 |
| gaaaaaatgg | atggtactga | ggaattattg | gtgaaactaa | atcgtgaaga | tttgctgcgc | 1200 |
| aagcaacgga | cctttgacaa | cggctctatt | ccccatcaaa | ttcacttggg | tgagctgcat | 1260 |
| gctatttttga | gaagacaaga | agacttttat | ccattttttaa | aagacaatcg | tgagaagatt | 1320 |
| gaaaaaatct | tgacttttcg | aattccttat | tatgttggtc | cattggcgcg | tggcaatagt | 1380 |
| cgttttgcat | ggatgactcg | gaagtctgaa | gaaacaatta | ccccatggaa | ttttgaagaa | 1440 |
| gttgtcgata | aggtgccttc | agctcaatca | tttattgaac | gcatgacaaa | ctttgataaa | 1500 |
| aatcttccaa | atgaaaaagt | actaccaaaa | catagtttgc | tttatgagta | ttttacggtt | 1560 |
| tataacgaat | tgacaaaggt | caaatatgtt | actgagggaa | tgcgaaaacc | agcatttctt | 1620 |
| tcaggtgaac | agaagaaagc | cattgttgat | ttactcttca | aaacaaatcg | aaaagtaacc | 1680 |
| gttaagcaat | aaaagaaga | ttatttcaaa | aaaatagaat | gttttgatag | tgttgaaatt | 1740 |
| tcaggagttg | aagatagatt | taatgcttca | ttaggcgcct | accatgattt | gctaaaaatt | 1800 |
| attaaagata | aagatttttt | ggataatgaa | gaaatgaag | atatcttaga | ggatattgtt | 1860 |
| ttaacattga | cctttatttga | agatagggg | atgattgagg | aaagacttaa | aacatatgct | 1920 |
| cacctcttttg | atgataaggt | gatgaaacag | cttaaacgtc | gccgttatac | tggttgggga | 1980 |
| cgtttgtctc | gaaaattgat | taatggtatt | agggataagc | aatctggcaa | aacaatatta | 2040 |
| gatttttttga | aatcagatgg | ttttgccaat | cgcaatttta | tgcagctgat | ccatgatgat | 2100 |

-continued

```
agtttgacat ttaaagaaga tattcaaaaa gcacaggtgt ctggacaagg ccatagttta    2160
catgaacaga ttgctaactt agctggcagt cctgctatta aaaaggtat tttacagact    2220 gtaaaaattg ttgatgaact ggtcaaagta atggggcata agccagaaaa tatcgttatt    2280
gaaatggcac gtgaaaatca gacaactcaa aagggccaga aaaattcgcg agagcgtatg    2340
aaacgaatcg aagaaggtat caaagaatta ggaagtcaga ttcttaaaga gcatcctgtt    2400
gaaaatactc aattgcaaaa tgaaaagctc tatctctatt atctacaaaa tggaagagac    2460
atgtatgtgg accaagaatt agatattaat cgtttaagtg attatgatgt cgatcacatt    2520
gttccacaaa gtttcattaa agacgattca atagacaata aggtactaac gcgttctgat    2580
aaaaatcgtg gtaaatcgga taacgttcca agtgaagaag tagtcaaaaa gatgaaaaac    2640
tattggagac aacttctaaa cgccaagtta atcactcaac gtaagtttga taatttaacg    2700
aaagctgaac gtggaggttt gagtgaactt gataaagctg gttttatcaa acgccaattg    2760
gttgaaactc gccaaatcac taagcatgtg gcacaaattt tggatagtcg catgaatact    2820
aaatacgatg aaaatgataa acttattcga gaggttaaag tgattacctt aaaatctaaa    2880
ttagtttctg acttccgaaa agatttccaa ttctataaag tacgtgagat taacaattac    2940
catcatgccc atgatgcgta tctaaatgcc gtcgttggaa ctgctttgat taagaaatat    3000
ccaaaacttg aatcggagtt tgtctatggt gattataaag tttatgatgt tcgtaaaatg    3060
attgctaagt ctgagcaaga aataggcaaa gcaaccgcaa atatttcttt ttactctaat    3120
atcatgaact tcttcaaaac agaaattaca cttgcaaatg gagagattcg caaacgccct    3180
ctaatcgaaa ctaatgggga aactggagaa attgtctggg ataaagggcg agattttgcc    3240
acagtgcgca aagtattgtc catgccccaa gtcaatattg tcaagaaaac agaagtacag    3300
acaggcggat tctccaagga gtcaattttta ccaaaaagaa attcggacaa gcttattgct    3360
cgtaaaaaag actgggatcc aaaaaaatat ggtggttttg atagtccaac ggtagcttat    3420
tcagtcctag tggttgctaa ggtggaaaaa gggaaatcga agaagttaaa atccgttaaa    3480
gagttactag ggatcacaat tatggaagaa gttcctttg aaaaaaatcc gattgactttt    3540 ttagaagcta aaggatataa ggaagttaaa aaagacttaa tcattaaact acctaaatat    3600 agtcttttg agttagaaaa cggtcgtaaa cggatgctgg ctagtgccgg agaattacaa    3660
aaaggaaatg agctggctct gccaagcaaa tatgtgaatt ttttatattt agctagtcat    3720
tatgaaaagt tgaagggtag tccagaagat aacgaacaaa aacaattgtt tgtggagcag    3780
cataagcatt atttagatga gattattgag caaatcagtg aattttctaa gcgtgttatt    3840
ttagcagatg ccaatttaga taaagttctt agtgcatata acaaacatag agacaaacca    3900
atacgtgaac aagcagaaaa tattattcat ttatttacgt tgacgaatct ggagctcccc    3960
gctgctttta aatattttga tacaacaatt gatcgtaaac gatatacgtc tacaaaagaa    4020
gttttagatg ccactcttat ccatcaatcc atcactggtc tttatgaaac acgcattgat    4080
ttgagtcagc taggaggtga ctga                                          4104
```

<210> SEQ ID NO 2
<211> LENGTH: 1367
<212> TYPE: PRT
<213> ORGANISM: Streptococcus pyogenes

<400> SEQUENCE: 2

```
Met Asp Lys Lys Tyr Ser Ile Gly Leu Asp Ile Gly Thr Asn Ser Val
1               5                   10                  15
```

```
Gly Trp Ala Val Ile Thr Asp Asp Tyr Lys Val Pro Ser Lys Lys Phe
                20              25              30

Lys Val Leu Gly Asn Thr Asp Arg His Ser Ile Lys Lys Asn Leu Ile
            35              40              45

Gly Ala Leu Leu Phe Gly Ser Gly Glu Thr Ala Glu Ala Thr Arg Leu
 50              55              60

Lys Arg Thr Ala Arg Arg Tyr Thr Arg Arg Lys Asn Arg Ile Cys
 65              70              75              80

Tyr Leu Gln Glu Ile Phe Ser Asn Glu Met Ala Lys Val Asp Asp Ser
                85              90              95

Phe Phe His Arg Leu Glu Glu Ser Phe Leu Val Glu Glu Asp Lys Lys
            100             105             110

His Glu Arg His Pro Ile Phe Gly Asn Ile Val Asp Glu Val Ala Tyr
            115             120             125

His Glu Lys Tyr Pro Thr Ile Tyr His Leu Arg Lys Lys Leu Ala Asp
        130             135             140

Ser Thr Asp Lys Ala Asp Leu Arg Leu Ile Tyr Leu Ala Leu Ala His
145             150             155             160

Met Ile Lys Phe Arg Gly His Phe Leu Ile Glu Gly Asp Leu Asn Pro
                165             170             175

Asp Asn Ser Asp Val Asp Lys Leu Phe Ile Gln Leu Val Gln Ile Tyr
            180             185             190

Asn Gln Leu Phe Glu Glu Asn Pro Ile Asn Ala Ser Arg Val Asp Ala
        195             200             205

Lys Ala Ile Leu Ser Ala Arg Leu Ser Lys Ser Arg Arg Leu Glu Asn
        210             215             220

Leu Ile Ala Gln Leu Pro Gly Glu Lys Arg Asn Gly Leu Phe Gly Asn
225             230             235             240

Leu Ile Ala Leu Ser Leu Gly Leu Thr Pro Asn Phe Lys Ser Asn Phe
            245             250             255

Asp Leu Ala Glu Asp Ala Lys Leu Gln Leu Ser Lys Asp Thr Tyr Asp
            260             265             270

Asp Asp Leu Asp Asn Leu Leu Ala Gln Ile Gly Asp Gln Tyr Ala Asp
        275             280             285

Leu Phe Leu Ala Ala Lys Asn Leu Ser Asp Ala Ile Leu Leu Ser Asp
290             295             300

Ile Leu Arg Val Asn Ser Glu Ile Thr Lys Ala Pro Leu Ser Ala Ser
305             310             315             320

Met Ile Lys Arg Tyr Asp Glu His His Gln Asp Leu Thr Leu Leu Lys
            325             330             335

Ala Leu Val Arg Gln Gln Leu Pro Glu Lys Tyr Lys Glu Ile Phe Phe
            340             345             350

Asp Gln Ser Lys Asn Gly Tyr Ala Gly Tyr Ile Asp Gly Gly Ala Ser
        355             360             365

Gln Glu Glu Phe Tyr Lys Phe Ile Lys Pro Ile Leu Glu Lys Met Asp
        370             375             380

Gly Thr Glu Glu Leu Leu Val Lys Leu Asn Arg Glu Asp Leu Leu Arg
385             390             395             400

Lys Gln Arg Thr Phe Asp Asn Gly Ser Ile Pro His Gln Ile His Leu
            405             410             415

Gly Glu Leu His Ala Ile Leu Arg Arg Gln Glu Asp Phe Tyr Pro Phe
            420             425             430
```

-continued

```
Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Ala Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
            610                 615                 620

Leu Phe Glu Asp Arg Gly Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly His Ser Leu
705                 710                 715                 720

His Glu Gln Ile Ala Asn Leu Ala Gly Ser Pro Ala Ile Lys Lys Gly
                725                 730                 735

Ile Leu Gln Thr Val Lys Ile Val Asp Glu Leu Val Lys Val Met Gly
            740                 745                 750

His Lys Pro Glu Asn Ile Val Ile Glu Met Ala Arg Glu Asn Gln Thr
            755                 760                 765

Thr Gln Lys Gly Gln Lys Asn Ser Arg Glu Arg Met Lys Arg Ile Glu
770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
            820                 825                 830

Ser Asp Tyr Asp Val Asp His Ile Val Pro Gln Ser Phe Ile Lys Asp
            835                 840                 845

Asp Ser Ile Asp Asn Lys Val Leu Thr Arg Ser Asp Lys Asn Arg Gly
```

```
                850           855           860
Lys Ser Asp Asn Val Pro Ser Glu Glu Val Val Lys Lys Met Lys Asn
865               870               875               880

Tyr Trp Arg Gln Leu Leu Asn Ala Lys Leu Ile Thr Gln Arg Lys Phe
              885               890               895

Asp Asn Leu Thr Lys Ala Glu Arg Gly Gly Leu Ser Glu Leu Asp Lys
              900               905               910

Ala Gly Phe Ile Lys Arg Gln Leu Val Glu Thr Arg Gln Ile Thr Lys
          915               920               925

His Val Ala Gln Ile Leu Asp Ser Arg Met Asn Thr Lys Tyr Asp Glu
          930               935               940

Asn Asp Lys Leu Ile Arg Glu Val Lys Val Ile Thr Leu Lys Ser Lys
945               950               955               960

Leu Val Ser Asp Phe Arg Lys Asp Phe Gln Phe Tyr Lys Val Arg Glu
              965               970               975

Ile Asn Asn Tyr His His Ala His Asp Ala Tyr Leu Asn Ala Val Val
              980               985               990

Gly Thr Ala Leu Ile Lys Lys Tyr Pro Lys Leu Glu Ser Glu Phe Val
          995               1000              1005

Tyr Gly Asp Tyr Lys Val Tyr Asp Val Arg Lys Met Ile Ala Lys
    1010              1015              1020

Ser Glu Gln Glu Ile Gly Lys Ala Thr Ala Lys Tyr Phe Phe Tyr
    1025              1030              1035

Ser Asn Ile Met Asn Phe Phe Lys Thr Glu Ile Thr Leu Ala Asn
    1040              1045              1050

Gly Glu Ile Arg Lys Arg Pro Leu Ile Glu Thr Asn Gly Glu Thr
    1055              1060              1065

Gly Glu Ile Val Trp Asp Lys Gly Arg Asp Phe Ala Thr Val Arg
    1070              1075              1080

Lys Val Leu Ser Met Pro Gln Val Asn Ile Val Lys Lys Thr Glu
    1085              1090              1095

Val Gln Thr Gly Gly Phe Ser Lys Glu Ser Ile Leu Pro Lys Arg
    1100              1105              1110

Asn Ser Asp Lys Leu Ile Ala Arg Lys Lys Asp Trp Asp Pro Lys
    1115              1120              1125

Lys Tyr Gly Gly Phe Asp Ser Pro Thr Val Ala Tyr Ser Val Leu
    1130              1135              1140

Val Val Ala Lys Val Glu Lys Gly Lys Ser Lys Lys Leu Lys Ser
    1145              1150              1155

Val Lys Glu Leu Leu Gly Ile Thr Ile Met Glu Arg Ser Ser Phe
    1160              1165              1170

Glu Lys Asn Pro Ile Asp Phe Leu Glu Ala Lys Gly Tyr Lys Glu
    1175              1180              1185

Val Lys Lys Asp Leu Ile Ile Lys Leu Pro Lys Tyr Ser Leu Phe
    1190              1195              1200

Glu Leu Glu Asn Gly Arg Lys Arg Met Leu Ala Ser Ala Gly Glu
    1205              1210              1215

Leu Gln Lys Gly Asn Glu Leu Ala Leu Pro Ser Lys Tyr Val Asn
    1220              1225              1230

Phe Leu Tyr Leu Ala Ser His Tyr Glu Lys Leu Lys Gly Ser Pro
    1235              1240              1245

Glu Asp Asn Glu Gln Lys Gln Leu Phe Val Glu Gln His Lys His
    1250              1255              1260
```

| Tyr | Leu | Asp | Glu | Ile | Ile | Glu | Gln | Ile | Ser | Glu | Phe | Ser | Lys | Arg |
| | 1265 | | | | 1270 | | | | 1275 | | | | | |

| Val | Ile | Leu | Ala | Asp | Ala | Asn | Leu | Asp | Lys | Val | Leu | Ser | Ala | Tyr |
| 1280 | | | | | 1285 | | | | 1290 | | | | | |

| Asn | Lys | His | Arg | Asp | Lys | Pro | Ile | Arg | Glu | Gln | Ala | Glu | Asn | Ile |
| | 1295 | | | | 1300 | | | | 1305 | | | | | |

| Ile | His | Leu | Phe | Thr | Leu | Thr | Asn | Leu | Gly | Ala | Pro | Ala | Ala | Phe |
| | 1310 | | | | 1315 | | | | 1320 | | | | | |

| Lys | Tyr | Phe | Asp | Thr | Thr | Ile | Asp | Arg | Lys | Arg | Tyr | Thr | Ser | Thr |
| 1325 | | | | | 1330 | | | | 1335 | | | | | |

| Lys | Glu | Val | Leu | Asp | Ala | Thr | Leu | Ile | His | Gln | Ser | Ile | Thr | Gly |
| 1340 | | | | | 1345 | | | | 1350 | | | | | |

| Leu | Tyr | Glu | Thr | Arg | Ile | Asp | Leu | Ser | Gln | Leu | Gly | Gly | Asp | |
| | 1355 | | | | 1360 | | | | 1365 | | | | | |

<210> SEQ ID NO 3
<211> LENGTH: 38
<212> TYPE: RNA
<213> ORGANISM: Artificial Sequence
<220> FEATURE:
<223> OTHER INFORMATION: Synthetic Polynucleotide

<400> SEQUENCE: 3
ggugauacca gcaucgucuu gaugcccuug gcagcacc         38

<210> SEQ ID NO 4
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 4
ggcagatgta gtgtttccac aggg         24

<210> SEQ ID NO 5
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 5
ccgtctacat cacaaaggtg tccc         24

<210> SEQ ID NO 6
<211> LENGTH: 133
<212> TYPE: RNA
<213> ORGANISM: Artificial Sequence
<220> FEATURE:
<223> OTHER INFORMATION: Synthetic Polynucleotide

<400> SEQUENCE: 6
ggugauacca gcaucgucuu gaugcccuug gcagcacccg cugcgcaggg gguaucaggc         60
agauguagug uuuccacagu uuuagagcua ugcugaaaag cauagcaagu uaaaauaagg        120
cuaguccguu auc         133

<210> SEQ ID NO 7
<211> LENGTH: 107
<212> TYPE: RNA
<213> ORGANISM: Artificial Sequence

```
<220> FEATURE:
<223> OTHER INFORMATION: Synthetic Polynucleotide

<400> SEQUENCE: 7
uacaucugcc uugugagagu ugaaguugua uggcagaugu aguguuucca caguuuuaga    60
gcuaugcuga aaagcauagc aaguuaaaau aaggcuaguc cguuauc                  107

<210> SEQ ID NO 8
<211> LENGTH: 90
<212> TYPE: RNA
<213> ORGANISM: Artificial Sequence
<220> FEATURE:
<223> OTHER INFORMATION: Synthetic Polynucleotide

<400> SEQUENCE: 8
ggcagaugua guguuccac aguuuuagag cuaugcugaa aagcauagca aguuaaaauu     60
auguugaagu ugagaguguu uacaucugcc                                    90

<210> SEQ ID NO 9
<211> LENGTH: 107
<212> TYPE: RNA
<213> ORGANISM: Artificial Sequence
<220> FEATURE:
<223> OTHER INFORMATION: Synthetic Polynucleotide

<400> SEQUENCE: 9
uacaucugcc uugugagagu ugaaguugua uggcagaugu aguguuucca caguuuuaga    60
gcuaugcuga aaagcauagc aaguuaaaau aaggcuaguc cguuauc                  107

<210> SEQ ID NO 10
<211> LENGTH: 117
<212> TYPE: RNA
<213> ORGANISM: Artificial Sequence
<220> FEATURE:
<223> OTHER INFORMATION: Synthetic Polynucleotide

<400> SEQUENCE: 10
ggcagaugua guguuccac aguuuuagag cuaugcugaa aagcauagca aguuaaaaua     60
aggcuagucc guuaucaacu ugaaaaagug gugaaguuga gaguguuuac aucugcc      117

<210> SEQ ID NO 11
<211> LENGTH: 134
<212> TYPE: RNA
<213> ORGANISM: Artificial Sequence
<220> FEATURE:
<223> OTHER INFORMATION: Synthetic Polynucleotide

<400> SEQUENCE: 11
ggugauacca gcaucguuug augcccuugg cagcaccgcu gcgcaggggg uaucaacagg    60
cagauguagu guuccacag uuuuagagcu augcugaaaa gcauagcaag uuaaaauaag    120
gcuaguccgu uauc                                                     134

<210> SEQ ID NO 12
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 12
auacaacuuc aacucucaca a                                             21
```

```
<210> SEQ ID NO 13
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 13
ttgtgagagt tgaagttgta tggcagatgt agtgtttcca caggg              45

<210> SEQ ID NO 14
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 14
ccctgtggaa acactacatc tgccatacaa cttcaactct cacaa              45

<210> SEQ ID NO 15
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 15
ggcagatgta gtgtttccac agggtatgtt gaagttgaga gtgtt              45

<210> SEQ ID NO 16
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 16
aacactctca acttcaacat accctgtgga aacactacat ctgcc              45
```